(12) United States Patent
Bubb et al.

(10) Patent No.: US 6,936,037 B2
(45) Date of Patent: Aug. 30, 2005

(54) TISSUE CLOSURE TREATMENT SYSTEM, PATIENT INTERFACE AND METHOD

(75) Inventors: Stephen K. Bubb, Kansas City, MO (US); David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 113 days.

(21) Appl. No.: 10/409,225

(22) Filed: Apr. 8, 2003

(65) Prior Publication Data

US 2004/0127863 A1 Jul. 1, 2004

Related U.S. Application Data

(63) Continuation-in-part of application No. 10/334,766, filed on Dec. 31, 2002.
(51) Int. Cl.[7] .......................... A61M 1/00; A61M 27/00; A61H 7/00
(52) U.S. Cl. ....................... 604/327; 604/541; 604/543; 604/268; 601/6
(58) Field of Search ................................. 604/289, 290, 604/304, 313, 540, 541, 543, 327, 268; 601/6

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,115,138 A | 12/1963 | MCElvenny et al. |
| 3,367,332 A | 2/1968 | Groves |
| 3,648,692 A | 3/1972 | Wheeler |

(Continued)

OTHER PUBLICATIONS

The Woodpecker, promotional literature for product manufactured by IMT (Integral Medizintechnik) and distributed by Minnestota Bramstedt Surgical, Inc.; Availabe at web site www.mnbramstedt.com.
Halkey–Roberts, St. Petersburg, Florida, Pocket Pump Assembly, Drawing dated Jul. 21, 1997. Available web site: www.halkey–roberts.com/showpic.asp?filename= V15500PPXMED.jpg, Acessed on Nov. 18, 2002.
Haemonetics:Products and Programs–OrthoPAT System, Availabel web site: www.haemonetics.com/site/content/products/...Accessed on Nov. 28, 2002.
PCT International Search Report; Application PCT/US03/41667, Stephen K. Bubb et al., Tissue Closure Treatment System, Patient Interface and Method.

*Primary Examiner*—Larry I. Schwartz
*Assistant Examiner*—Michael G. Bogart
(74) *Attorney, Agent, or Firm*—Mark E. Brown

(57) ABSTRACT

A tissue closure treatment system and method are provided with an external patient interface. A first fluid transfer component FTC.1 comprises a strip of porous material, such as rayon, with liquid wicking properties. FTC.1 can be placed directly on a suture line for transferring fluid exuded therethrough. An underdrape is placed over FTC.1 and includes a slot exposing a portion of same. FTC.2 comprises a suitable hydrophobic foam material, such as polyurethane ether, and is placed over the underdrape slot in communication with FTC.1. Negative pressure is applied to FTC.2 through a connecting fluid transfer component FTC.3. A negative pressure source can comprises a manual device or a power-operated suction device. The tissue closure method includes a manual operating mode using a manual suction device with an automatic shut off for discontinuing suction when a predetermined volume of fluid has been drained. An automatic operating mode utilizes a microprocessor, which can be preprogrammed to respond to various patient and operating conditions. The method proceeds through several phases with different components in place and different patient interface functions occurring in each.

27 Claims, 45 Drawing Sheets

U.S. PATENT DOCUMENTS

| | | |
|---|---|---|
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,245,630 A | 1/1981 | Lloyd et al. |
| 4,248,232 A | 2/1981 | Engelbrecht et al. |
| 4,261,363 A | 4/1981 | Russo |
| 4,275,721 A | 6/1981 | Olson |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A * | 12/1983 | Deaton ............ 604/540 |
| 4,419,097 A | 12/1983 | Rowland |
| 4,475,909 A | 10/1984 | Eisenberg |
| 4,480,638 A * | 11/1984 | Schmid ............ 602/53 |
| 4,525,166 A * | 6/1985 | Leclerc ............ 604/133 |
| 4,540,412 A | 9/1985 | Van Overloop |
| 4,543,100 A | 9/1985 | Brodsky |
| 4,551,139 A | 11/1985 | Plaas et al. |
| 4,569,348 A | 2/1986 | Hasslinger |
| 4,605,339 A | 8/1986 | Bullivant |
| 4,608,041 A | 8/1986 | Nielsen |
| 4,640,688 A | 2/1987 | Hauser |
| 4,655,754 A | 4/1987 | Richmond |
| 4,733,659 A | 3/1988 | Edenbaum |
| 4,743,232 A | 5/1988 | Kruger |
| 4,787,888 A | 11/1988 | Fox |
| 4,826,949 A | 5/1989 | Stanko |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,100,396 A | 3/1992 | Zamierowski |
| 5,112,338 A | 5/1992 | Anspach, III |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| D337,639 S | 7/1993 | Beckman |
| 5,261,893 A | 11/1993 | Zamierowski |
| 5,291,887 A * | 3/1994 | Stanley et al. ............ 600/573 |
| 5,298,015 A | 3/1994 | Komatsuzaki et al. |
| 5,318,570 A | 6/1994 | Hood et al. |
| 5,344,415 A | 9/1994 | Debusk et al. |
| 5,358,494 A | 10/1994 | Svedman |
| 5,437,651 A * | 8/1995 | Todd et al. ............ 604/313 |
| 5,507,833 A | 4/1996 | Bohn |
| 5,522,901 A | 6/1996 | Thomas et al. |
| D372,309 S | 7/1996 | Heldreth |
| 5,556,375 A | 9/1996 | Ewall |
| 5,580,353 A | 12/1996 | Mendes et al. |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Kudein-Meesenburg |
| 5,785,700 A | 7/1998 | Olson |
| 5,800,546 A | 9/1998 | Marik et al. |
| 5,846,244 A | 12/1998 | Cripe |
| 5,911,222 A * | 6/1999 | Lawrence et al. ............ 600/574 |
| 5,921,972 A * | 7/1999 | Skow ............ 604/313 |
| 6,071,267 A * | 6/2000 | Zamierowski ............ 604/289 |
| 6,113,618 A | 9/2000 | Nic |
| 6,126,659 A | 10/2000 | Wack |
| 6,146,423 A | 11/2000 | Cohen et al. |
| 6,159,246 A | 12/2000 | Mendes et al. |
| 6,174,306 B1 * | 1/2001 | Fleischmann ............ 604/543 |
| 6,179,804 B1 * | 1/2001 | Satterfield ............ 604/23 |
| 6,190,391 B1 | 2/2001 | Stubbs |
| 6,190,392 B1 | 2/2001 | Vandewalle et al. |
| RE37,358 E | 9/2001 | Del Rio et al. |
| 6,355,215 B1 | 3/2002 | Poggie et al. |
| 6,377,653 B1 | 4/2002 | Lee et al. |
| 6,398,767 B1 * | 6/2002 | Fleischmann ............ 604/513 |
| 6,430,427 B1 | 8/2002 | Lee et al. |
| 6,500,209 B1 | 12/2002 | Kolb |
| 6,503,281 B1 | 1/2003 | Mallory |
| 6,626,891 B2 * | 9/2003 | Ohmstede ............ 604/543 |
| 6,685,681 B2 * | 2/2004 | Lockwood et al. ............ 604/305 |
| 6,695,823 B1 * | 2/2004 | Lina et al. ............ 604/304 |
| 6,752,794 B2 * | 6/2004 | Lockwood et al. ............ 604/313 |
| 6,800,074 B2 * | 10/2004 | Henley et al. ............ 604/319 |
| 2002/0099447 A1 | 7/2002 | Mears et al. |
| 2002/0116067 A1 | 8/2002 | Mears et al. |
| 2002/0183565 A1 | 12/2002 | Ansmann |
| 2003/0050594 A1 * | 3/2003 | Zamierowski ............ 604/46 |
| 2003/0097135 A1 | 5/2003 | Penenberg |
| 2004/0039415 A1 * | 2/2004 | Zamierowski ............ 606/215 |

\* cited by examiner

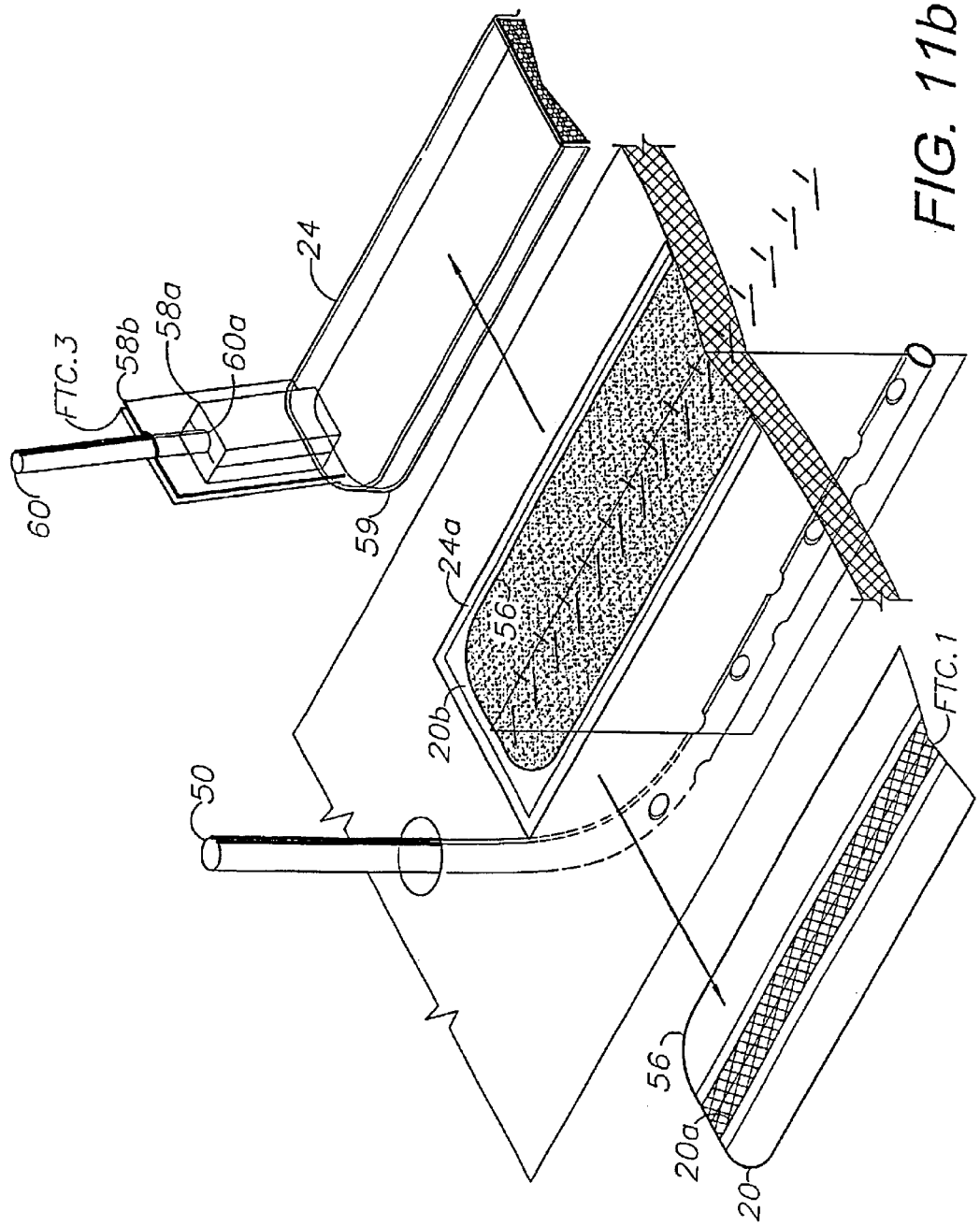

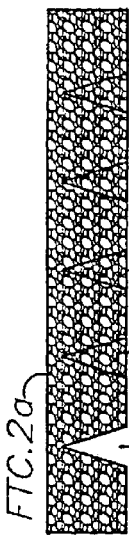
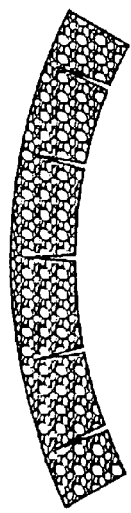
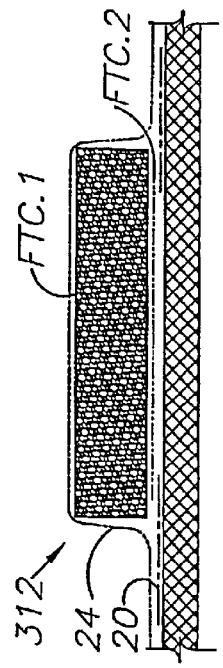
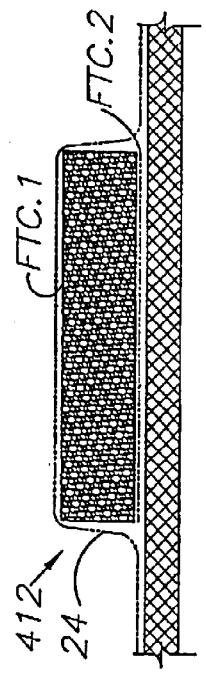
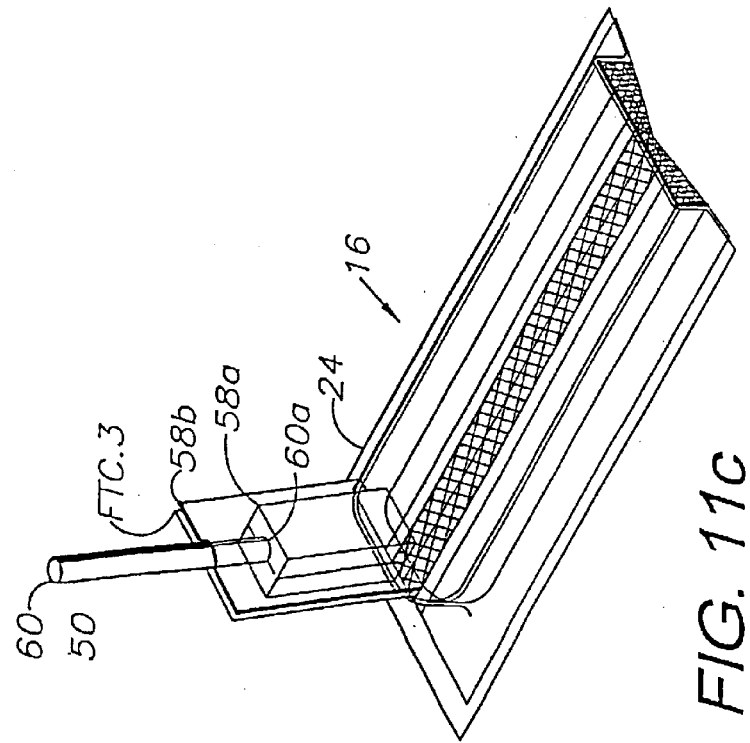

TISSUE CLOSURE TREATMENT SYSTEM, PATIENT INTERFACE AND METHOD

CROSS-REFERENCE TO RELATED APPLICATION

Continuation-in-part of U.S. patent application Ser. No. 10/334,766, filed Dec. 31, 2002.

BACKGROUND OF THE INVENTION

1. Field of the Invention

The present invention relates generally to medical devices and methods for treating closed wounds and incisions, and in particular to a system and method for draining and/or irrigating tissue separations, such as surgical incisions, and for compressing and stabilizing a dissected or traumatized field with ambient air pressure created by an external patient interface component and a vacuum source.

2. Description of the Related Art

Tissue separations can result from surgical procedures and other causes, such as traumatic and chronic wounds. Various medical procedures are employed to close tissue separations. An important consideration relates to securing separate tissue portions together in order to promote closure and healing. Incisions and wounds can be closed with sutures, staples and other medical closure devices. The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation long enough for collagen deposition to take place to unite the separated parts.

Other important considerations include controlling bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues and adhesive tape strips. However, deeper incisions may well require not only skin surface closure, but also time-consuming placement of multiple layers of sutures in the load-bearing planes.

Infection prevention is another important consideration. Localized treatments include various antibiotics and dressings, which control or prevent bacteria at the incision or wound site. Infections can also be treated and controlled systemically with suitable antibiotics and other pharmacologics.

Other tissue-separation treatment objectives include minimizing the traumatic and scarring effects of surgery and minimizing edema. Accordingly, various closure techniques, postoperative procedures and pharmacologics are used to reduce postoperative swelling, bleeding, seroma, infection and other undesirable, postoperative side effects. Because separated tissue considerations are so prevalent in the medical field, including most surgeries, effective, expedient, infection-free and aesthetic tissue closure is highly desirable from the standpoint of both patients and health-care practitioners. The system, interface and method of the present invention can thus be widely practiced and potentially provide widespread benefits to many patients.

Fluid control considerations are typically involved in treating tissue separations. For example, subcutaneous bleeding occurs at the fascia and muscle layers in surgical incisions. Accordingly, deep drain tubes are commonly installed for the purpose of draining such incisions. Autotransfusion has experienced increasing popularity in recent years as equipment and techniques for reinfusing patients' whole blood have advanced considerably. Such procedures have the advantage of reducing dependence on blood donations and their inherent risks. Serous fluids are also typically exuded from incision and wound sites and require drainage and disposal. Fresh incisions and wounds typically exude blood and other fluids at the patient's skin surface for several days during initial healing, particularly along the stitch and staple lines along which the separated tissue portions are closed.

Another area of fluid control relates to irrigation. Various irrigants are supplied to separated tissue areas for countering infection, anesthetizing, introducing growth factors and otherwise promoting healing. An effective fluid control system preferably accommodates both draining and irrigating functions sequentially or simultaneously.

Common orthopedic surgical procedures include total joint replacements (TJRs) of the hip, knee, elbow, shoulder, foot and other joints. The resulting tissue separations are often subjected to flexure and movement associated with the articulation of the replacement joints. Although the joints can be immobilized as a treatment option, atrophy and stiffness tend to set in and prolong the rehabilitation period. A better option is to restore joint functions as soon as possible. Thus, an important objective of orthopedic surgery relates to promptly restoring to patients the maximum use of their limbs with maximum ranges of movement.

Similar considerations arise in connection with various other medical procedures. For example, arthrotomy, reconstructive and cosmetic procedures, including flaps and scar revisions, also require tissue closures and are often subjected to movement and stretching. Other examples include incisions and wounds in areas of thick or unstable subcutaneous tissue, where splinting of skin and subcutaneous tissue might reduce dehiscence of deep sutures. The demands of mobilizing the extremity and the entire patient conflict with the restrictions of currently available methods of external compression and tissue stabilization. For example, various types of bandage wraps and compressive hosiery are commonly used for these purposes, but none provides the advantages and benefits of the present invention The aforementioned procedures, as well as a number of other applications discussed below, can benefit from a tissue-closure treatment system and method with a surface-applied patient interface for fluid control and external compression.

Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. No. 4,969,880; No. 5,100,396; No. 5,261,893; No. 5,527,293; and No. 6,071,267 disclose the use of pressure gradients, i.e., vacuum and positive pressure, to assist with fluid drainage from wounds, including surgical incision sites. Such pressure gradients can be established by applying porous sponge material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing.

Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external, open-wound vacuum devices applied to the wound surface. Fixation of tissues in apposition can also be achieved by bolus tie-over dressings (Stent dressings), taping, strapping and (contact) casting.

Heretofore there has not been available a tissue closure system, patient interface and method with the advantages and features of the present invention.

SUMMARY OF THE INVENTION

In the practice of the present invention, a system and method are provided for enhancing closure of separated tissue portions using a surface-applied patient interface. Subsurface drainage, irrigation and autotransfusion components can optionally be used in conjunction with the surface-applied, external interface. The external interface can be advantageously placed over a stitch or staple line and includes a primary transfer component comprising a strip of porous material, such as rayon, applied directly to the patient for wicking or transferring fluid to a secondary transfer component comprising a sponge or foam material. An underdrape is placed between the transfer elements for passing fluid therebetween through an underdrape opening, such as a slot. An overdrape is placed over the secondary transfer component and the surrounding skin surface. The patient interface is connected to a negative pressure source, such as a vacuum assisted closure device, wall suction or a mechanical suction pump. A manual control embodiment utilizes a finite capacity fluid reservoir with a shut-off valve for discontinuing drainage when a predetermined amount of fluid is collected. An automatic control embodiment utilizes a microprocessor, which is adapted for programming to respond to various inputs in controlling the operation of the negative pressure source. A closed wound or incision treatment method of the present invention involves three phases of fluid control activity, which correspond to different stages of the healing process. In a first phase active drainage is handled. In a second phase components can be independently or sequentially disengaged. In a third phase the secondary transfer component can optionally be left in place for protection and to aid in evacuating any residual fluid from the suture/staple line through the primary transfer component.

In other embodiments of the invention, components of the dressing system can be premanufactured for efficient application. A foam piece can be provided with a full or partial rayon cover and a close-fitting overdrape. An access panel with a reclosable seal strip can be installed on the overdrape for access to the foam pieces and the wound area. A premanufactured external dressing can be provided with a sheath receiving a foam piece, which is accessible through a reclosable seal strip for replacement or reorientation. Treatment area access is also provided through the seal strip.

BRIEF DESCRIPTION OF THE DRAWINGS

The drawings constitute a part of this specification and include exemplary embodiments of the present invention and illustrate various objects and features thereof.

FIGS. 12e,f show a modified FTC.2a with removable wedges to facilitate articulation, such as flexure of a patient joint.

FIGS. 12g,h show alternative embodiment external patient interface assemblies.

DETAILED DESCRIPTION OF THE PREFERRED EMBODIMENT

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Tissue Closure System 2

Figure 1:
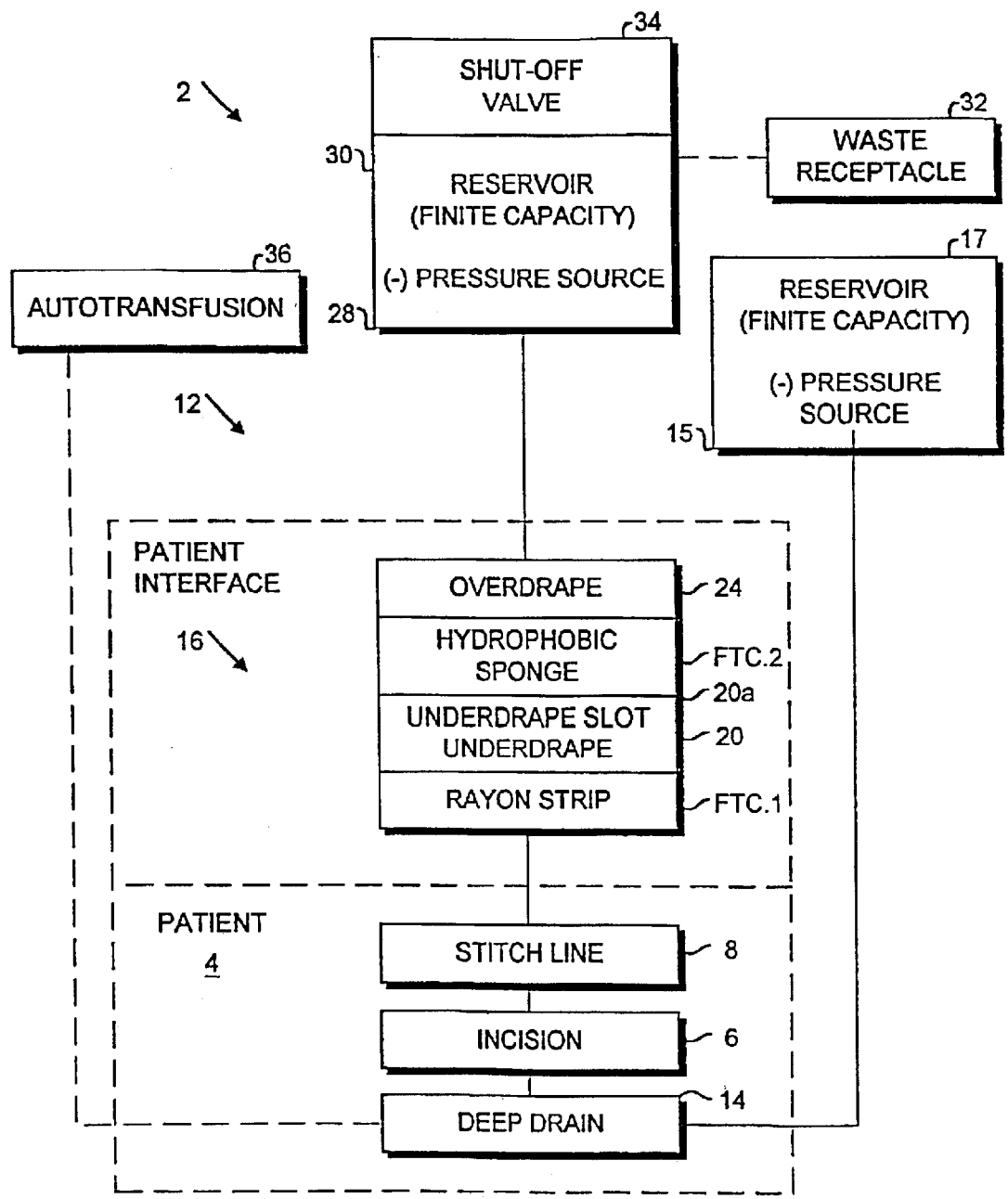
FIG. 1 is a schematic, block diagram of a tissue closure treatment and system embodying the present invention.

Referring to the drawings in more detail, the reference numeral 2 generally designates a tissue closure treatment system embodying the present invention. As shown in FIG. 1, the system 2 is adapted for use on a patient 4 with an incision or wound 6, which can be closed by a stitch line 8 consisting of sutures 10, staples or other suitable medical fasteners.

A patient interface 12 consists of an optional deep drain 14 connected to a deep drain negative pressure source 15 associated with a deep drainage reservoir 17 and an external patient interface 16 including a primary fluid transfer component FTC.1 comprising a strip of rayon or other suitable porous material, an underdrape 20 generally covering FTC.1 and including a slot 20a, a secondary fluid transfer component FTC.2 comprising a hydrophobic sponge and an overdrape 24.

A fluid handling subsystem 26 includes the deep drain negative pressure source 15 and a surface drain negative pressure source 28, which can be combined for applications where a common negative pressure source and a collection receptacle are preferred. The negative pressure sources 15, 28 can operate either manually or under power. Examples of both types are well-known in the medical art. For example, a manually operable portable vacuum source (MOPVS) is shown in U.S. Pat. No. 3,115,138, which is incorporated herein by reference. The MOPVS is available from Zimmer, Inc. of Dover, Ohio under the trademark HEMOVAC®. Bulb-type actuators, such as that shown in U.S. Pat. No. 4,828,546 (incorporated herein by reference) and available from Surgidyne, Inc. of Eden Prairie, Minn., can be used on smaller wounds, for shorter durations or in multiples. Moreover, power-actuated vacuum can be provided by vacuum assisted closure equipment available under the trademark THE VAC® from Kinetic Concepts, Inc. of San Antonio, Tex. Still further, many health-care facilities, particularly hospitals and clinics, are equipped with suction systems with sources of suction available at wall-mounted outlets.

A finite capacity reservoir 30 is fluidically connected to the negative pressure source 28 and is adapted to discharge to a waste receptacle 32. A shut-off valve 34 is associated with the reservoir 30 and is adapted to automatically discontinue drainage when the reservoir 30 is filled to a predetermined volume.

An optional autotransfusion subsystem 36 can be connected to the deep drain 14 and is adapted for reinfusing the patient 4 with his or her own blood. U.S. Pat. No. 5,785,700 discloses such an autotransfusion system with a portable detachable vacuum source, which is available from Zimmer, Inc. and is incorporated herein by reference.

Figure 2:
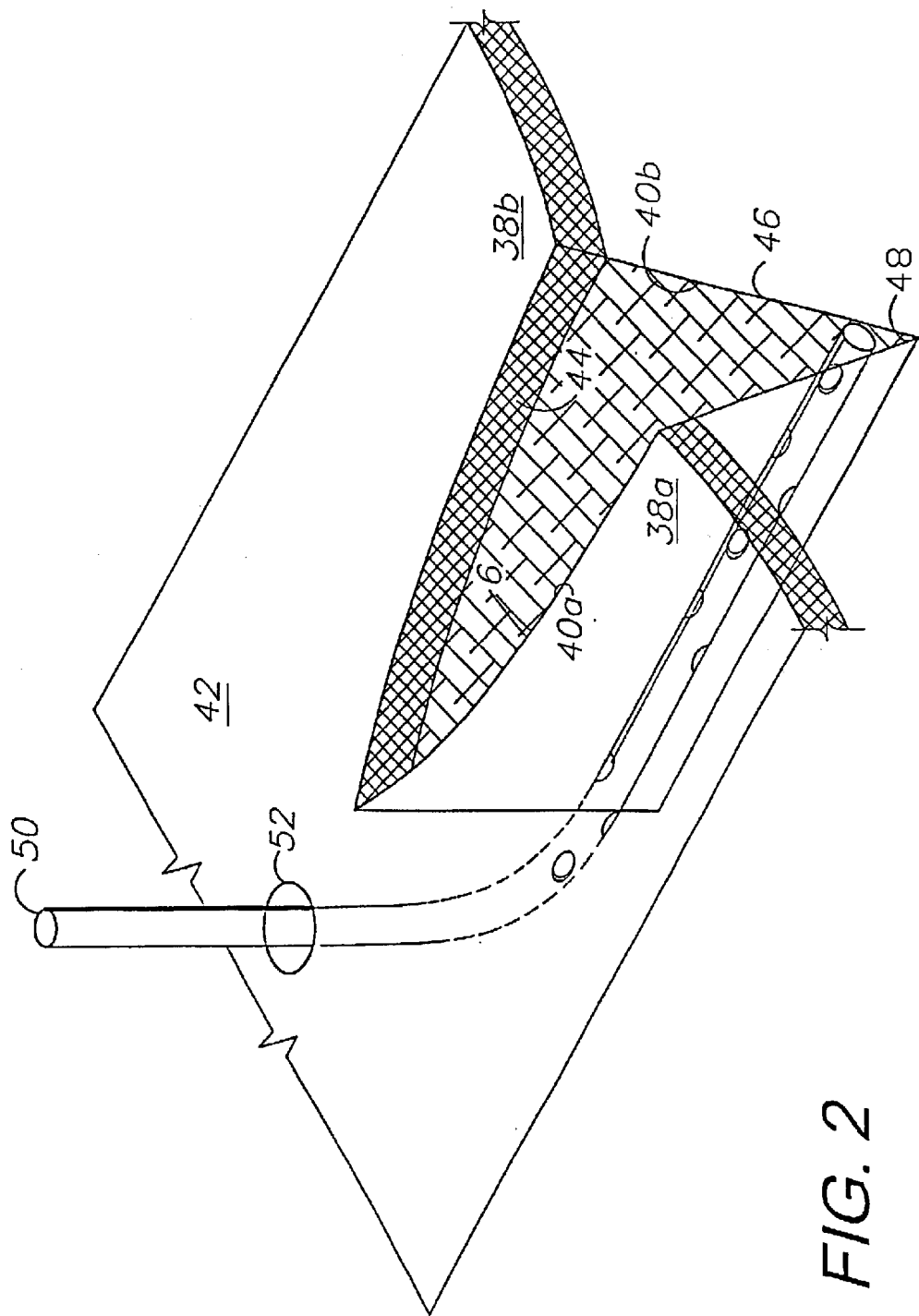
FIG. 2 is a perspective view of an incision tissue separation with a deep drain tube installed.

FIG. 2 shows an incision 6 forming first and second separated tissue portions 38a,b with incision edges 40a,b. The incision 6 extends from and is open at the skin 42, through the deep dermal layer 44 and the subcutaneous layer 46, to approximately the fascia 48. A deep drain tube 50 is placed in a lower part of the incision 6 and penetrates the skin 42 at an opening 52.

Figure 3:
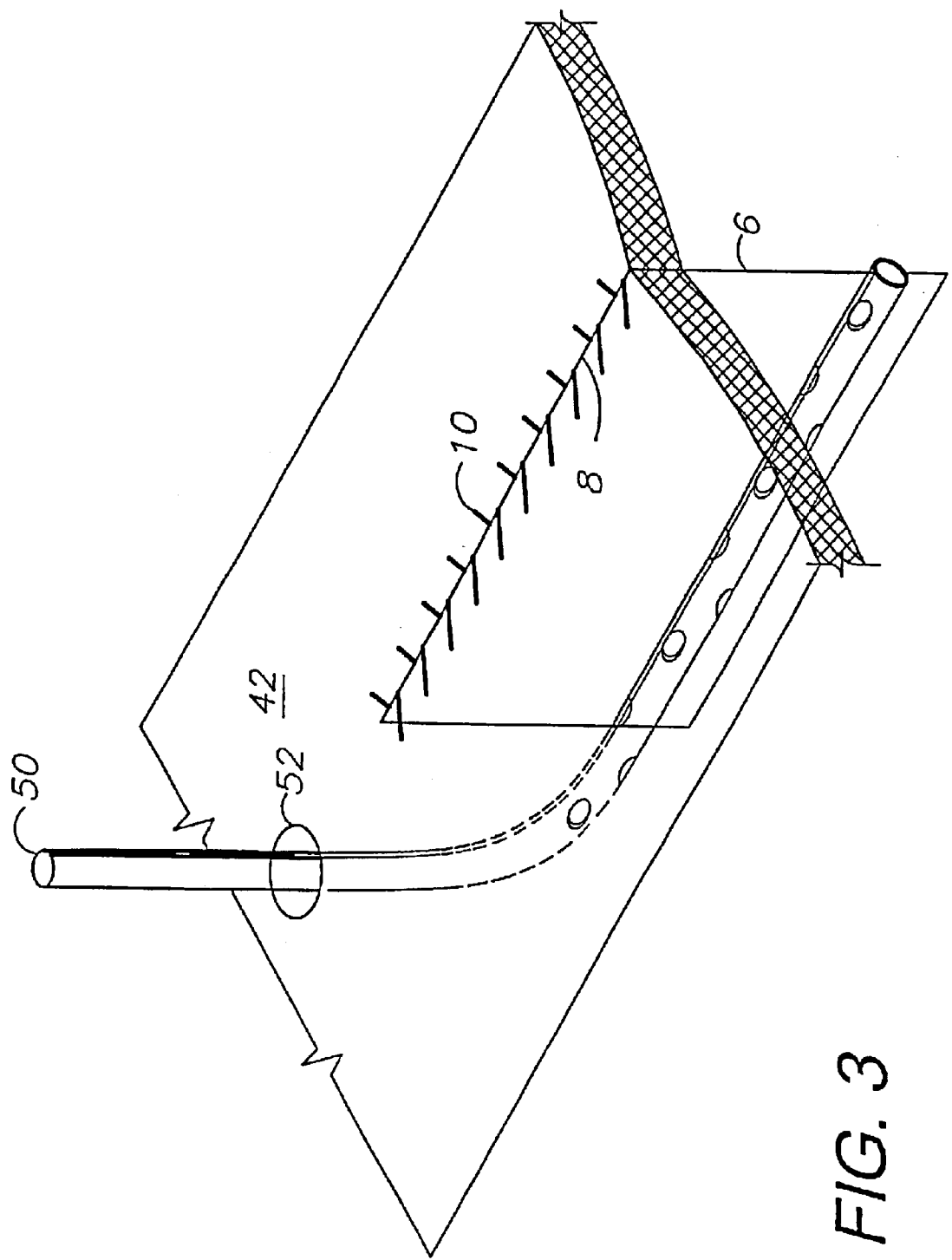
FIG. 3 is a perspective view thereof, showing the separated tissue sutured together at the skin.
Figure 4:
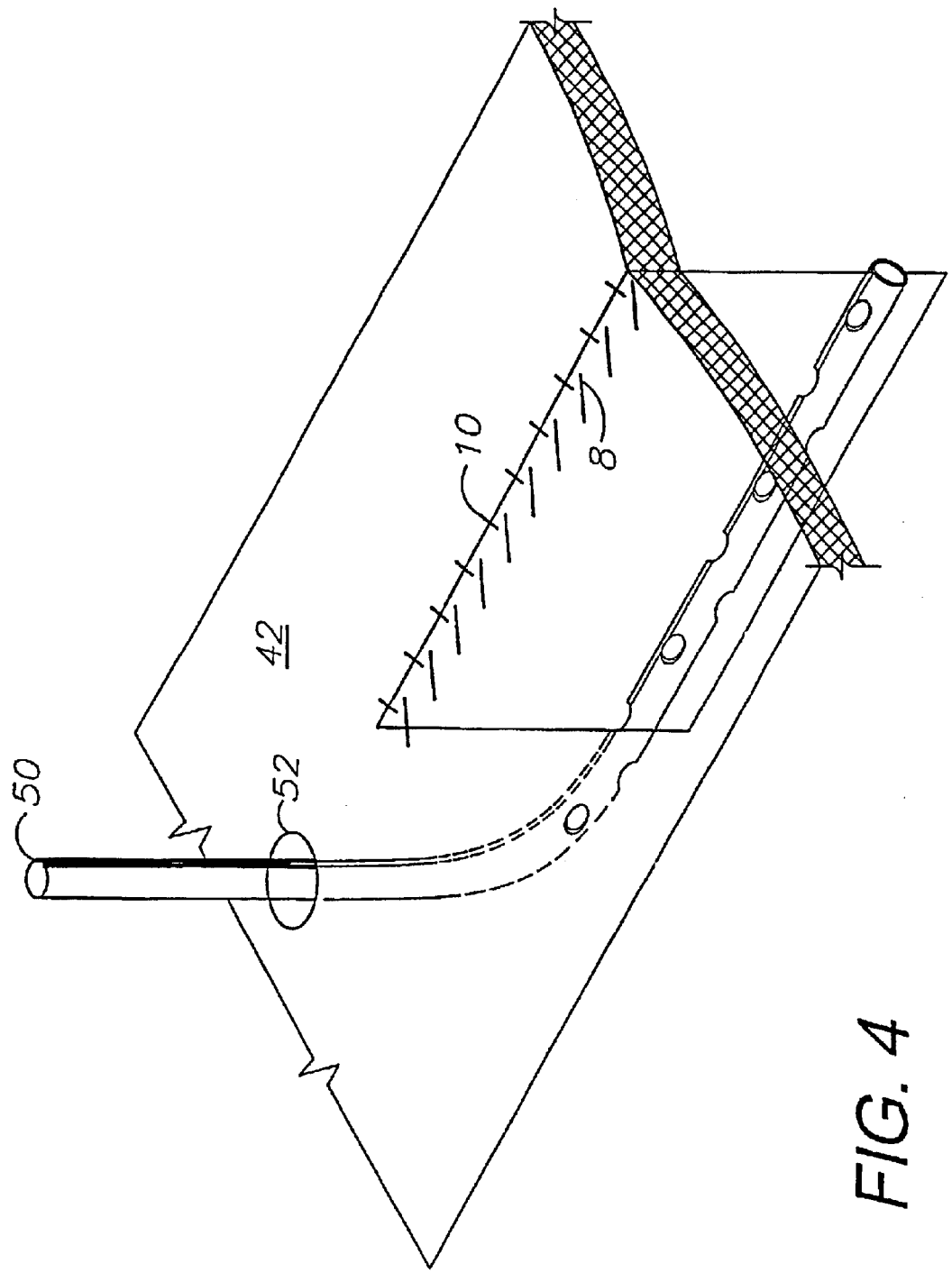
FIG. 4 is a perspective view thereof, showing the separated tissue sutured together at the deep dermal layer below the skin surface.

FIG. 3 shows the incision edges 40a,b secured together by sutures 54 forming a stitch line 56 at the skin surface 42. As an alternative to sutures 54, various other medical fasteners, such as staples, can be used. FIG. 4 shows sutures 55 placed in the deep dermal layer 44 below the skin surface 42.

Figure 5:
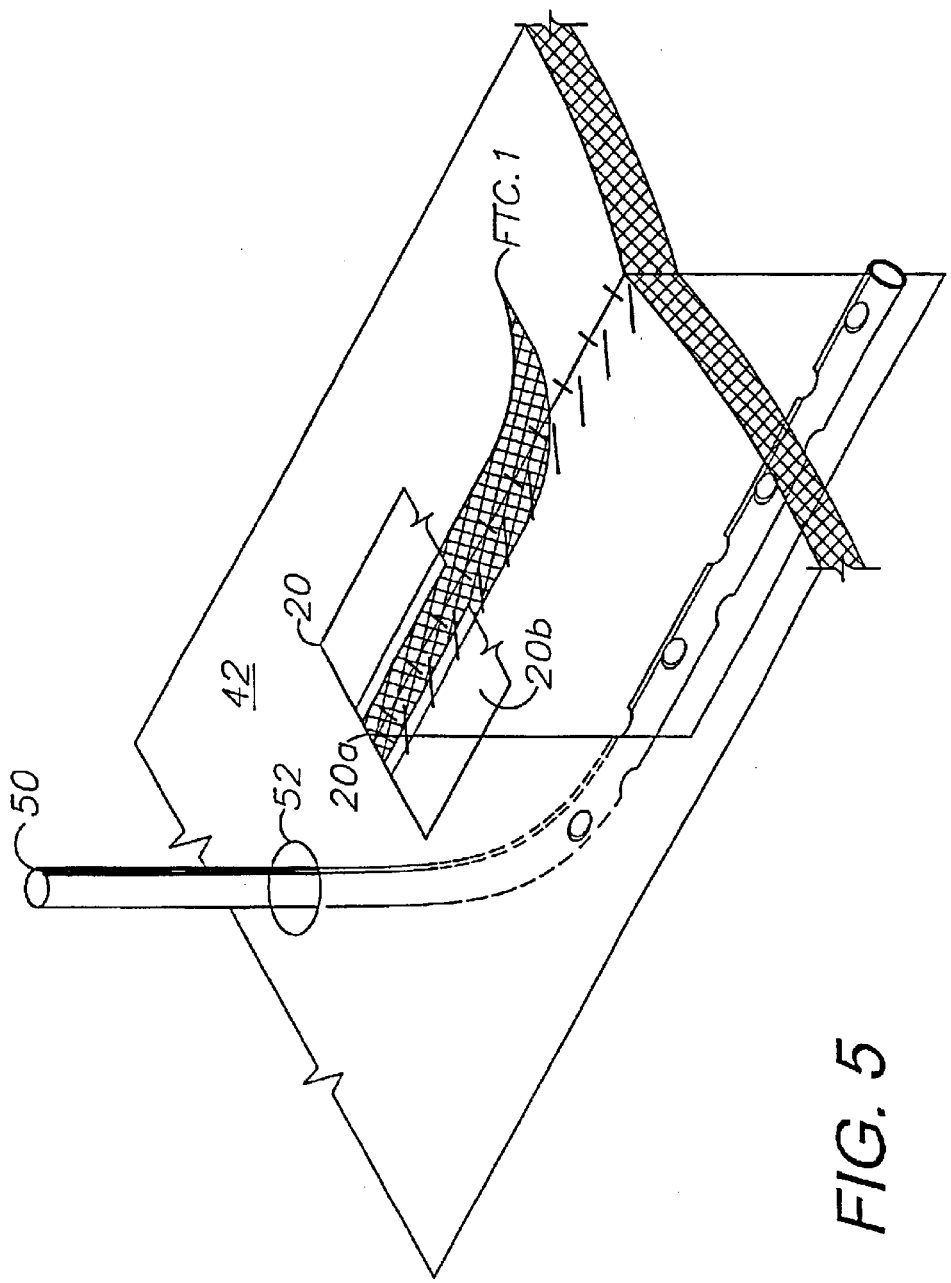
FIG. 5 is a perspective view thereof, showing a rayon strip primary fluid transfer component (FTC.1) and an underdrape being placed on the stitch line.
Figure 6:
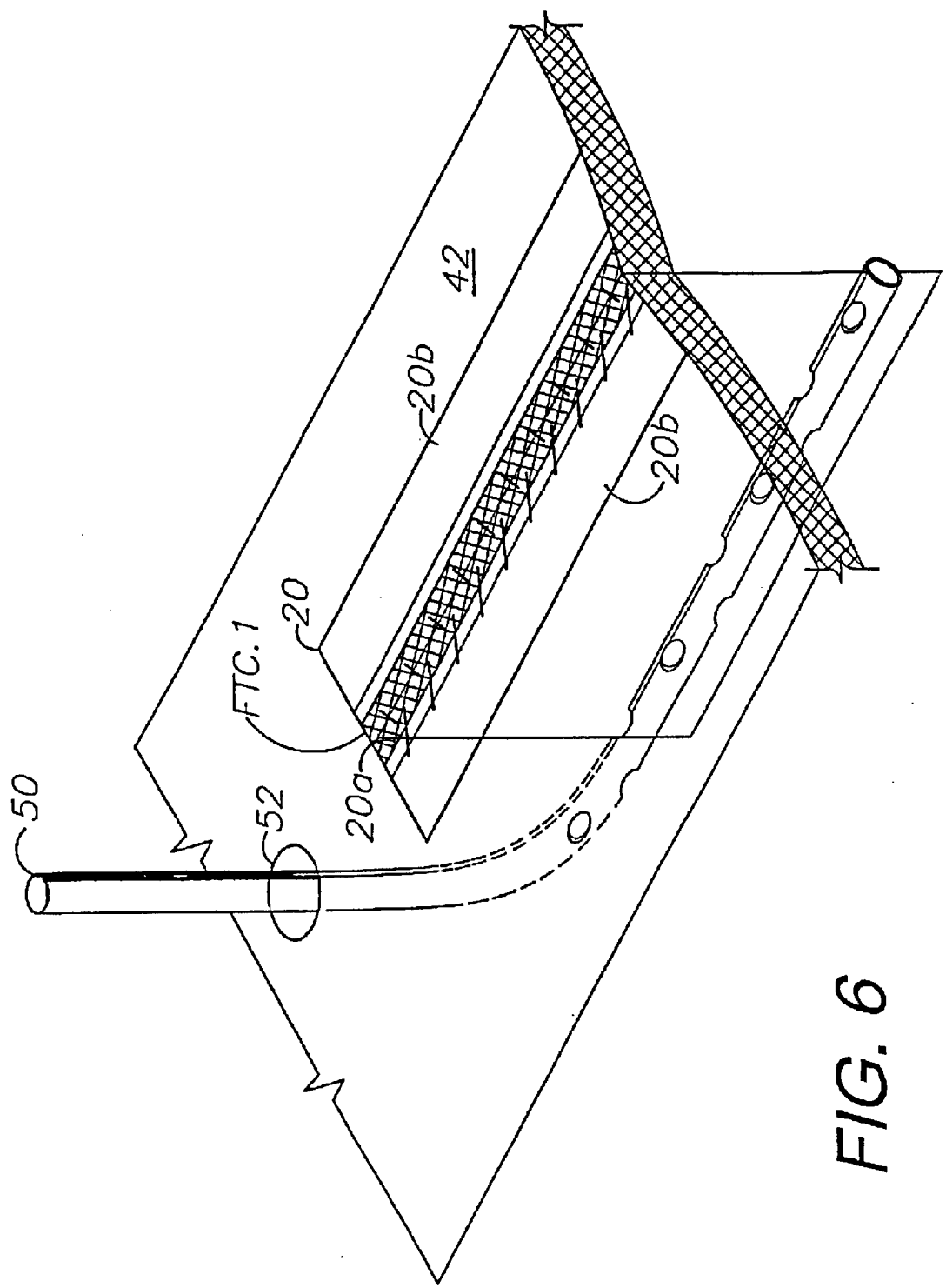
FIG. 6 is a perspective view thereof, showing FTC.1 and the underdrape in place on the stitch line.

FIG. 5 shows application of FTC.1 on top of the stitch line 8. FTC.1 preferably comprises a suitable porous wicking material, such as rayon, which is well-suited for wicking the fluid that exudes along the stitch line 8. Rayon also tends to dry relatively quickly, and thus efficiently transfers fluid therethrough. The underdrape 20 is placed over FTC.1 and the adjacent skin surface 42. Its slot 20a is generally centered along the centerline of FTC.1 and directly above the stitch line 8. FTC.1 and the underdrape 20 can be preassembled in a roll or some other suitable configuration adapted to facilitate placement on the stitch line 8 in any desired length. FIG. 6 shows FTC. 1 and the underdrape 20 in place.

Figure 7:
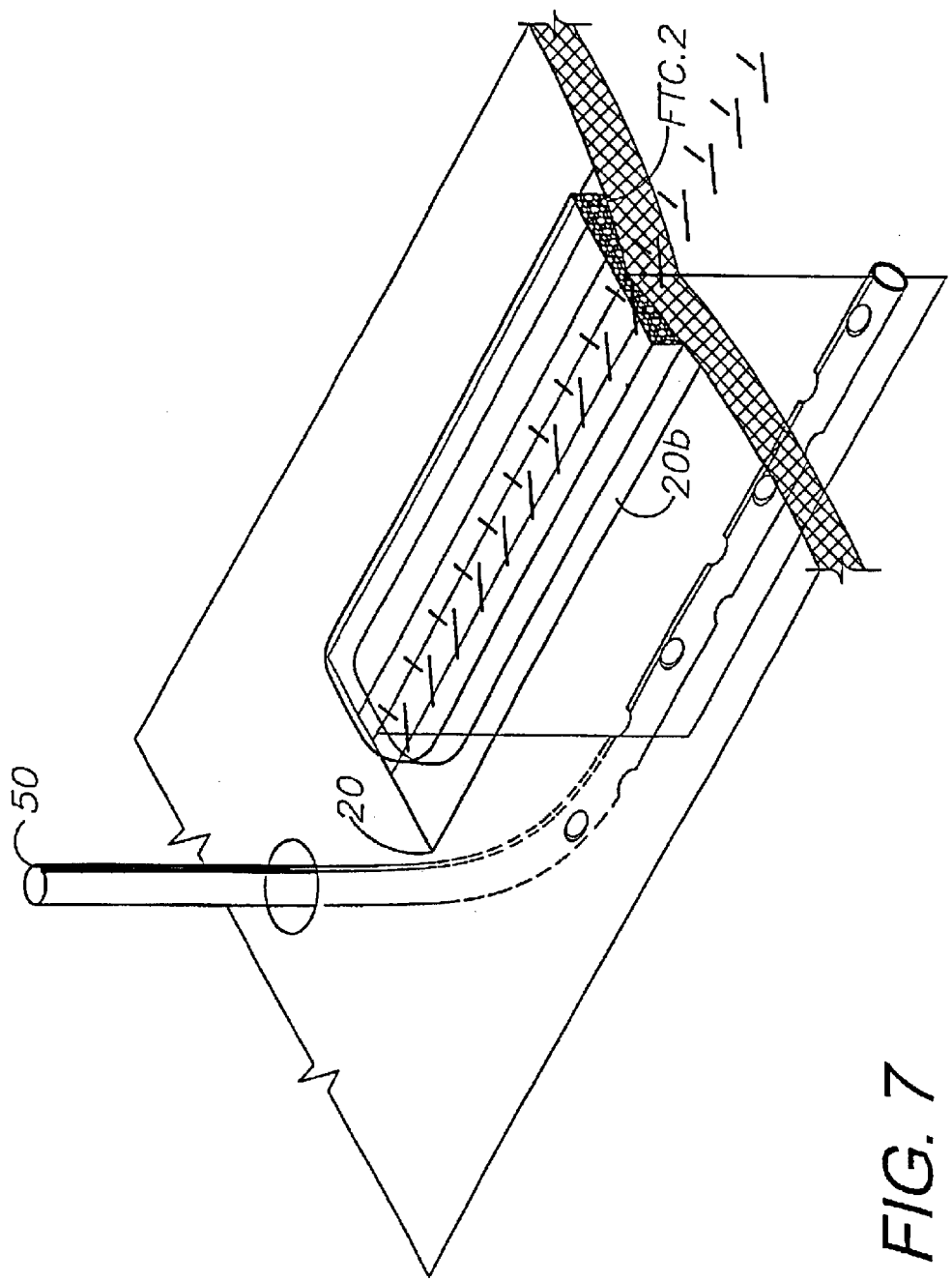
FIG. 7 is a perspective view thereof, showing a secondary fluid transfer component (FTC.2) in place.

The secondary fluid transfer component FTC.2 is shown installed in FIG. 7. It preferably comprises a suitable hydrophobic foam material, such as polyurethane ether (PUE), which comprises a reticulated, lattice-like (foam) material capable of being collapsed by vacuum force (negative pressure) in order to exert positive "shrink-wrap" type compression on skin surface and still maintain channels that allow passage of fluid. As shown, its footprint is slightly smaller than that of the underdrape 20, thus providing an underdrape margin 20b. The wicking layer of FTC.1 can, as an alternative, be sized equal to or almost equal to the footprint of FTC.2. This configuration lends itself to prefabrication as an individual, pre-assembled pad that can be employed by simply removing a releasing layer backing from an adhesive lined underdrape. This configuration also lends itself to easy total removal and replacement of the central part of the assembly without removing drape already adhered to skin if removal and replacement is the desired clinical option rather then staged removal or prolonged single application.

Figure 8:
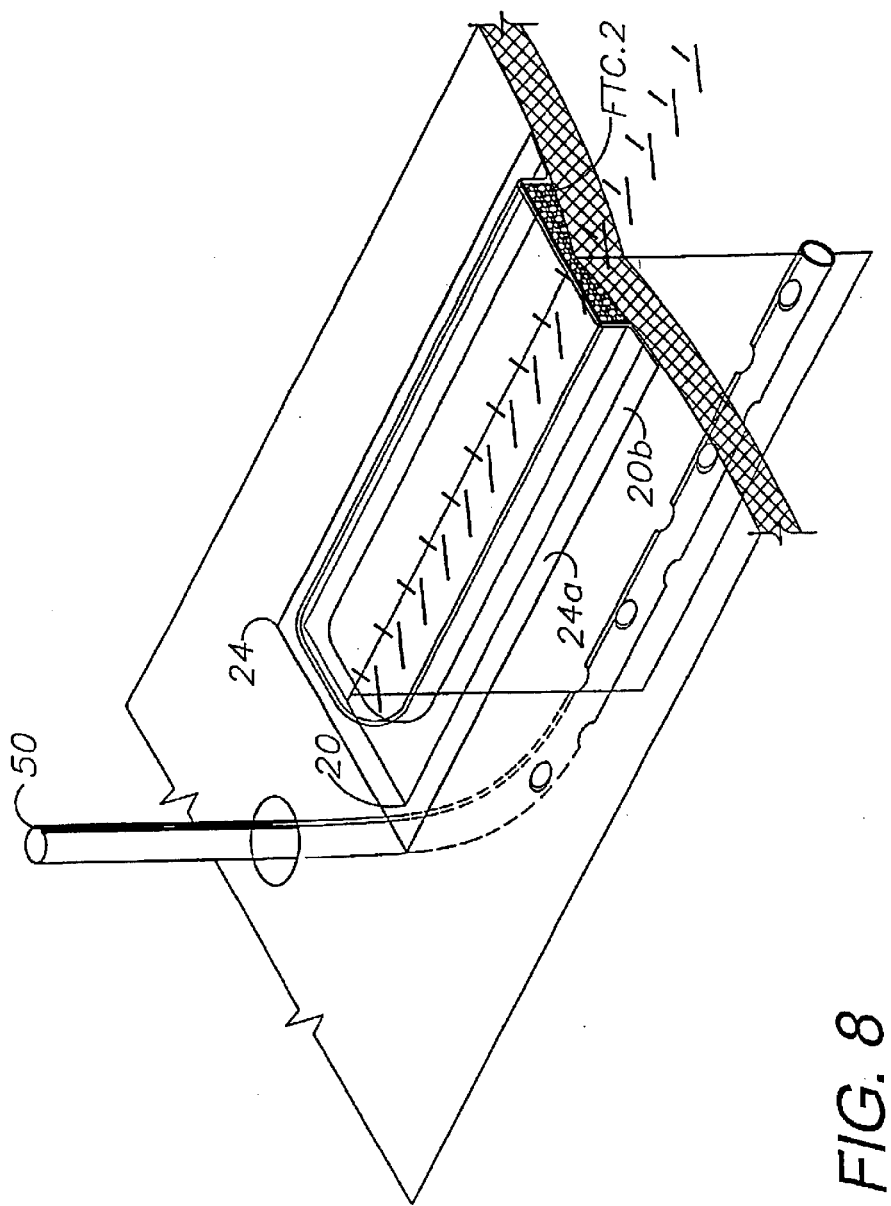
FIG. 8 is a perspective view thereof, showing an overdrape in place.
Figure 9:
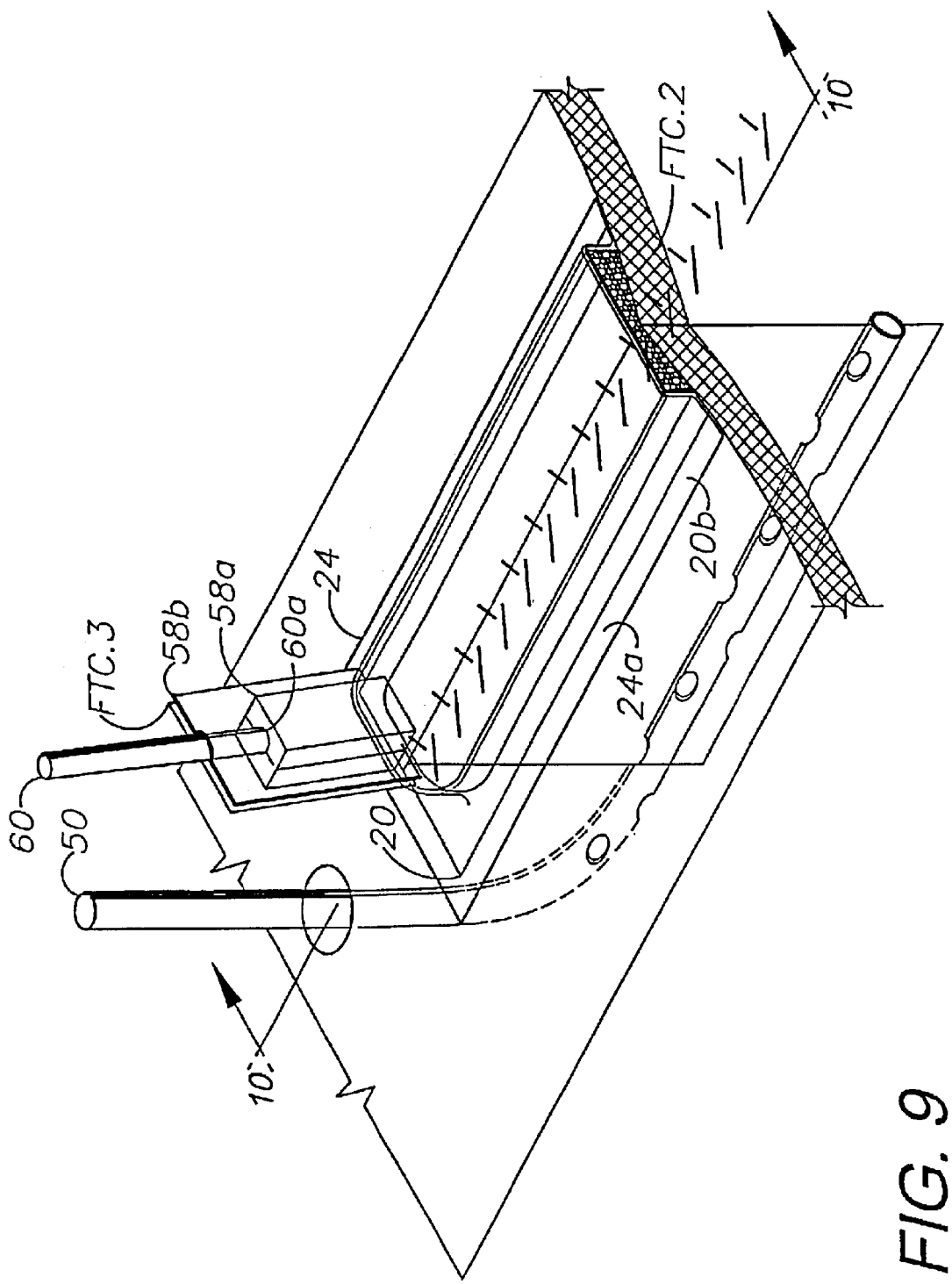
FIG. 9 is a perspective view thereof, showing a connecting fluid transfer component (FTC.3) in place for connecting the system to a negative pressure source.
Figure 10:
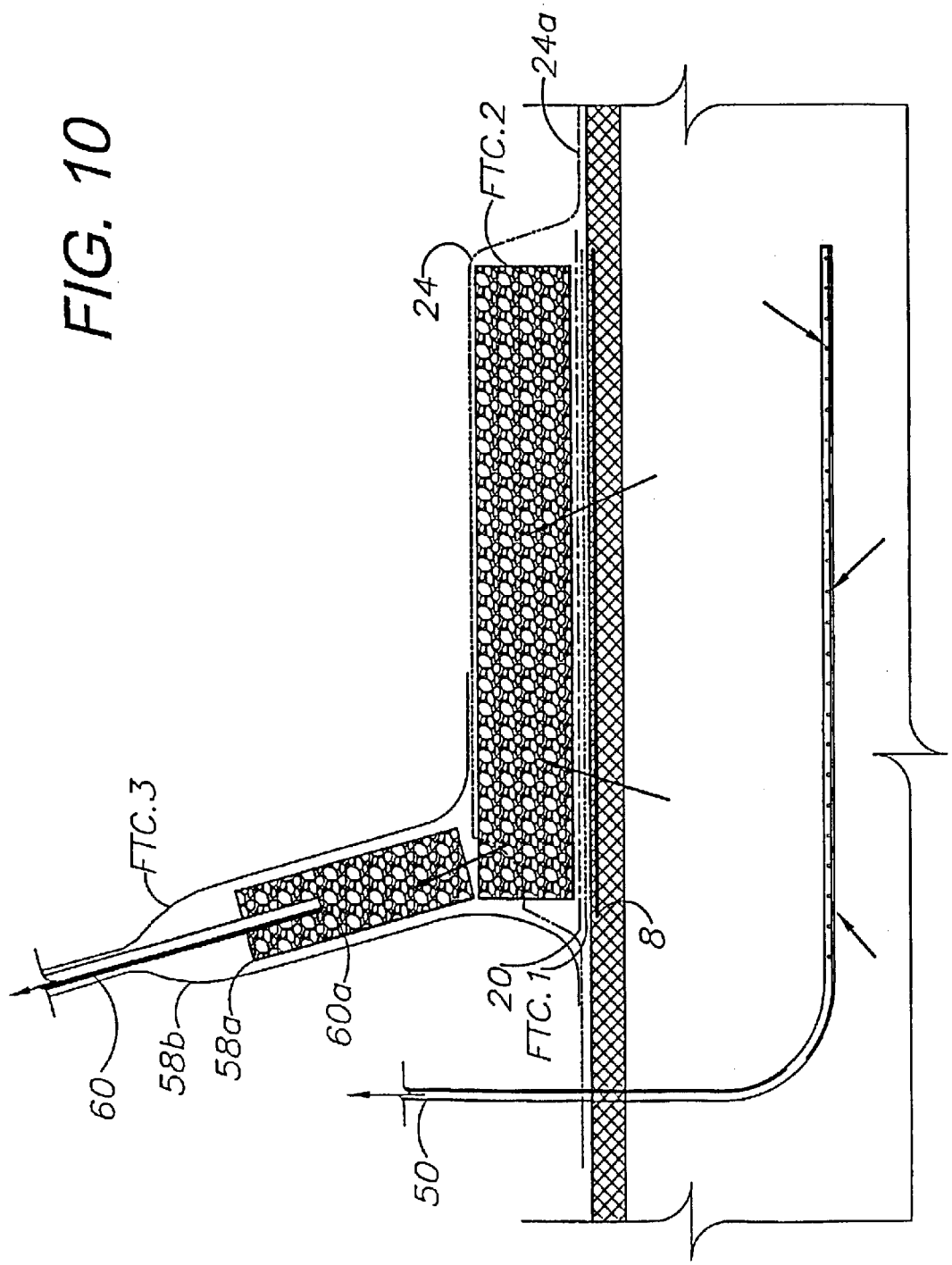
FIG. 10 is a cross-sectional view thereof, taken generally along line 10—10 in FIG. 9 and particularly showing FTC.3.

FIG. 8 shows the overdrape 24 applied over FTC.2 and the underdrape 20, with a margin 24a extending beyond the underdrape margin 22b and contacting the patient's skin surface (dermis) 42. FIGS. 9 and 10 show a patch connector 58 mounted on FTC.2 and comprising a hydrophobic foam (PUE) material core 58a sandwiched between drape layers 58b. A vacuum drain tube 60 includes an inlet end 60a embedded in the foam core 58a and extends between the drape layers 58b to an outlet end 60b connected to the surface drainage negative pressure source 28.

Figure 11:
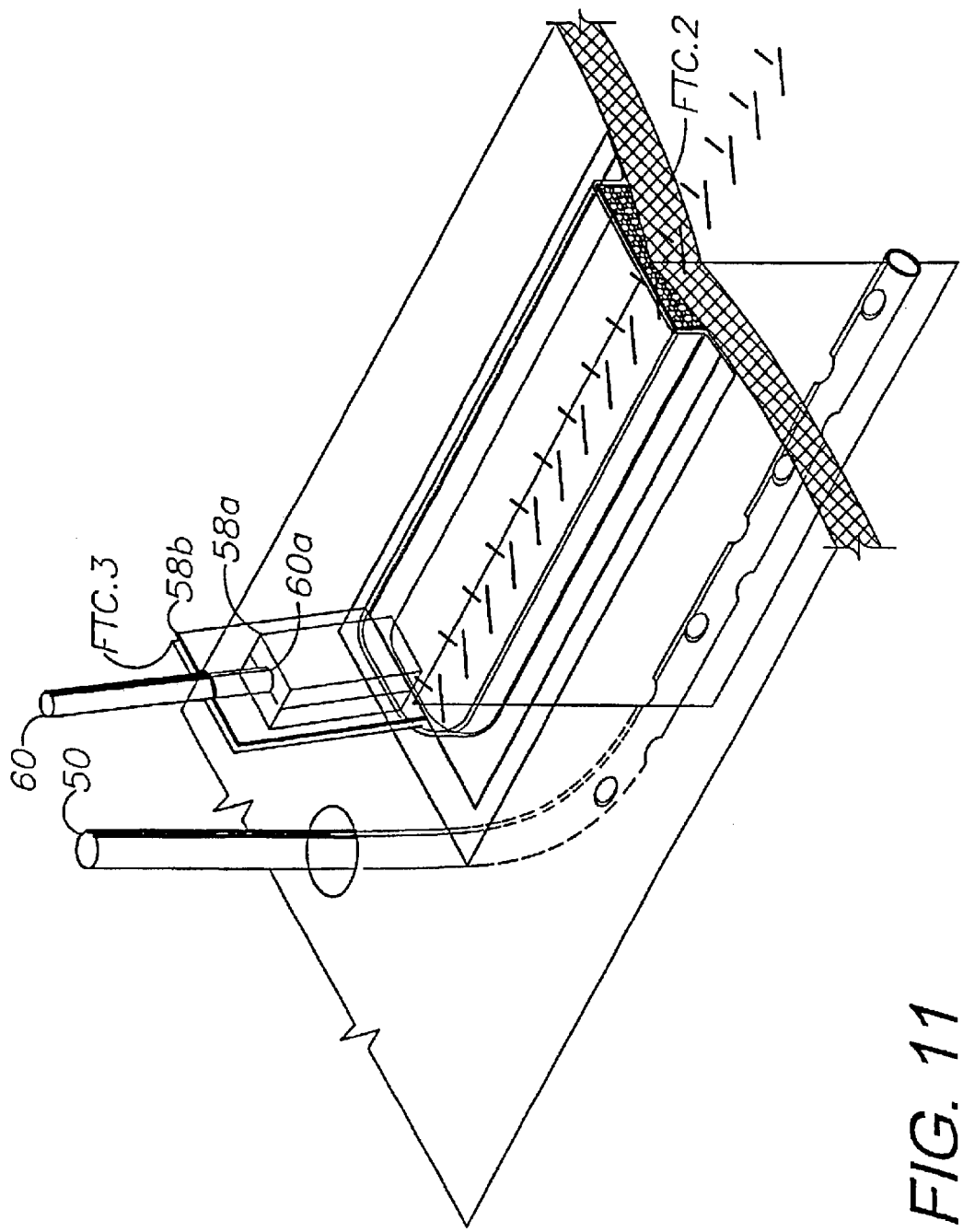
FIG. 11a is a perspective view thereof, showing FTC.3 removed and the overdrape scored for ventilation.
FIG. 11b is a perspective view thereof, showing the patient interface removed along a perforated tear line in the underdrape and a slit line in the overdrape.
FIG. 11c is a perspective view of a patient interface adapted for prepackaging, application to a patient and connection to a negative pressure source.
Figure 11A:
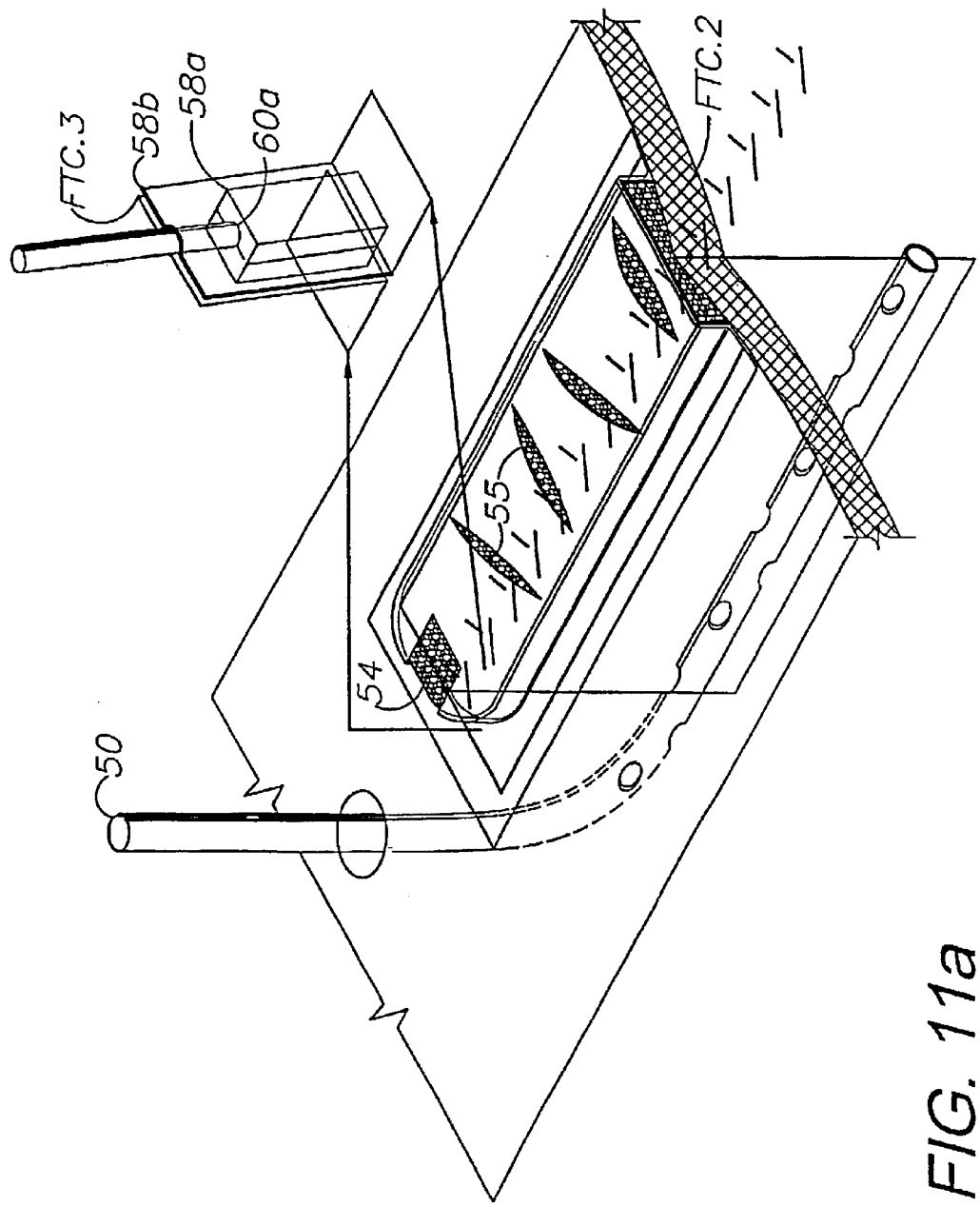
Figure 12B:
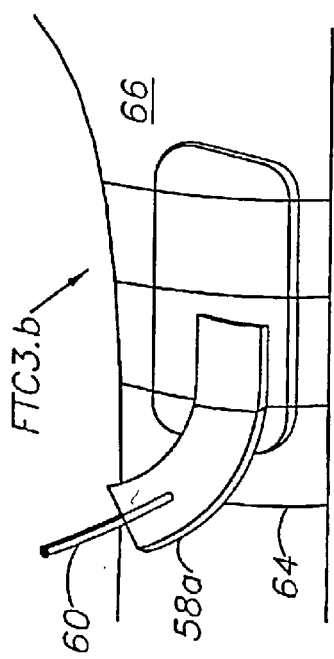
FIGS. 12a–d show alternative embodiment elbow connecting devices FTC.3a–d respectively.
Figure 12D:
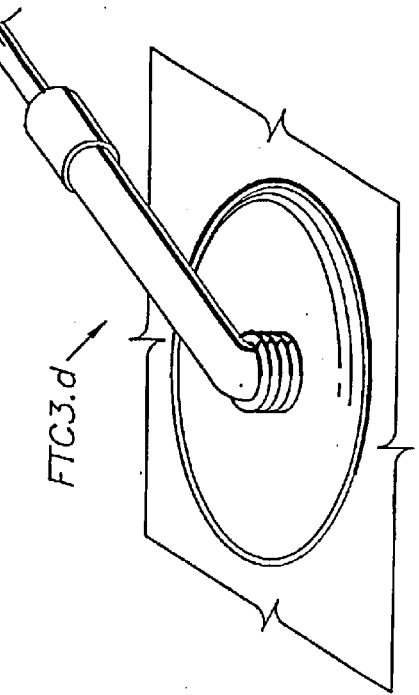
Figure 12A:
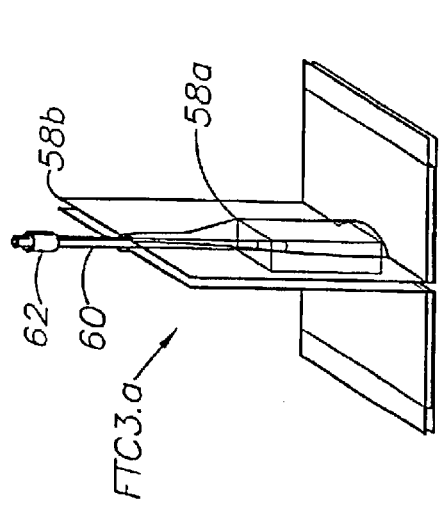
Figure 12C:
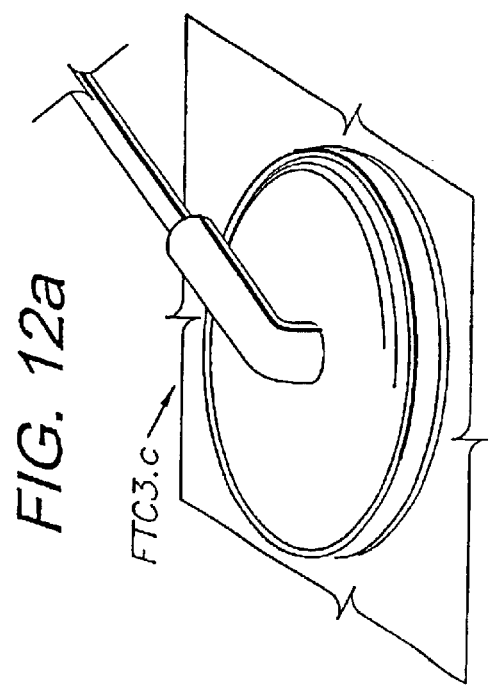

FIG. 11a shows FTC.3 removed, e.g. by cutting away portions of the overdrape 24 to provide an overdrape opening 54. In addition, the overdrape 24 can be slit at 55 to further ventilate FTC.2. Draining FTC.2 under negative pressure, and further drying it with air circulation (FIG. 11a) can provide significant healing advantages by reducing the growth of various microbes requiring moist environments in FTC.2. Such microbes and various toxins produced thereby can thus be evaporated, neutralized and otherwise prevented from reentering the patient. Microbe control can also be accomplished by introducing antiseptics in and irrigating various components of the patient interface 12, including the drapes 20, 24; FTC.1; FTC.2; and FTC.3.

FIG. 11b shows the patient interface 12 removed along underdrape perforated tear lines 56 and slit lines 59 in overdrape 24. It will be appreciated that substantially the entire patient interface 12, except for underdrape and overdrape margins 20b, 24a can thus be removed to provide access to the stitch line 8 and the dermis 42 for visual inspection, evaluation, cleaning, stitch removal, dressing change (e.g., with prepackaged patient interface 12a as shown in FIG. 11c), consideration of further treatment options, etc. For example, the overdrape 24 can be slit to around the perimeter or footprint of FTC.2 to permit removing the same. Preferably FTC.2 is easily releasable from the underdrape 20 and FTC.1 whereby FTC.2 can be grasped and lifted upwardly to facilitate running a scalpel through the overdrape 24 and into a separation between the underside of FTC.2 and the underdrape 20. The FTC.1 can then optionally be removed by tearing the underdrape 20 along its tear lines 56 and removing same as shown in FIG. 11b.

FIG. 11c shows a prepackaged patient interface 12a adapted for initial or "dressing change" application. Optionally, the rayon strip FTC.1 can have the same configuration or "footprint" as the foam sponge FTC.2, thus eliminating the underdrape 20. The prepackaged patient interface 12a can be sterilely packaged to facilitate placement directly on a stitch line 8. Alternatively, the patient interface components can be prepackaged individually or in suitable groups comprising subassemblies of the complete patient interface 12. For example, the underdrape/FTC.1 and the overdrape/FTC.2 subassemblies respectively can be prepackaged individually. Various sizes and component configurations of the patient interface can be prepackaged for application as indicated by particular patient conditions. Preferably, certain sizes and configurations would tend to be relatively "universal" and thus applicable to particular medical procedures, such as TJRs, whereby patient interface inventory can be simplified. Alternatively, the individual components can be assembled in various sizes and configurations for "custom" applications.

FIGS. 12a–d show alternative connecting fluid transfer components FTC.3a–d for connecting FTC.2 to the surface drainage negative pressure source 28. FTC.3a (FIG. 12a) shows a patch connector with a similar construction to FTC.3 and adapted for placement at any location on the overdrape 24. FTC.3a is provided with a Leur lock connector 62. FTC.3b (FIG. 12b) comprises a strip of hydrophobic (PUE) foam material partially covered by an overdrape 64, which can be configured as a wrap around a patient's limb or extremity 66. FTC.3c (FIG. 12c) is an elbow-type connector. FTC.3d (FIG. 12d) is a bellows-type elbow connector, which is adapted to accommodate deflection of the vacuum drain tube 60.

FIGS. 12e,f show an alternative construction of FTC.2a with multiple, removable wedges 57 formed therein and adapted for accommodating articulation, such as joint flexure. The flexibility of FTC.2a can thus be considerably enhanced for purposes of patient comfort, mobility and flexibility. Such wedges can extend transversely and/or longitudinally with respect to FTC.2a. FTC.2a functions in a similar manner with and without the wedges 57 in place or removed.

FIG. 12g shows a modified patient interface 312 with the underdrape 20 placed below FTC.1. This configuration permits removing FTC.1 without disturbing the underdrape 20. FIG. 12h shows a further modified patient interface 412 with FTC.1 having the same configuration or footprint as FTC.2, whereby they can be fabricated and bonded together. In this configuration the underdrape 20 can be omitted.

III. Treatment Method

Figure 13A:
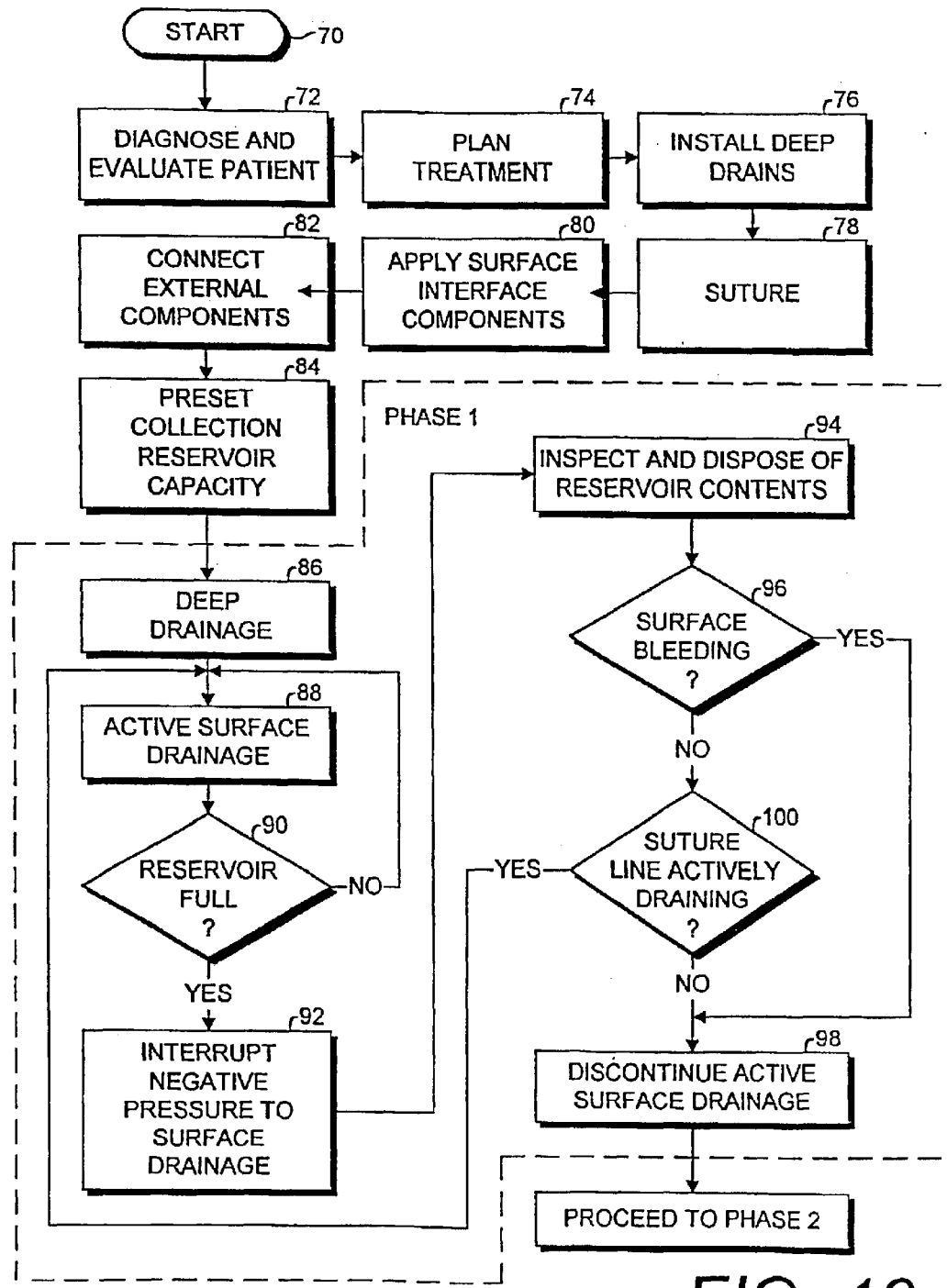
FIGS. 13a–c comprise a flowchart showing a tissue closure treatment method embodying the present invention.
Figure 13B:
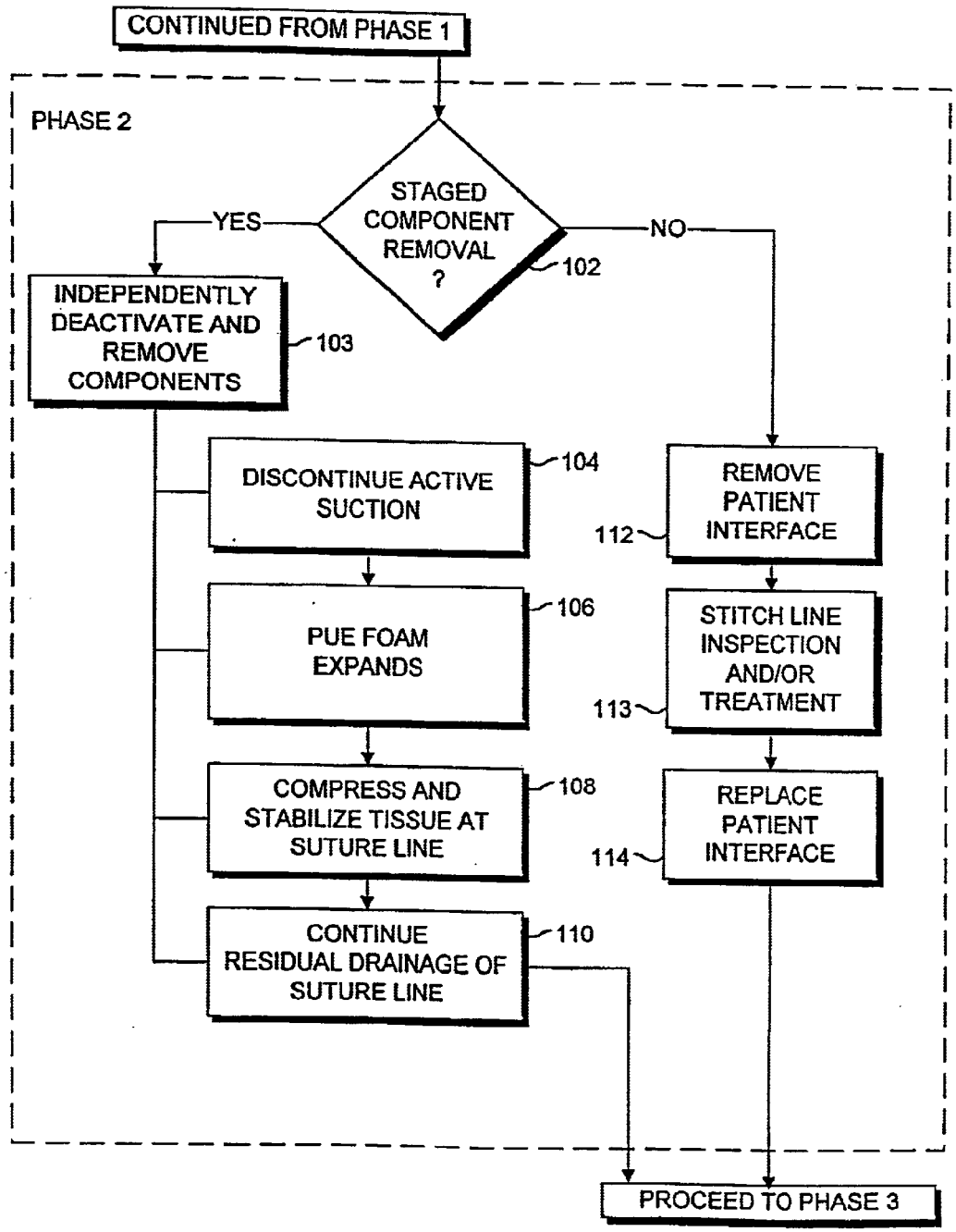
Figure 13C:
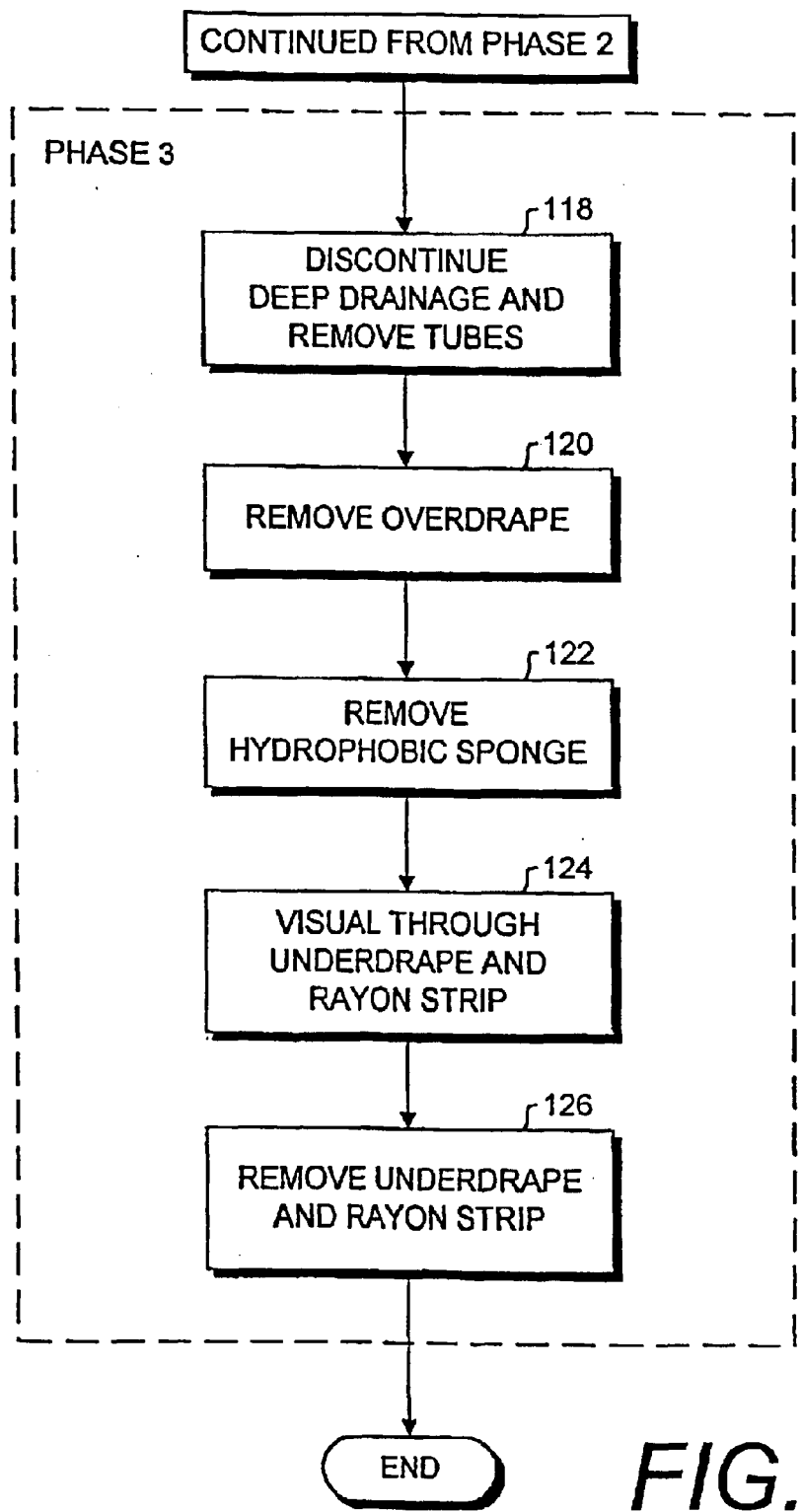

FIGS. 13a–c comprise a flowchart for a method embodying the present invention. From start 70 the method proceeds to patient diagnosis and evaluation at 72 and treatment plan at 74. Deep drains 14 are installed at 76 as necessary, and the incision is sutured at 78. Surface interface components 12 are applied at 80 and connected to the external components (i.e., negative pressure sources 15, 28) at 82. The collection reservoir capacity is preset at 84 based on such factors as nature of wound/incision, blood flow, etc.

Phase 1

Deep drainage occurs at 86 and active surface drainage occurs at 88, both being influenced by the negative pressure sources 15, 28. The negative pressure source 28 causes the PUE foam FTC.2 to partially collapse, which correspondingly draws down the overdrape 24 and exerts a positive, compressive force on the closed wound or incision 6. In the closed environment of the patient interface 12, such force is effectively limited to ambient atmosphere. This limiting control feature protects the patient from excessive force exerted by the patient interface 12. The steady force of up to one atmosphere applied across the closed wound or incision 6 functions similarly to a splint or plaster cast in controlling edema and promoting healing.

A "Reservoir Full" condition is detected at 90 and branches to an interrupt of the surface drainage negative pressure at 92, after which the reservoir contents are inspected and disposed of at 94. If surface bleeding is detected by visual inspection at decision box 96, the method branches to a "Discontinue Active Surface Drainage" step at 98. If the suture line is actively draining at decision box 100, the method loops to the active surface drainage step 88 and continues, otherwise active surface drainage discontinues at 98, i.e. when the wound/incision is neither bleeding nor exuding fluids.

Phase 1 is generally characterized by deep drainage (interactive or passive) and active surface drainage under the influence of manual or powered suction. The normal duration is approximately two to three days, during which time post-operative or post-trauma swelling normally reaches its maximum and begins to recede.

Phase 2

FIG. 13b shows Phase 2 commencing with a "Staged Component Removal?" decision box 102. An affirmative decision leads to independently deactivating and removing components at 103, including discontinuing active suction at 104, which transforms the hydrophobic PUE foam (FTC.2) internal pressure from negative to positive and allows the collapsed FTC.2 to reexpand at 106, potentially increasing surface composite pressure from ambient to positive. Preferably this transition occurs without applying undue pressure to the surface from the decompressed, expanding FTC.2. During Phase 1, negative pressure (i.e., suction/vacuum) tends to compress FTC.2 and correspondingly contracts the overdrape 24, adding to the compression exerted by FTC.2. When the application of negative pressure discontinues, either manually or automatically, FTC.2 re-expands against the constraints of the overdrape 24, and in an equal and opposite reaction presses against the skin 42, particularly along the stitch line 8. FTC.2 can thus automatically transform from ambient to positive pressure simply by discontinuing the application of the vacuum source.

The positive pressure exerted on the skin 42 continues to compress and stabilize tissue along the suture line 8 (step 108) in order to reduce swelling and cooperates with the operation of FTC.1 and FTC.2 to continue drainage by evaporation at the suture line 8 at step 110. A negative determination at decision box 102 leads to interface removal at 112 and, unless treatment is to be terminated, stitch line inspection and treatment at 113 and interface replacement at 114, which can involve all or part of the patient interface 12. The method then proceeds to Phase 3.

Phase 3

FIG. 13c shows Phase 3 of the treatment method wherein deep drainage is discontinued and the tube(s) is removed at 118. The overdrape 24 and FTC.2 are removed at 120, 122 respectively. The underdrape 2Q and FTC.1 are preferably configured to permit visual inspection of the suture line 8 therethrough at 124. When the suture line 8 has closed sufficiently, the underdrape 20 and FTC.1 are removed at 126 and the treatment ends at 128. Alternatively and if indicated by the patient's condition, all or part of the interface 12 can be replaced in Phase 3 and treatment continued.

IV. Alternative Embodiment Tissue Closure System 202

Figure 14:
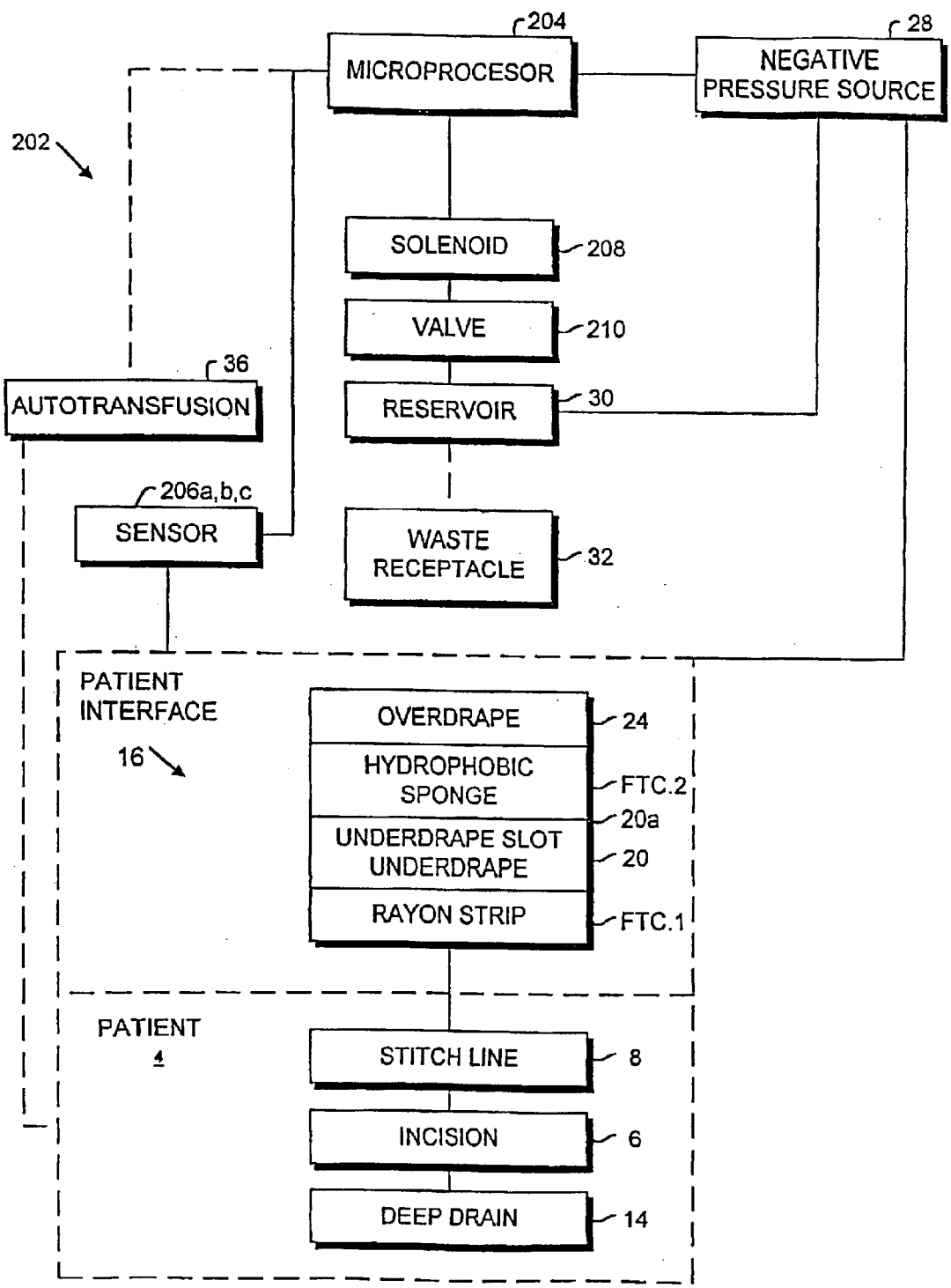
FIG. 14 is a schematic, block diagram of an automated tissue closure treatment system comprising an alternative embodiment of the present invention.

FIG. 14 schematically shows a tissue closure system 202 comprising an alternative embodiment of the present intention, which includes a microprocessor or controller 204, which can be connected to one or more sensors 206 coupled to the patient interface 12 for sensing various conditions associated with the patient 4. The microprocessor 204 can be programmed to operate a solenoid 208 coupled to a valve 210 associated with the reservoir 30 and controlling fluid flow induced by a negative pressure source 228 through its connection to the patient interface 12.

Figure 15:
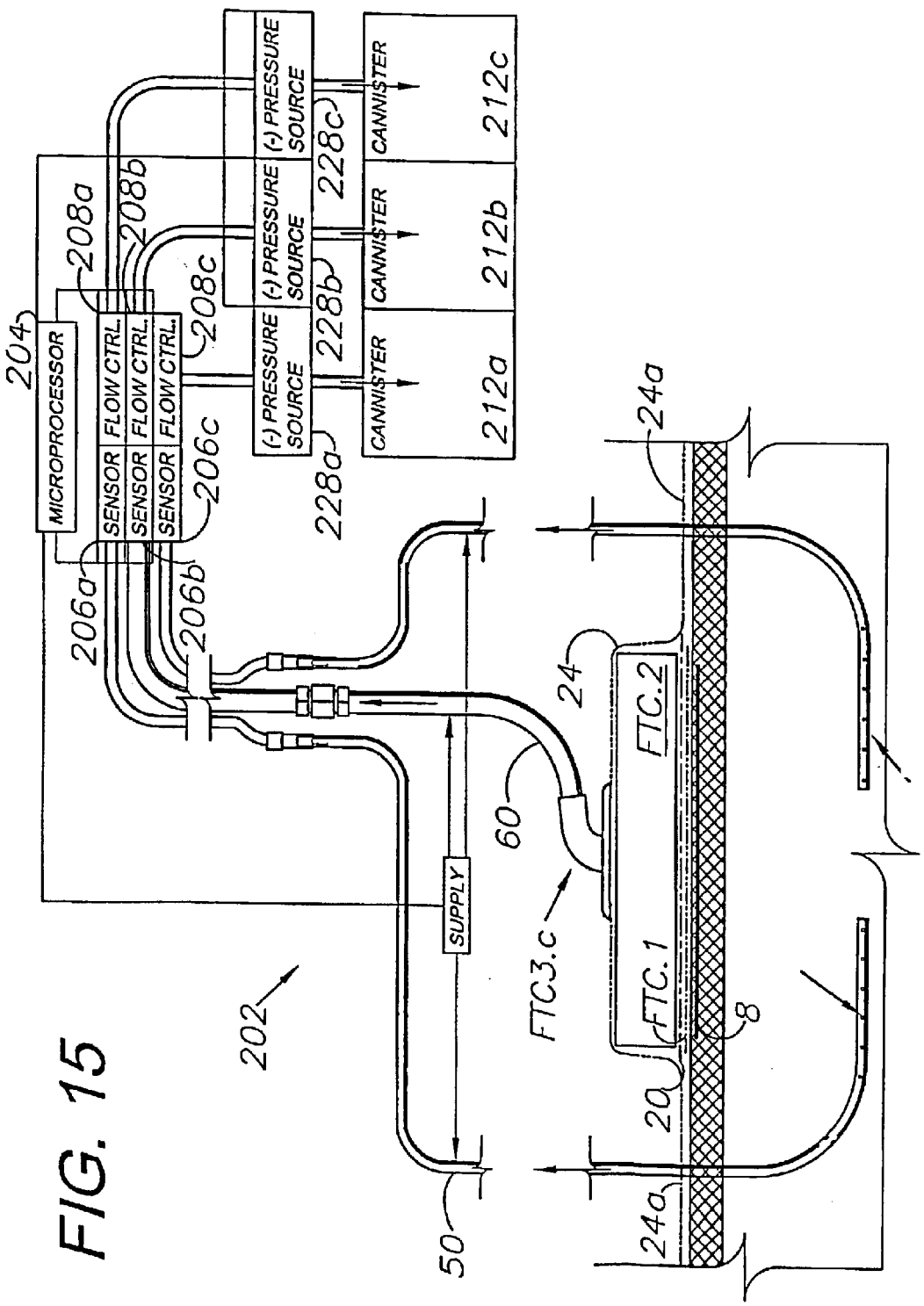
FIG. 15 is a cross-sectional view of the alternative embodiment automated tissue closure treatment system.

FIG. 15 shows the tissue closure system 202 with the microprocessor 204 connected to multiple sensors 206a,b,c each of which is associated with a flow control component, such as a valve, 210a,b,c respectively. Each flow control component 210a,b,c is associated with a respective negative pressure source 228a,b,c, which in turn controls fluid discharge into canisters or reservoirs 212a,b,c respectively. For example, the patient interface 12 can comprise an external patient interface 16 as described above and a pair of deep drainage tubes 50a,b. The patient interface 12 includes an optional supply component 214, which can comprise one or more fluid reservoirs, pumps (manual or powered) and associated controls, which can connect to the microprocessor 204 for system control. The supply component 214 optionally takes to one or more of the tubes 50, 60 for delivering fluid to the patient through the deep drainage tubes 50 or through the external patient interface 16. Such fluids can comprise, for example, antibiotics, and aesthetics, irrigating agents, growth factor, and any other fluid beneficial in promoting healing, countering infection and improving patient comfort.

Figure 16:
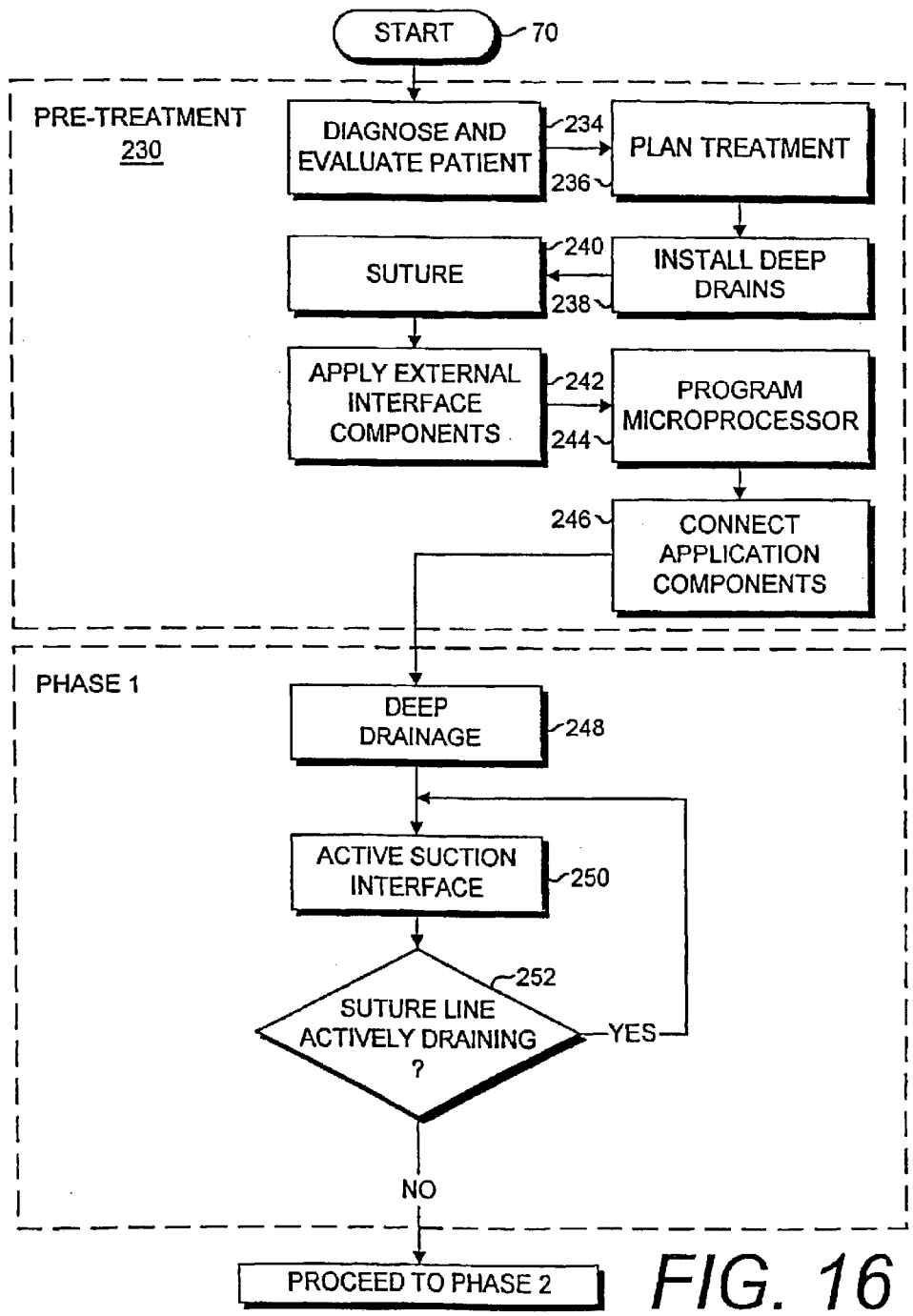
FIG. 16 is a partial flowchart of an alternative embodiment automated tissue closure treatment method embodying the present invention.
Figure 17:
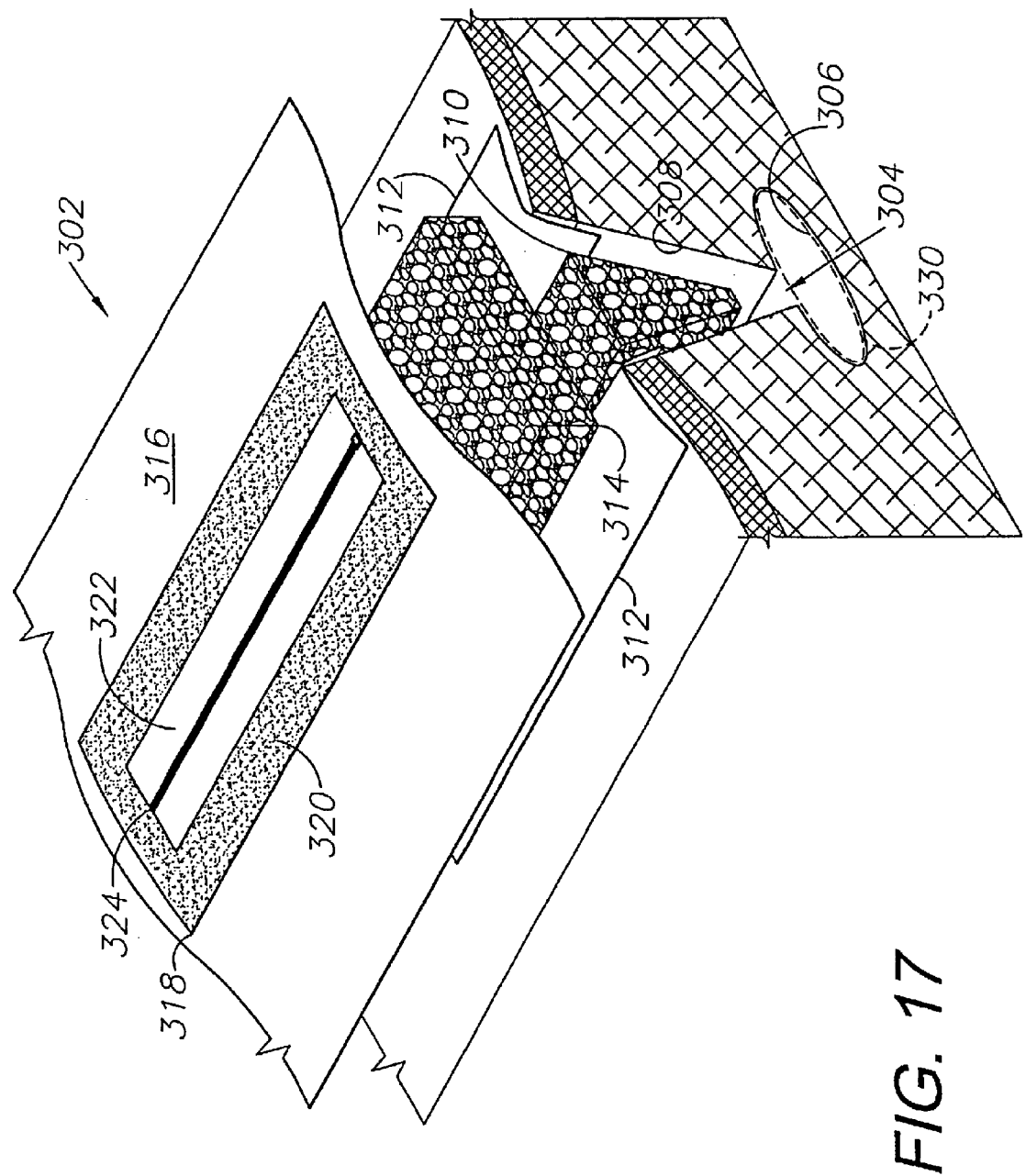
FIG. 17 is a fragmentary, perspective view of a tissue closure treatment system comprising an alternative embodiment of the present invention, with a reclosable access panel.
Figure 18:
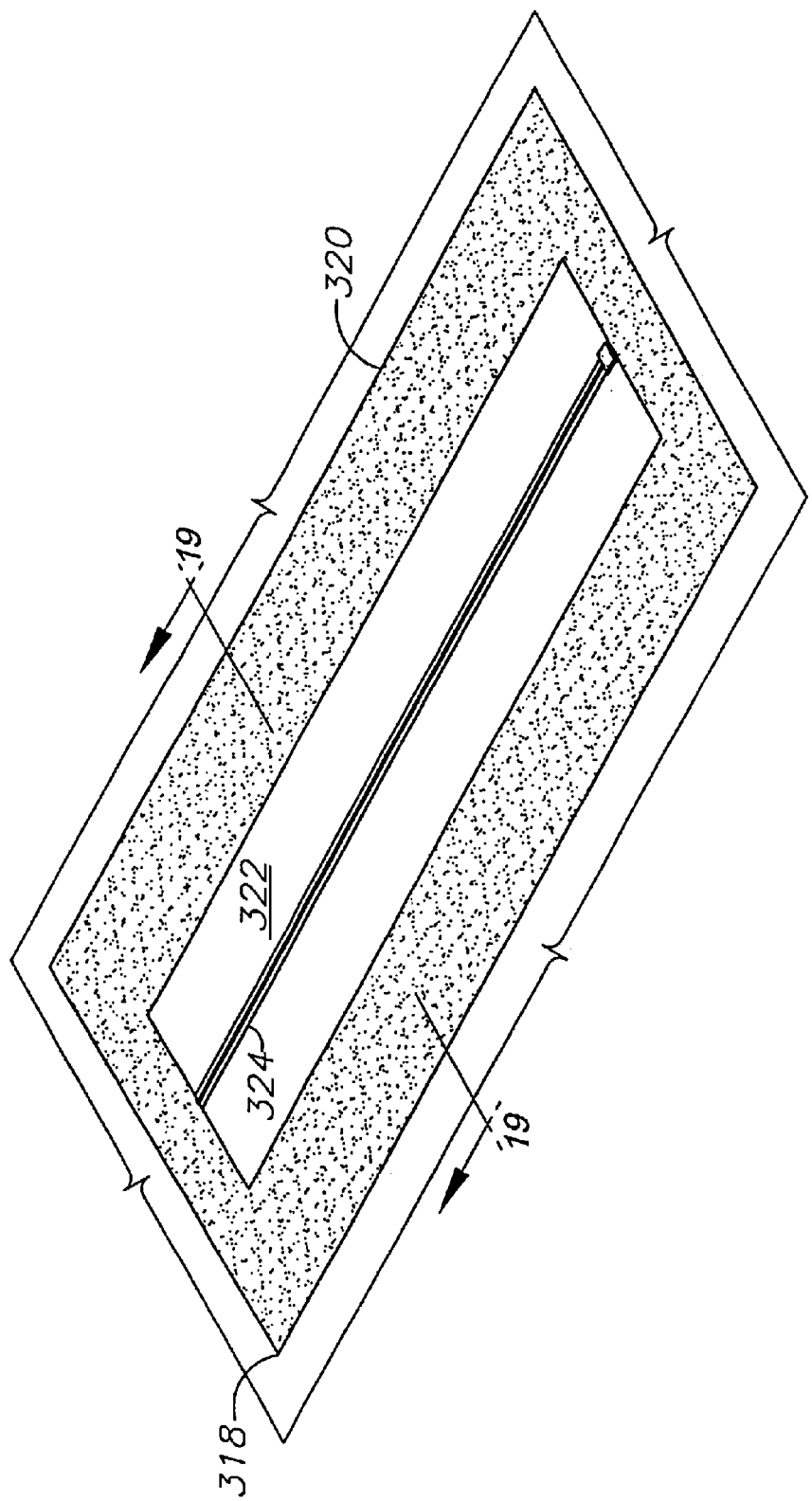
FIG. 18 is a perspective view of the reclosable access panel.

The methodology of the treatment with the alternative embodiment tissue closure system 202 is shown in FIG. 16 and generally involves modified pretreatment 230 and Phase 1 procedures. From "Start" the method proceeds to a diagnosis/evaluation step 234, a treatment plan step 236, deep drain installation 238, suturing at 240, external interface component application 242, microprocessor programming 244 and connection of the application components at 246, such as connection of the tubing. Phase 1 commences with deep drainage at 248, active suction interface at 250 and a "Suture Line Actively Draining?" decision box 252. If the suture line is actively draining, the method loops back to the active suction interface step 250, otherwise (negative determination at 252) it proceeds to Phase 2.

V. Applications

Without limitation on the generality of useful applications of the tissue closure systems 2 and 202 of the present invention, the following partial list represents potential patient conditions and procedures, which might indicate application of the present invention.

Over closed tissue separations, such as surgical incisions.

Over joints where the incision is subject to movement and stretching, such as arthrotomy, reconstructive proceedures, cosmetic procedures, flaps, scar revisions, Total Joint Replacement (TJR) procedures, i.e., hip, knee, elbow, shoulder and foot.

Any wound in an area of thick or unstable subcutaneous tissue, where splinting of skin and subcutaneous tissue might reduce dehiscence of deep sutures.

ABbr wounds over reconstructive procedures in which irregular cavities are created. These include resection of tumors, implants, bone, and other tissues. Changes in length and geometry of limbs, and changes in size, position, and contour of bones and other deep structures.

Wounds in which elimination and prevention of dead space is important.

Treatment of hematomas and seromas.

Amputation stumps.

Abdominal, thoracic, flank, and other wounds in which splinting of the wound might assist closing and mobilizing the patient during the postoperative interval.

Wounds in areas of fragile or sensitive skin, where repeated removal and replacement of tape or other adhesives might produce pain, irritation, or blistering of skin in the vicinity of the wound. Also where dressing changes might produce shear or displacement of tissue so as to compromise primary wound healing.

Wounds in cases where the patient wishes to bathe before the skin has healed sufficiently to allow protection from contamination with bath or shower water.

Wounds subject to contamination with feces, urine, and other body fluids.

Pediatric, geriatric, psychiatric, and neurologic patients, and other patients likely to disturb dressings and wounds.

Patients with multiple consultants and care givers, where repeated inspection of the wound might compromise healing.

Deep closure and surface sutures and staples.

Any clean surgical or traumatic incision, open, or fully or partially closed by sutures, or where the skin edges can be apposed to a gap no wider than the width of the negative pressure zone of the dressing, i.e. where the maximum separation is less than or equal to the width of FTC.1 (rayon strip).

In cosmetic and reconstructive surgery, the systems and methods of the present invention can control and conceal the effects of early bleeding, exudation, ecchymosis, and edema of the wound.

In surgery on the limbs, where compression and drainage by this method might eliminate or reduce the need for circumferential compressive wrapping.

Tissue separations that are prone to protracted drainage, such as hip and knee incisions, and tissue separations in patients with health conditions, such as diabetes, that tend to inhibit healing. Shortened hospital stays might result from swelling reduction and control of drainage.

VI. Case Studies

General concept: sequential surface application of foam material (FTC.2) to surgical site and other wounds. Air-drying at the suture line is facilitated by the rayon strip (FTC.1).

Phase 1: deep drainage (drain tube(s)), active or passive; active suction applied to surface PUE foam (placed on top of surgical incision, drains bleeding and exudate from suture line); active suction compresses PUE foam, thus applying positive compression to the entire dissection field; adhesive-lined film underdrape with an MVTR of 3–800 on skin underlying PUE foam; rayon (or other suitable porous wicking material) strip on suture line; similar type of adhesive film overdrape (MVTR of 3–800) overlying PUE foam material.

Duration: approximately 2–3 days, i.e. effective time for active drainage from incision/stitch line to cease and for suture line to dry and heal.

Phase 2: Remove active suction by cutting off (elbow) connector and leave FTC.2 in place. Released from suction, FTC.2 expands against the overdrape and exerts positive pressure differential on the operation site. May maintain continued mild compression throughout Phase 2; residual drainage function through rayon strip and into FTC.2 provides continued drying of suture line. Deep drain tubes remain in place during Phase 2 for active deep drainage.

Duration: approximately three days, i.e. days 3–6 after operation.

Phase 3: remove overdrape and FTC.2; leave underdrape and rayon strip in place; visually observe wound healing progress; transparency desirable.

Duration: several (e.g., up to three) weeks.

Clinical trial confirmation: Closure of surgical site in upper chest area in patient with severe healing problems showed excellent results and rapid wound healing.

Subcuticular (subepidermal) sutures avoid conflict with rayon strip and need for early suture removal, or pressure on skin sutures beneath compressive black sponge.

Option: use pressure transducer for interface pressure mapping of wound site and automate control and monitor pressures, flow, etc.

VII. Alternative Embodiment Tissue Closure System 302.

A tissue closure system 302 comprising an alternative embodiment of the present invention is shown in FIGS. 17–22. The system 302 is adapted for closing a wound 304 with an undermined area 306 just above the fascia and an upper tissue separation 308 located primarily in the dermis and in the subcutaneous layer. A wedge-shaped internal fluid transfer component (foam piece) 310 is located in the tissue separation area 308 and is installed between side drapes 312 located on either side of the wound 304. An external fluid transfer component (foam piece) 314 is placed on top of the internal component 310 and the side drapes 312, and is covered by an outer drape 316. An optional innermost foam piece 330 can be located in and sized to fit the undermined area 306 and can transfer fluid and gradient forces to and from the internal foam piece 310.

Figure 20:
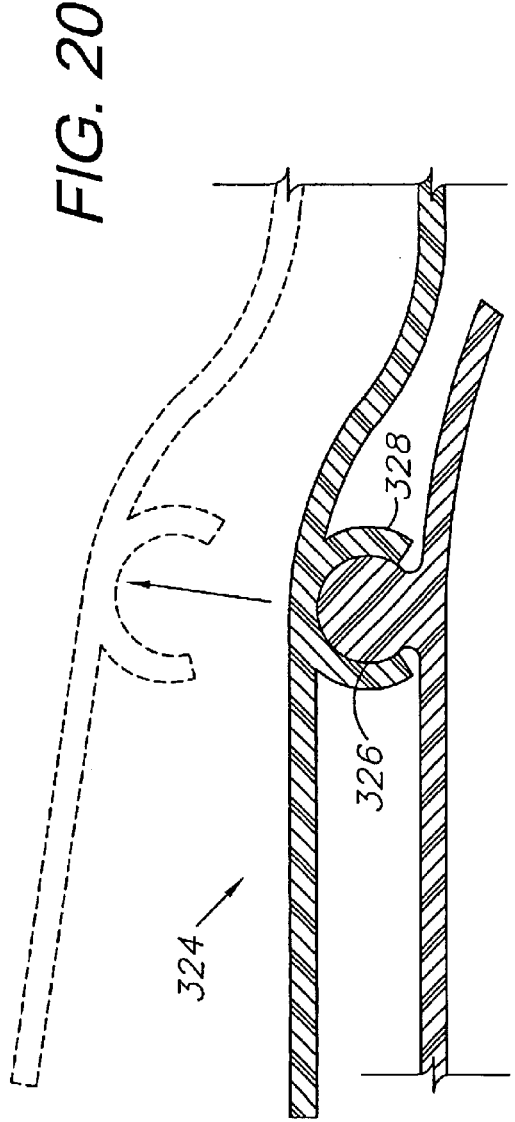
FIG. 20 is an enlarged, cross-sectional view of the tissue closure system, particularly showing a reclosable seal strip thereof.
Figure 19:
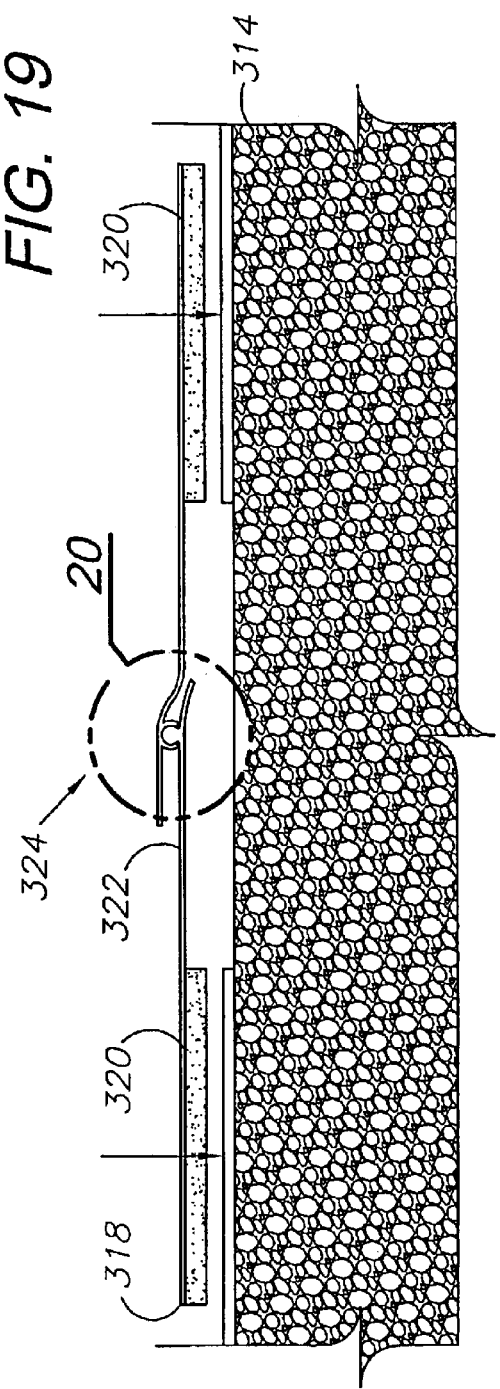
FIG. 19 is a cross-sectional view of the tissue closure treatment system, taken generally along line 19—19 in FIG. 18.
Figure 21:
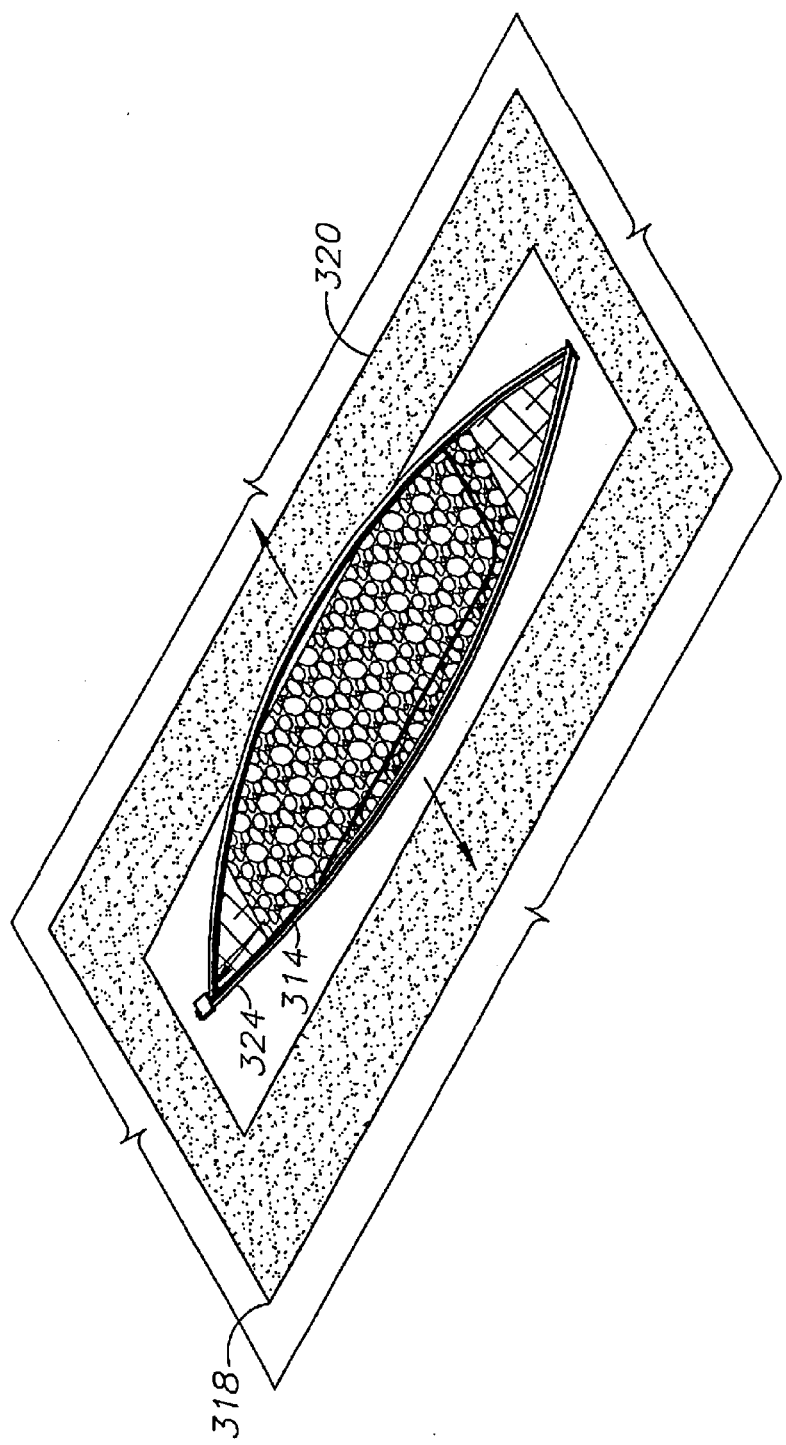
FIG. 21 is a perspective view of the tissue closure system, showing the seal strip open.
Figure 22:
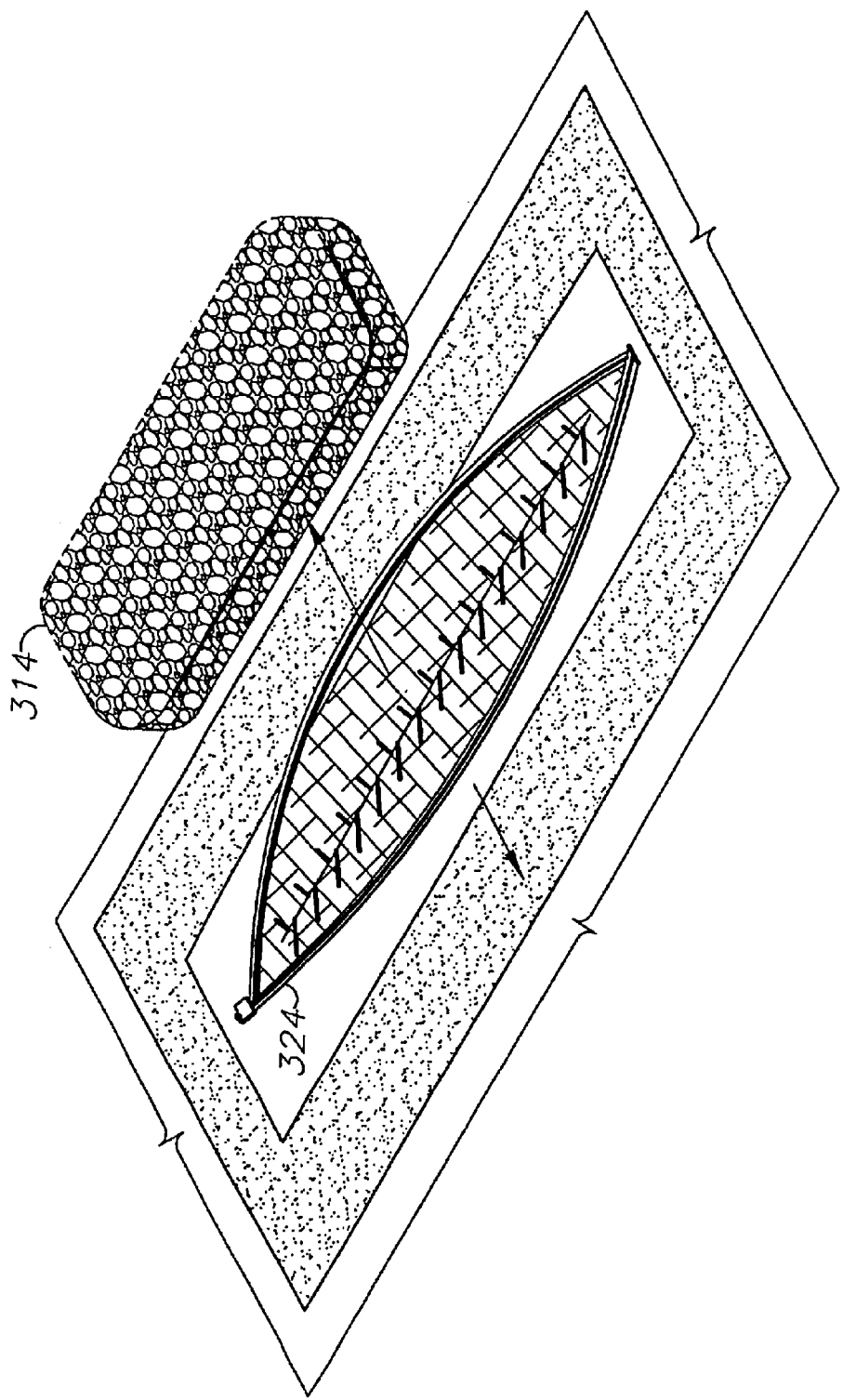
FIG. 22 is a perspective view of the tissue closure system, showing the seal strip open and a foam piece removed.

A reclosable access panel 318 is placed over an opening formed in the outer drape 316 and includes an adhesive-coated perimeter 320 surrounding an adhesive-free center area 322 with a reclosable seal strip 324 extending longitudinally down the centerline thereof. The seal strip 324 includes a rib or bead 326, which is releasably captured in a channel 328 (FIG. 20).

In operation, the reclosable access panel 318 is adhesively secured around its perimeter 322 to the outer drape 316 and provides access to the foam pieces 310, 314 of the dressing system 302. For example, the foam pieces 310, 314 can be changed (FIGS. 21 and 22), treatments can be applied and wound healing progress can be visually monitored.

VIII. Alternative External Dressing 402.

FIGS. 23–27 show an external dressing 402, which can be premanufactured or preassembled and used for various wound treatment and closure applications. The dressing 402 includes a foam piece 404 partially enclosed in a rayon covering 406, which includes an open top 408 secured to an upper perimeter 410 of the foam piece 404, for example, by sutures, staples, adhesive or some other suitable mechanical fastener as shown at 412. The dressing 402 is preferably preassembled with an outer drape 414 including a foam-covering central portion 416 and a perimeter, patient-contact skirt portion 418. A tucked margin 420 is formed at the intersection of the drape portions 416, 418 and partially underlies the foam piece 404 in order to protect the skin and prevent the formation of low-pressure, vacuum voids around the edge of the foam piece 404 whereat blistering could otherwise occur. In operation, the dressing 402 can be easily changed by cutting around the margin 420, removing the foam piece 404 and the drape outer portion 416. The wound can thus be inspected, cleaned, debrided, treated, etc. and a new dressing 402 put in place. The patient-contact skirt portion 418 of the original dressing can remain in place.

Figure 23:
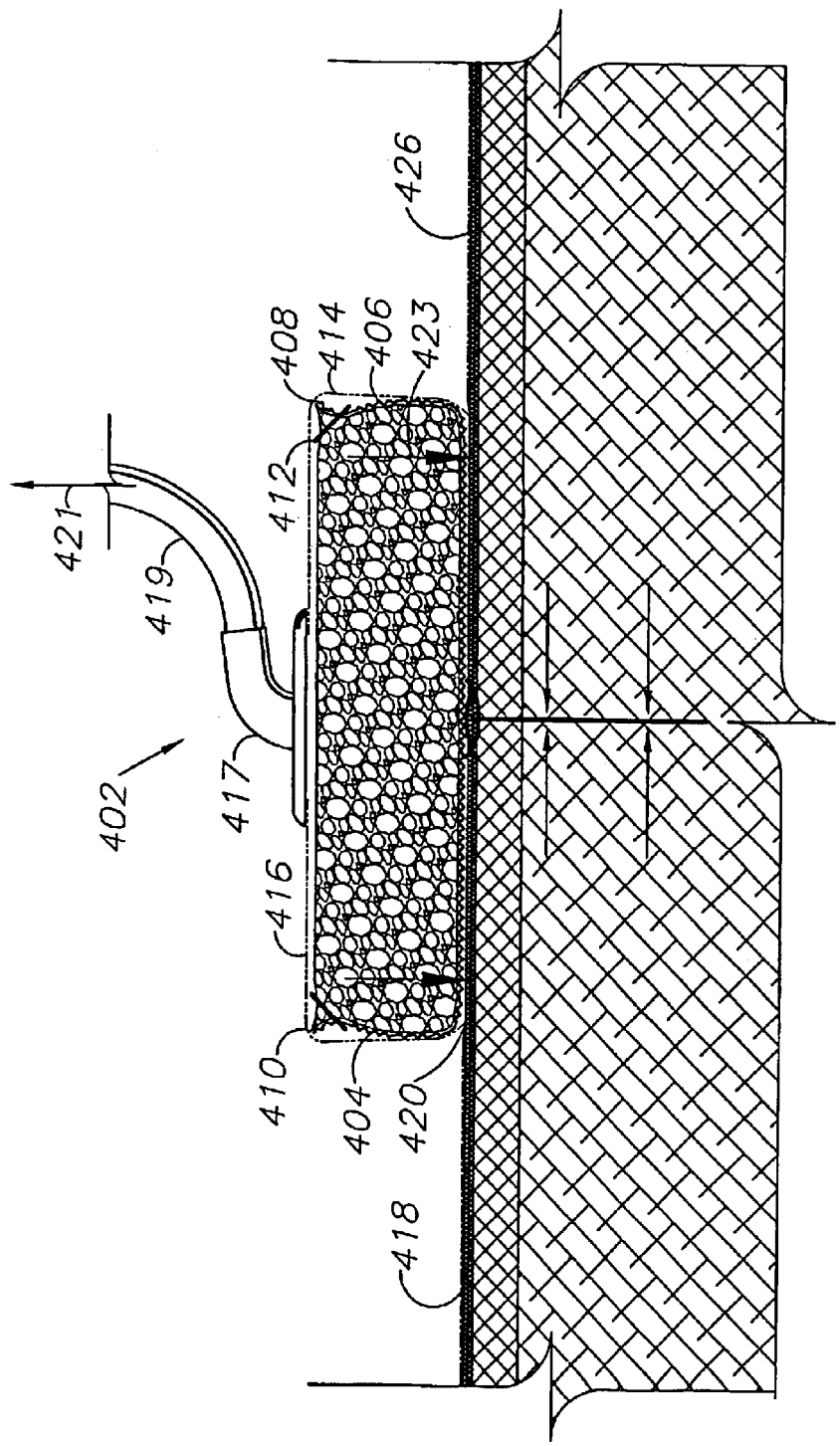
FIG. 23 is a cross-sectional view of an external dressing assembly, which comprises an alternative embodiment of the present invention.

FIG. 23 shows a fluid flow (discharge) directional arrow 421 from an elbow coupling 417 and a discharge tube 419. Alternatively, fluid could be injected into the dressing 402 through the tube 419 and the coupling 417. Hydraulic/pneumatic compressive force arrows 423 are shown in FIG.

23 and represent the downward (i.e. into patient) forces, which can be established by compressing the foam piece 404 under suction and then releasing the negative pressure differential, thus transitioning the dressing to a positive pressure differential. In a positive pressure differential mode of operation, the dressing 402 controls edema by pressing the foam piece 404 against the tissue adjacent to the wound. There are many potential medical benefits from controlling edema in this manner. For example, healing is promoted, scar tissue is minimized and patient discomfort can be reduced.

Figure 24:
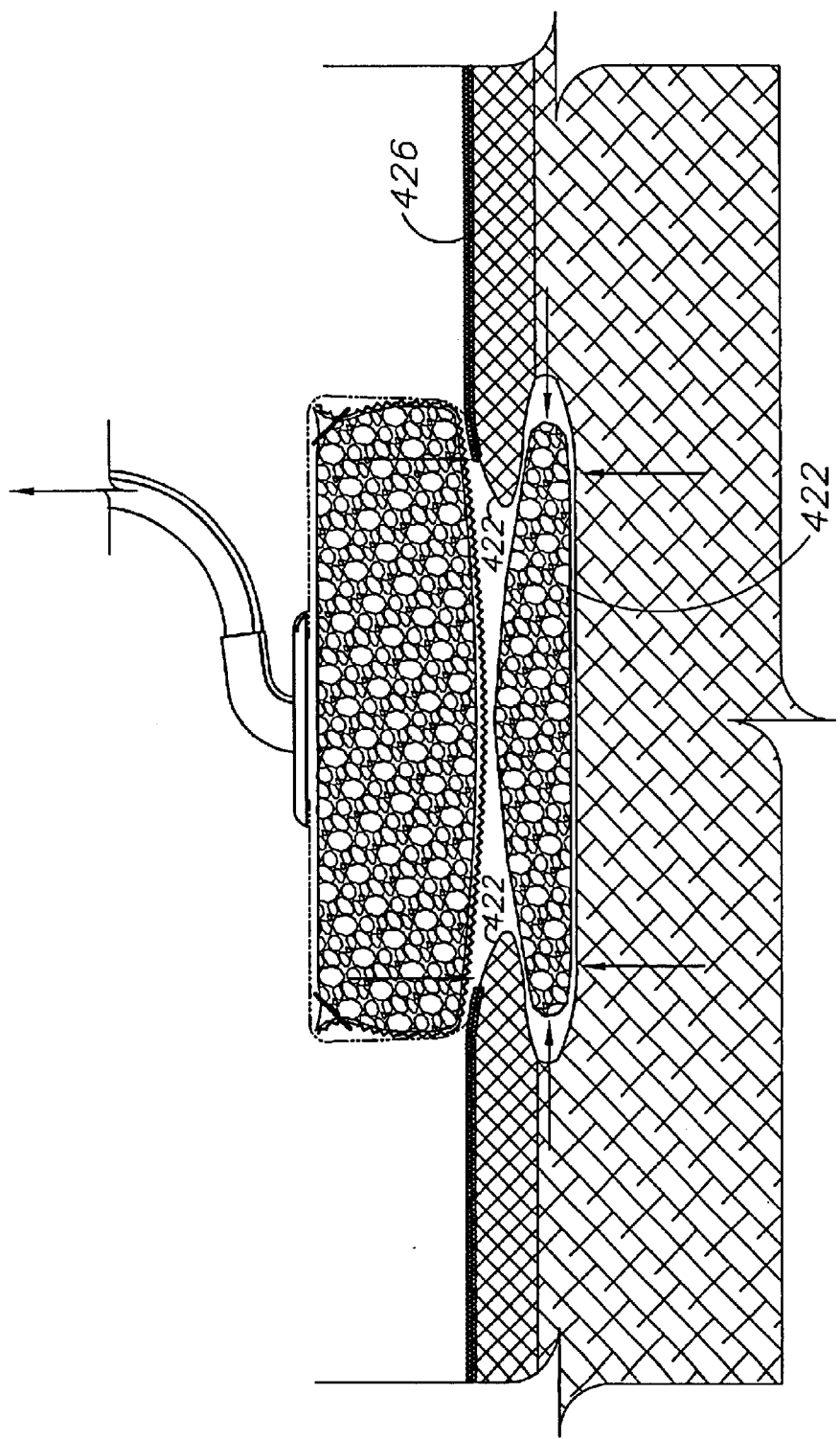
FIG. 24 is a cross-sectional view of an alternative embodiment tissue closure system with internal and external foam pieces.

FIG. 24 shows the external dressing 402 used in conjunction with an internal foam piece 422, which is located below the dermis at the top of the subcutaneous layer. The internal foam piece 422 is adapted for applying a pressure differential within the subcutaneous layer whereby tissue growth and closure are promoted. The inside/outside configuration of the dressing system shown in FIG. 24 can rehabilitate and make pliable a wound edge 424 that has contracted and become hard, immobile and edematous by applying pressure differentials across the external and internal foam pieces 404, 422, such as compression (positive pressure differential) for edema control.

Figure 25:
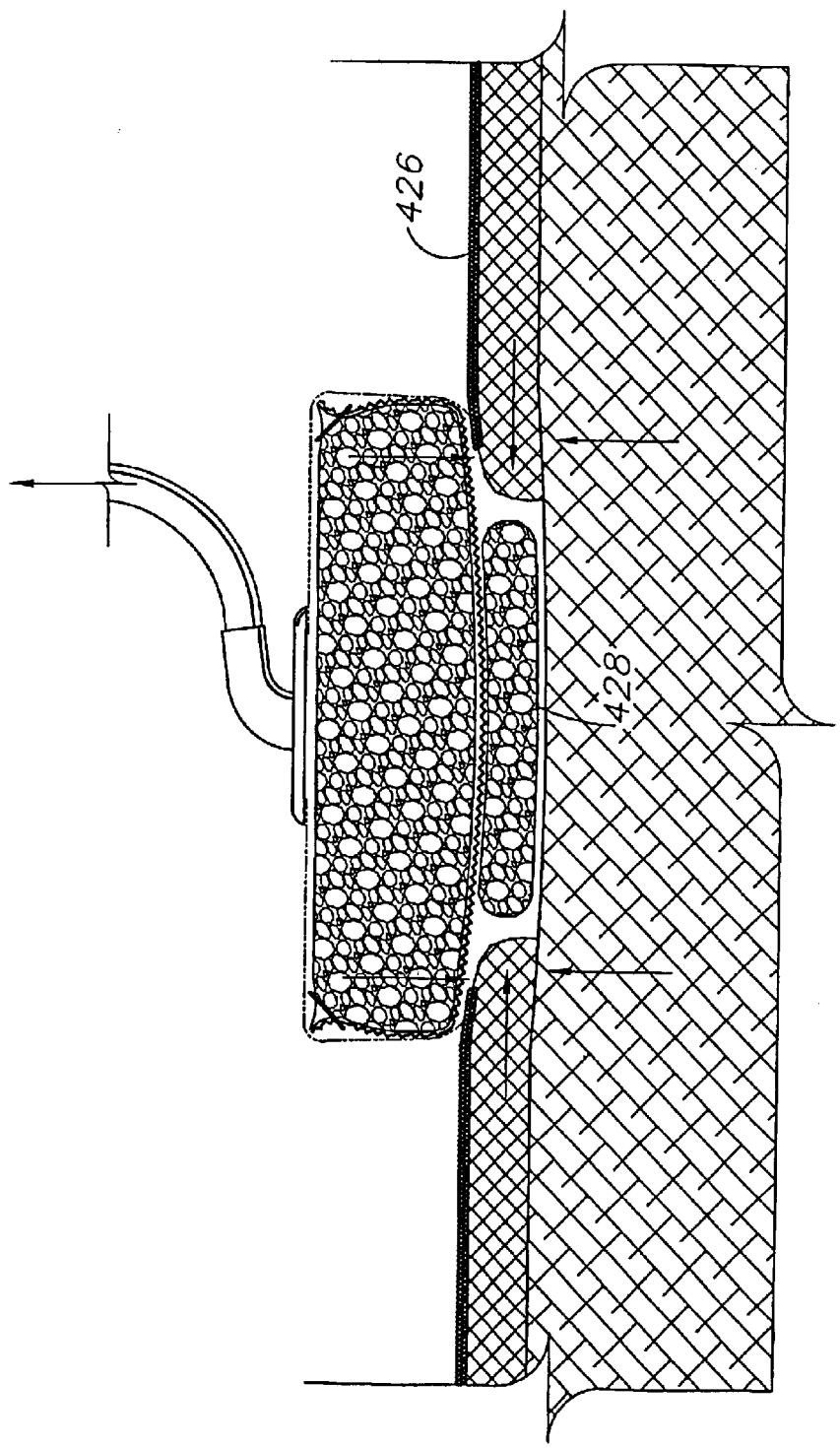
FIG. 25 is a cross-sectional view of the system shown in FIG. 24, showing the progressive healing of tissue in the wound.
Figure 26:
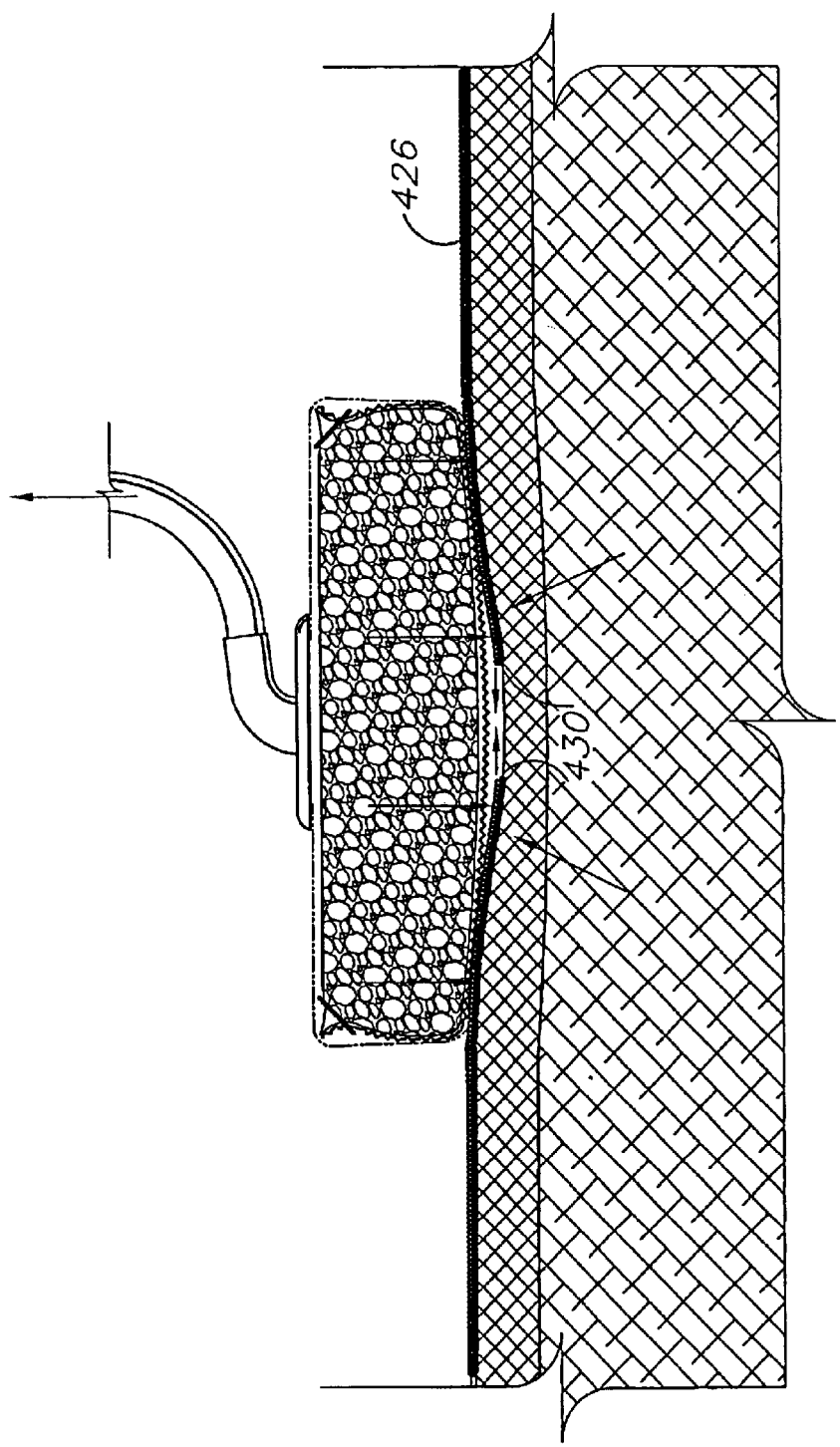
FIG. 26 is a cross-sectional view of the system shown in FIG. 24, showing the reepithelialization of the wound.
Figure 27:
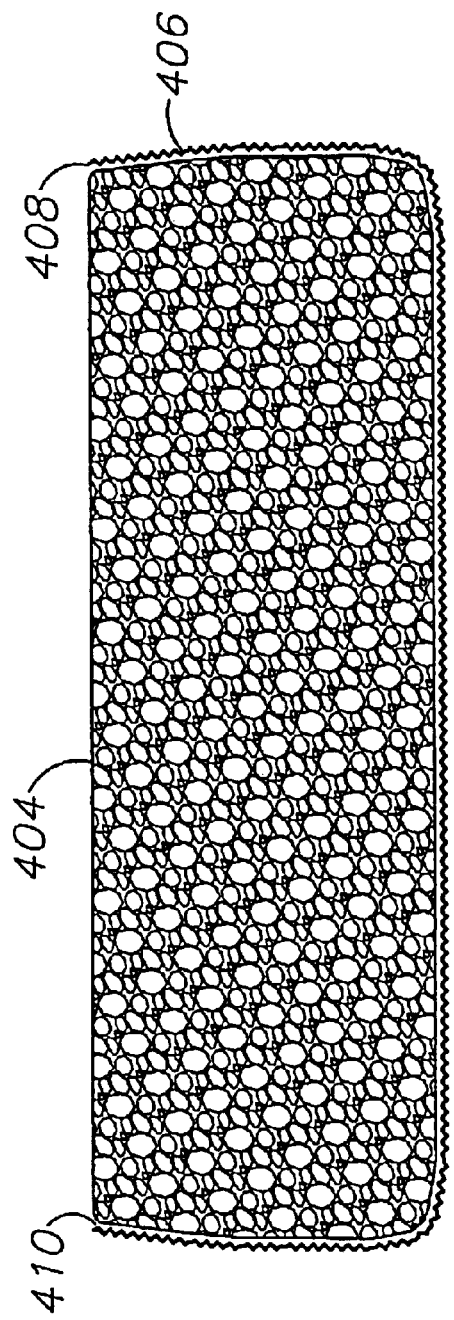
FIG. 27 is a cross-sectional view of a foam piece partially enclosed in rayon.

FIG. 25 shows the wound confined to the dermis 426 with another internal foam piece 428 in place. The subcutaneous layer is substantially healed. FIG. 26 shows the external foam piece 404 in place alone for drawing the wound edges 430 together at the epidermis. FIG. 27 shows the external foam piece 404 covered on the sides and bottom by the rayon covering 406, leaving an open top 408.

IX. Alternative Embodiment Dressing System 502

Figure 28:
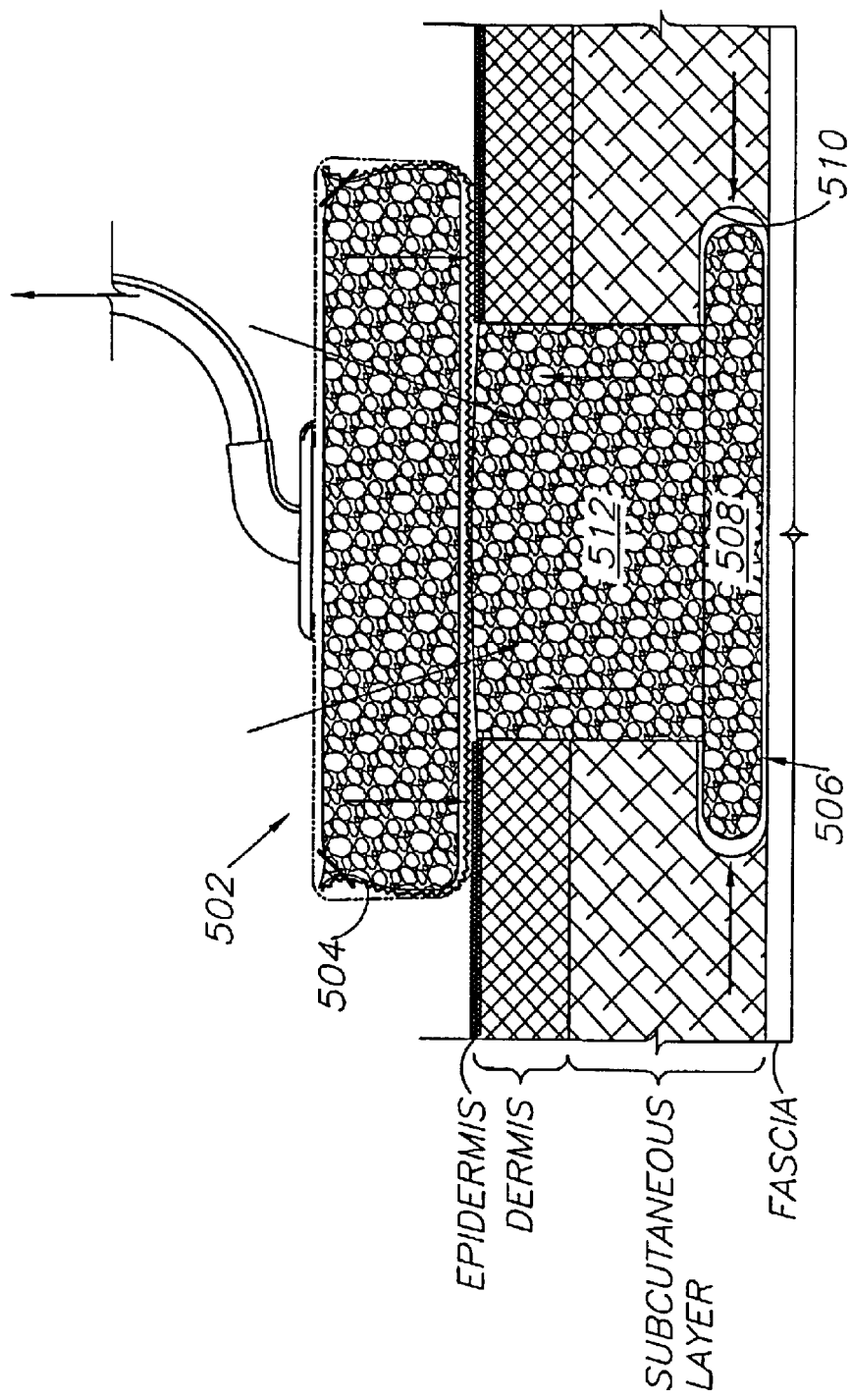
FIG. 28 is a cross-sectional view of an alternative embodiment tissue closure system, with an external foam piece and an internal foam piece assembly.

FIG. 28 shows yet another alternative embodiment internal/external dressing system configuration 502 with an external foam piece 504 similar to the foam piece 404 described above and an internal foam assembly 506 located in the dermis and in the subcutaneous layer. The assembly 506 consists of a proximate internal foam piece 508, which can be located at the bottom of the subcutaneous layer on top of the fascia in an undermined cavity 510 formed by the wound, and a distal internal foam piece 412 located primarily in the dermis and the subcutaneous layer portions of the wound between the external foam piece 504 and the proximate internal foam piece 508.

The dressing system configuration 502 can be configured and reconfigured as necessary to accommodate various wound configurations in various stages of healing. For example, the proximate internal foam piece 508 can be removed when the undermined cavity 510 closes. Likewise, the distal internal foam piece 512 can be removed when the subcutaneous layer and the dermis have healed. Moreover, the foam pieces 504, 508 and 512 can be replaced with different sizes of foam pieces as necessary in connection with dressing changes and as the wound configuration changes. Such sizes and configurations can be chosen to optimize the beneficial effects of pressure gradients (both positive and negative), fluid control, edema control, antibacterial measures, irrigation and other treatment protocols. Still further, the access panel 318 described above can be used in conjunction with the dressing system 502 in order to provide access to the foam pieces thereof and to the wound itself.

Figure 29:
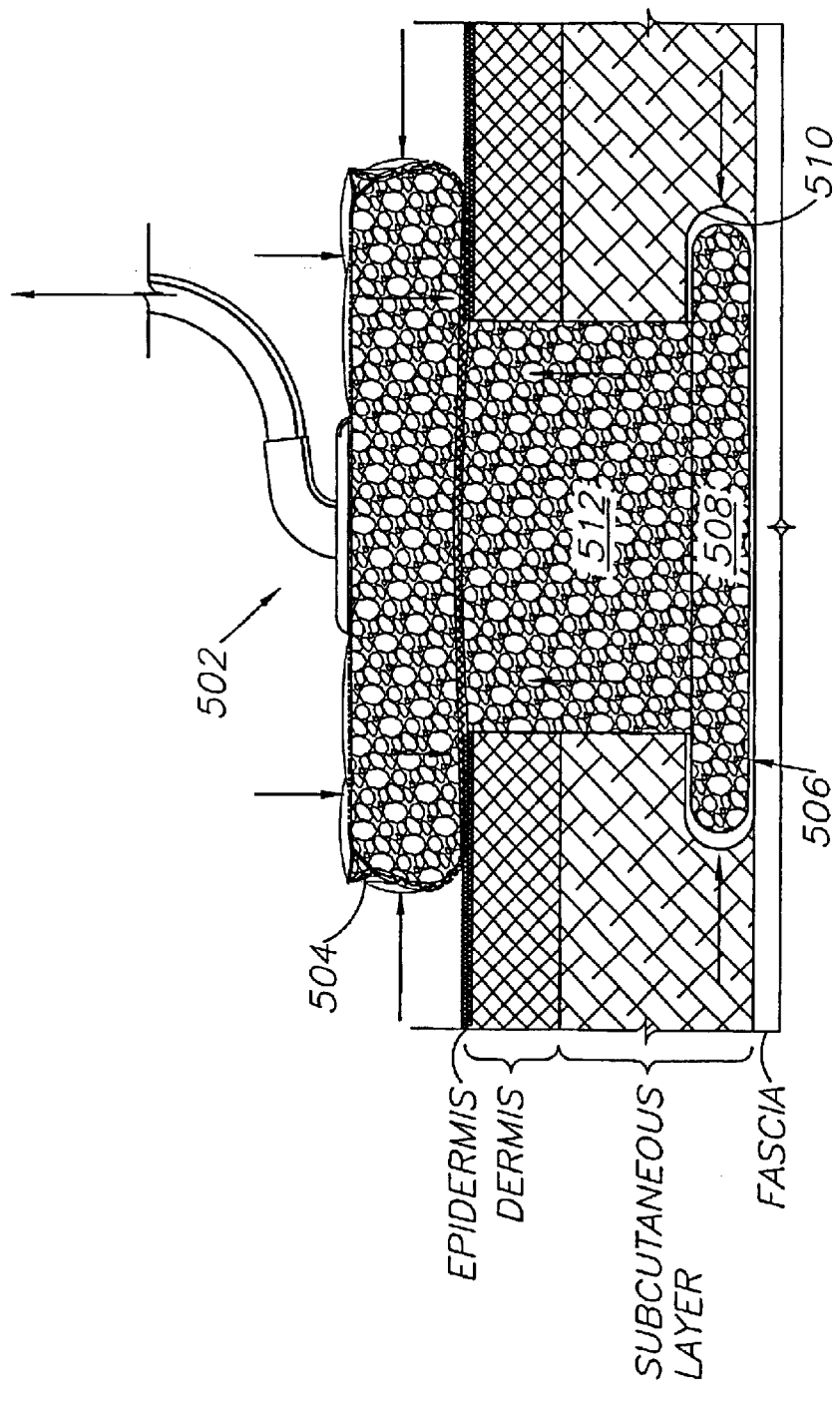
FIG. 29 is a cross-sectional view thereof, shown partially collapsed under ambient atmospheric pressure.
Figure 30:
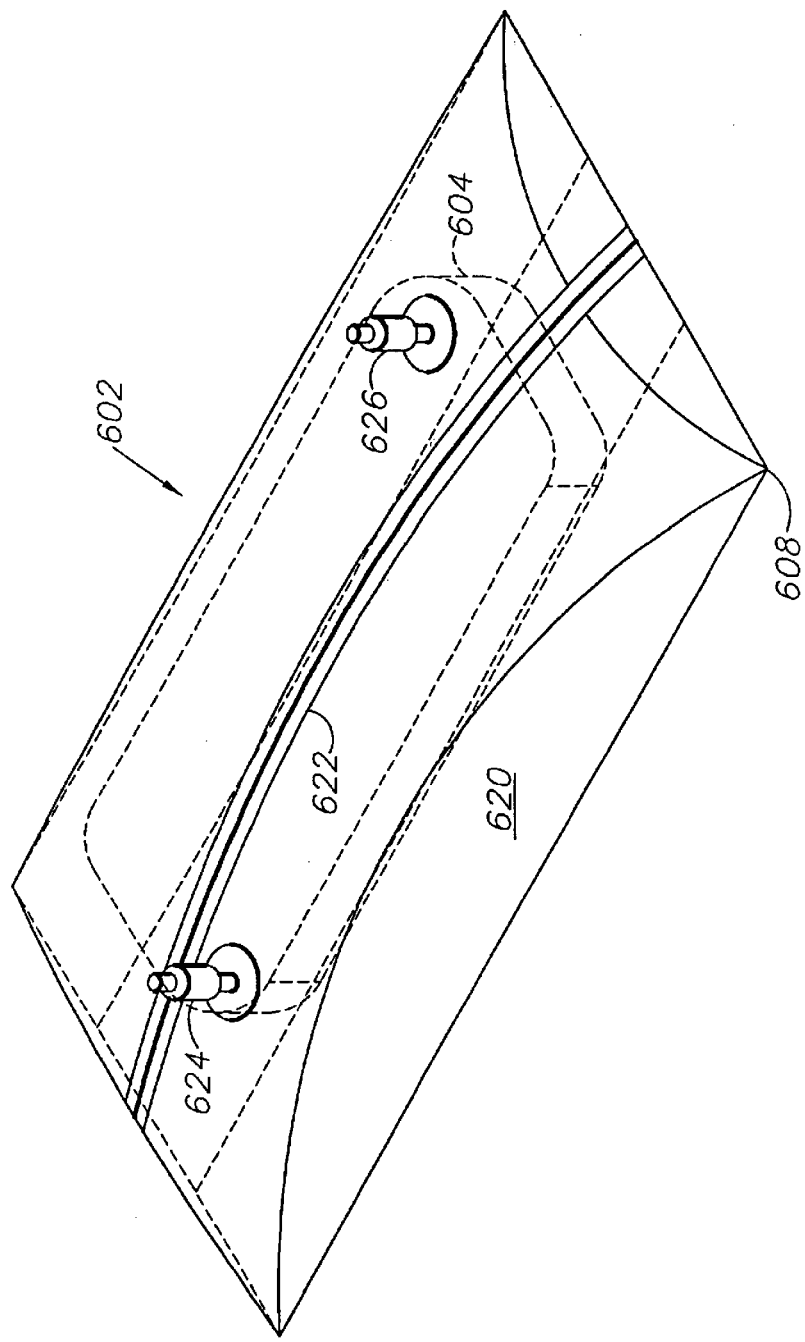
FIG. 30 is a perspective view of an alternative construction dressing with a reclosable seal strip and fluid access ports.

FIG. 29 shows the internal/external dressing system 502 compressed under the vacuum effects of an external vacuum source with the drape 316 drawn tightly down on the compressed outer foam piece 504. Thus compressed, the system 502 is adapted to transfer positive pressure differential, compressive forces to the area of the wound.

X. Alternative Embodiment Dressing Assembly 602

FIGS. 30–37 show a reclosable, preassembled external dressing assembly 602 comprising an alternative embodiment of the present invention. The dressing assembly 602 includes a foam piece 604, which can be completely covered in rayon 606 or some other suitable material with the desired absorbent and/or wicking capabilities. The foam piece 604 also includes a core 605 comprising a suitable material, such as polyurethane, hydrophobic foam. Alternatively, other foam materials with hydrophobic or hydrophilic properties can be utilized. Various sizes and shapes of the foam piece 604 can also be employed, including cutting and trimming it to size during the course of a medical procedure.

Figure 31:
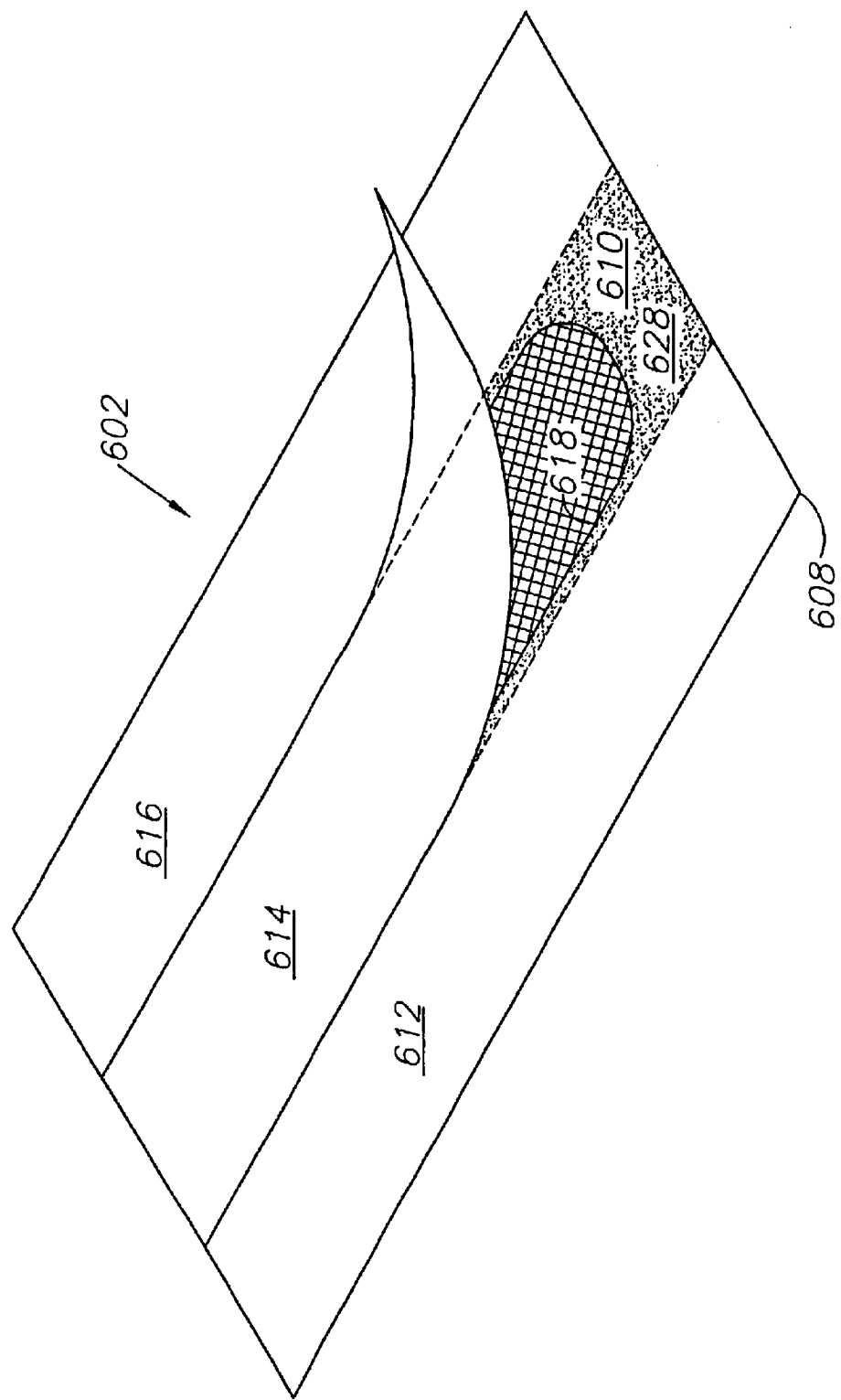
FIG. 31 is a perspective view of the underside of the dressing, showing a middle backing strip being removed.

The foam piece 604 is removably placed in a reclosable sheath 608 including a bottom panel 610 selectively covered by removable, adhesive backing strips 612, 614 and 616 forming a central opening 618. As shown in FIG. 31, a central opening 618 in the bottom panel 610 is initially covered by the center backing strip 614. Removing the center backing strip 614 exposes the foam piece 604 through the opening 618. The reclosable sheath 608 also includes a top panel 620 with a reclosable seal strip 622 extending from end-to-end and generally longitudinally centered. The seal strip 622 can be similar in construction to the reclosable seal strip 324 described above. The top panel 620 also includes fluid ports 324, 326, which can comprise, for example, Leur lock connectors or some other suitable fluid connection device.

The sheath 608 can comprise polyethylene or some other suitable material chosen on the basis of performance criteria such as permeability, flexibility, biocompatibility and antibacterial properties. Various permeable and semi-permeable materials are commonly used as skin drapes in medical applications where healing can be promoted by exposure to air circulation. The sheath 608 can be formed from such materials for applications where continuous vacuum suction is available and the dressing 602 is not required to be airtight.

According to an embodiment of the method of the present invention, a dressing assembly 602 can be premanufactured, or custom-assembled from suitable components for particular applications. In a premanufactured version, the dressing 602 is preferably presterilized and packaged in sterile packaging.

Figure 32:
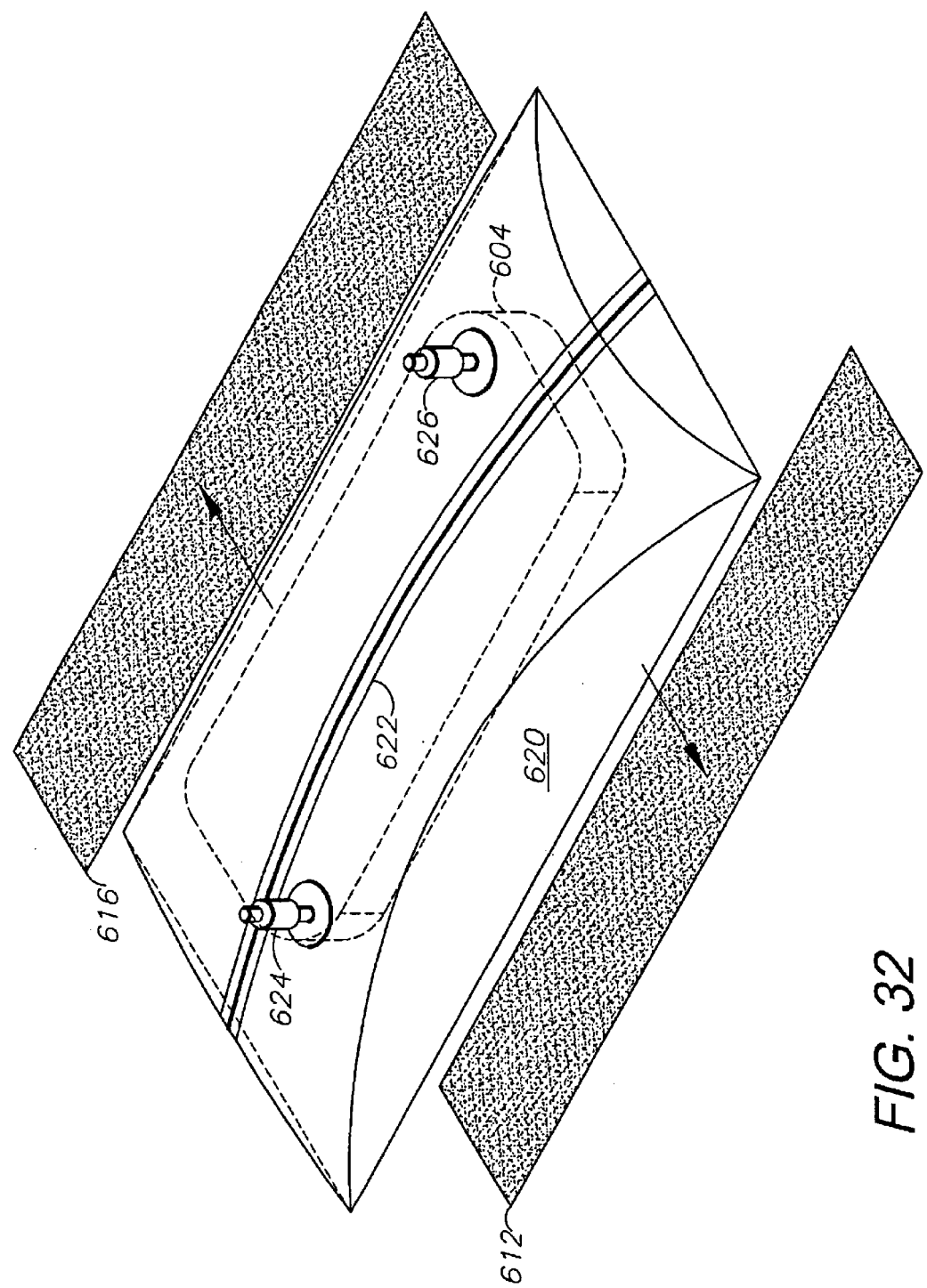
FIG. 32 is a perspective view of the dressing, showing side backing strips being removed.
Figure 33:
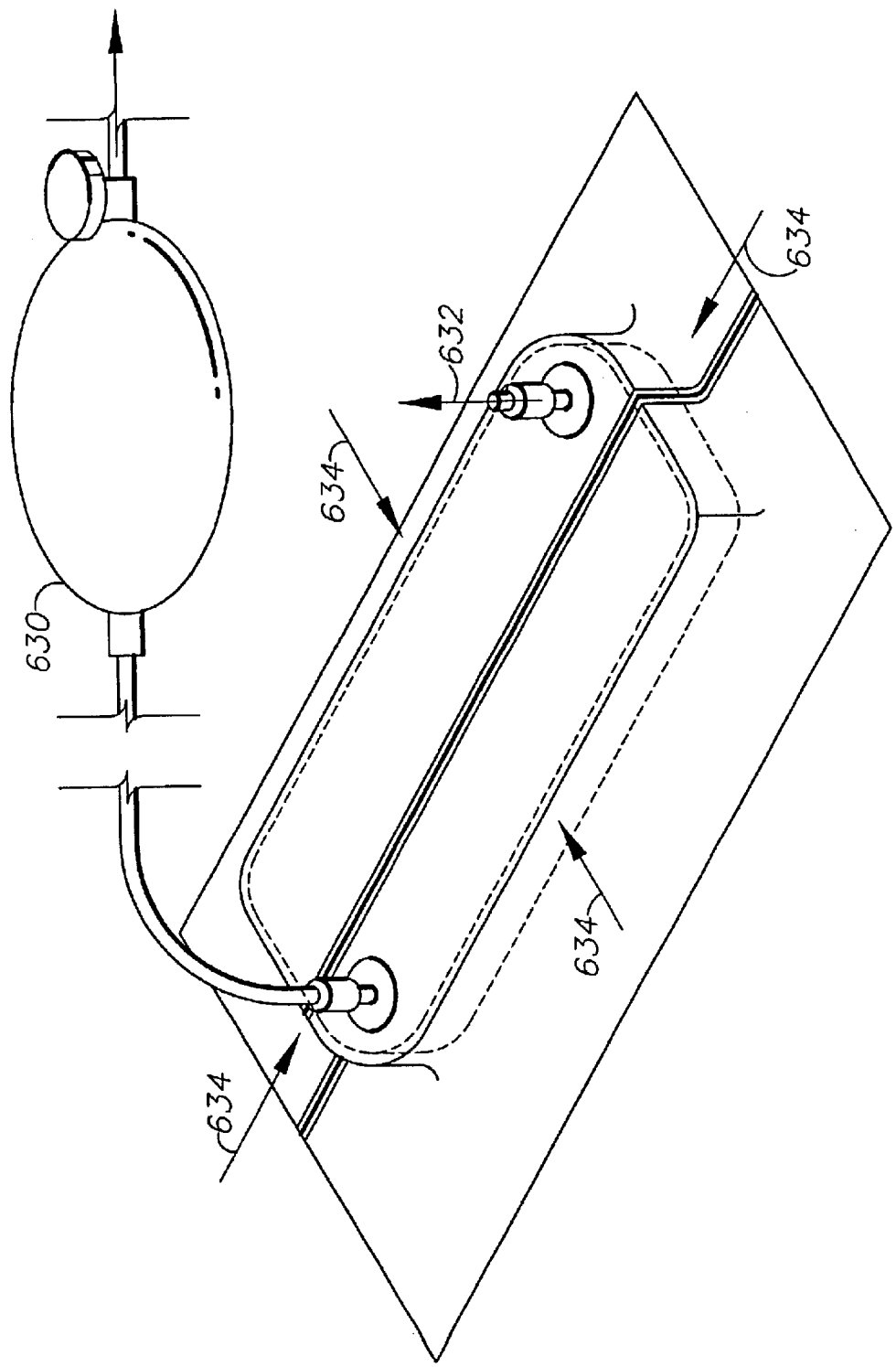
FIG. 33 is a perspective view of the dressing, shown with a squeeze bulb evacuator attached to a fluid port thereof.
Figure 36:
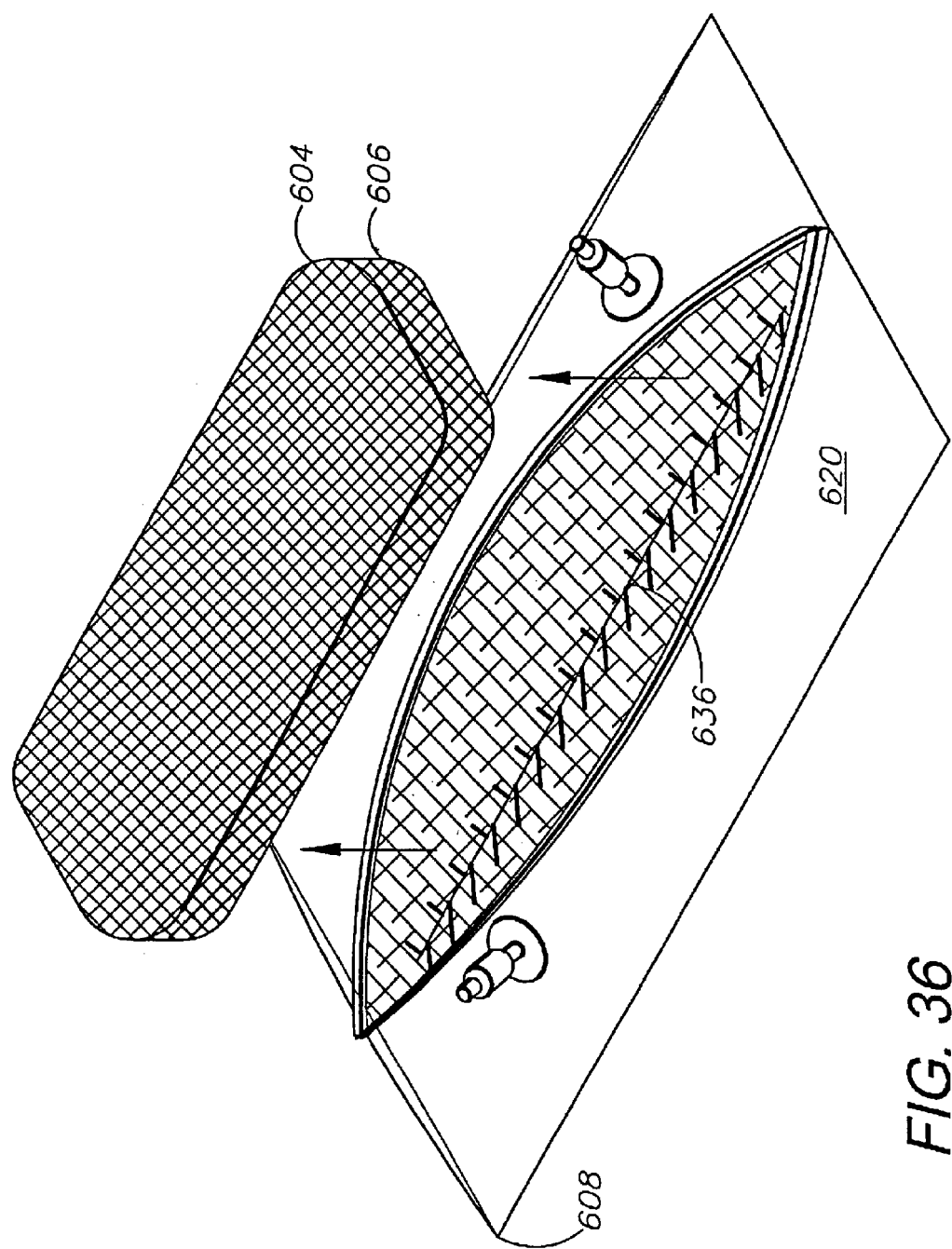
FIG. 36 is a perspective view of the dressing, shown with the foam piece removed.

A common application of the dressing 602 is on a recently-closed surgical incision for controlling bleeding and other fluid exudate. For example, the dressing 602 can be placed on the patient with its bottom panel opening 618 located over a stitch line 636 (FIG. 36). The center backing strip 614 is peeled from the bottom panel 610 to expose the opening 618 and the adhesive 628 on the bottom panel 610 (FIG. 33). The opening 618 provides a fluid transfer, which can also be provided by constructing the sheath bottom panel 610 from a permeable material, or by providing other passage configurations therethrough. The dressing 602 can then be placed on the patient, with the bottom panel adhesive providing temporary fixation. The side backing strips 612, 616 can then be removed, as shown in FIG. 32, and the bottom panel 610 completely secured to the patient.

The fluid ports 624, 626 are adapted for either extraction or infusion of fluids, or both, depending on the particular treatment methodology. For extraction purposes a vacuum source can be attached to one or both of the ports 624, 626, and can comprise a mechanical, powered pressure differential source, such as wall suction. Alternatively, hand-operated mechanical suction can be provided, such as a suction bulb 630 (FIG. 33) or a Hemovac device available from Zimmer Corp. of Warsaw, Ind. Such hand-operated suction devices can accommodate patient mobility and tend to be relatively simple to operate. Powered suction and fluid pump devices can be preprogrammed to provide intermittent and alternating suction and infusion, and to automatically respond to patient condition feedback signals. As shown in FIG. 33, the application of a negative pressure differential (suction) collapses the sheath 608 onto the foam piece 604. The various dynamic fluid forces and fluid movement effects described above can thus be brought into operation and controlled.

Figure 34:
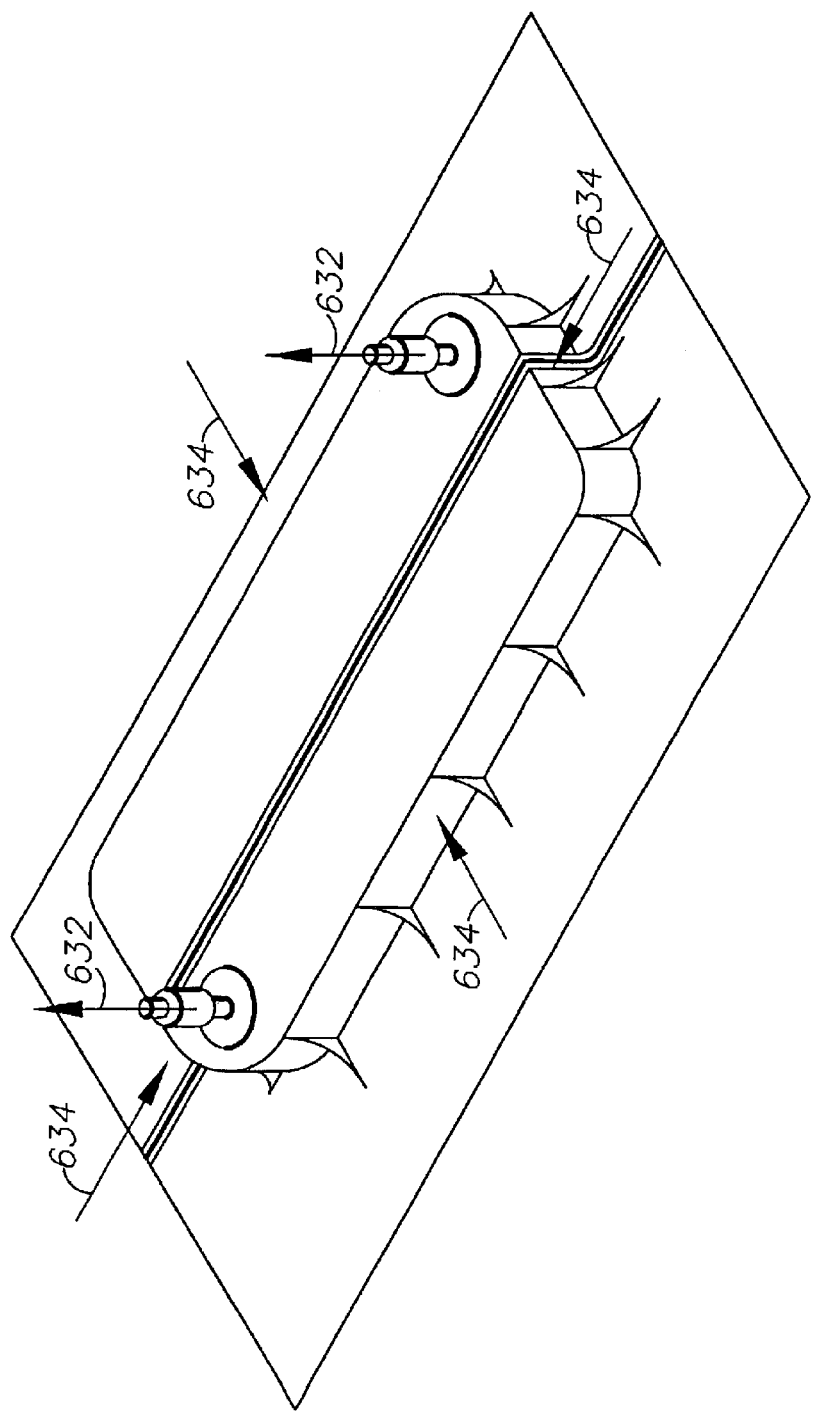
FIG. 34 is a perspective view of the dressing, shown partially-collapsed under atmospheric pressure.

FIG. 34 shows the sheath 608 further collapsing on the foam piece 604 as a result of evacuation from both of the fluid ports 24, as indicated by the fluid flow arrows 632. The ambient air pressure force arrows 634 show the application of this force, which tends to collapse the sheath 608 onto the foam piece 604.

Figure 35:
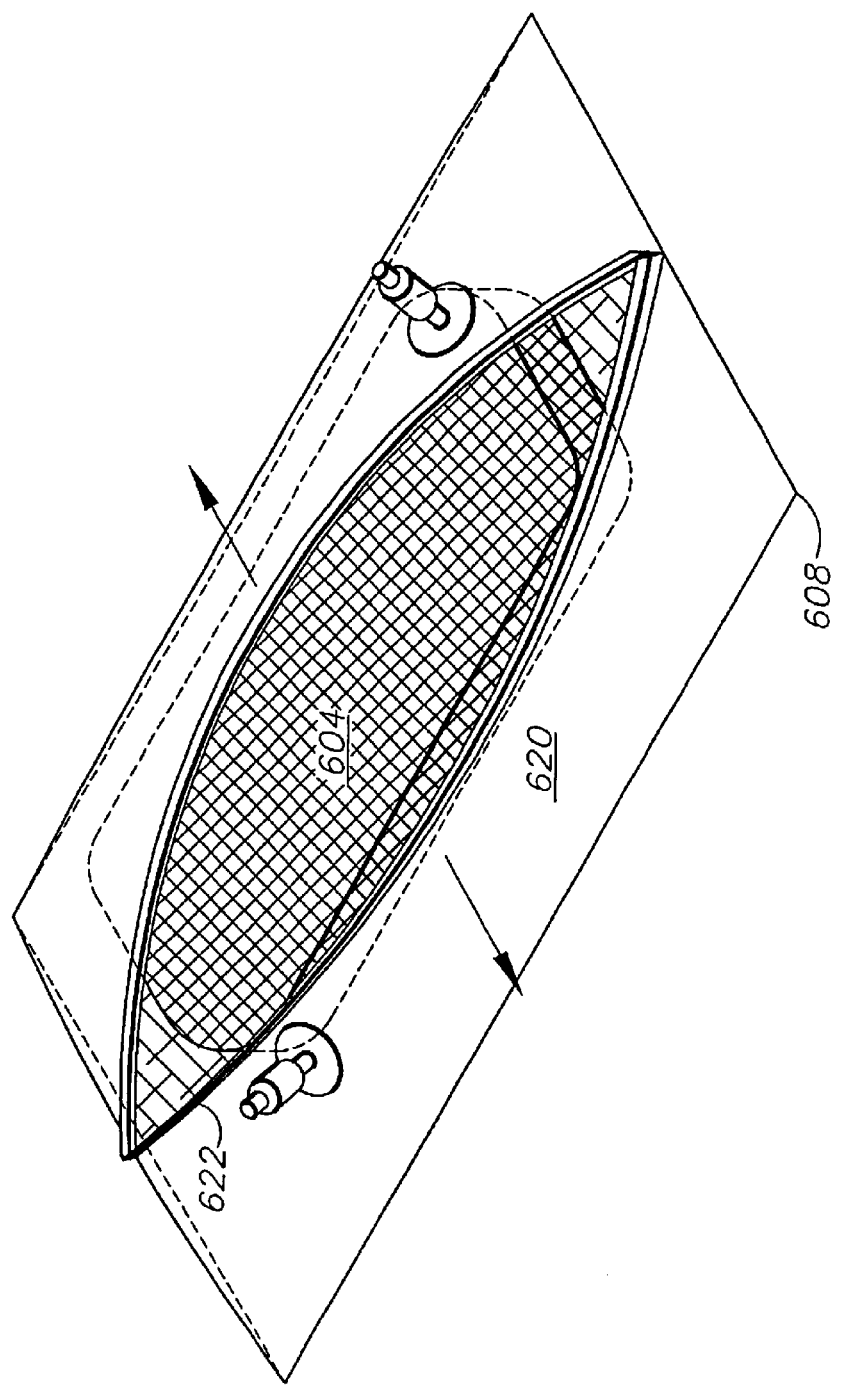
FIG. 35 is a perspective view of the dressing, shown with the seal strip open.
Figure 37:
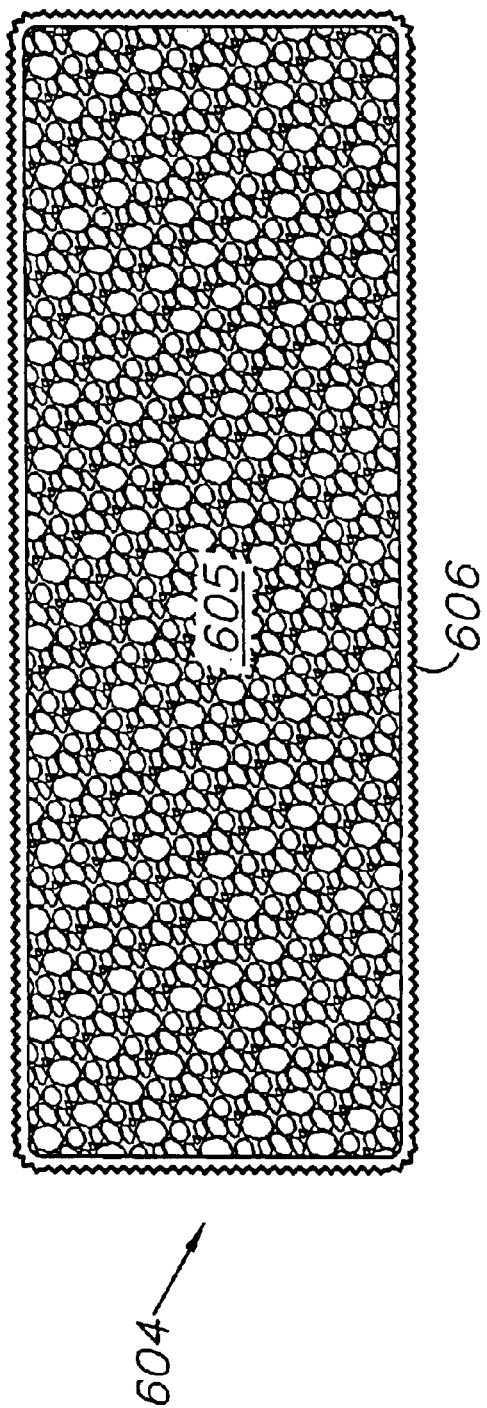
FIG. 37 is a cross-sectional view of a foam piece fully-enclosed in rayon.

FIG. 35 shows opening the seal strip 622 for access to the interior of the dressing 602. The foam piece 604 can then be removed, as shown in FIG. 36, whereby the stitch line 636 can be visually inspected and/or treated. The foam piece 604 can be flipped over or replaced, as necessary. FIG. 37 shows a cross-section of the foam piece 604, which can be completely covered in rayon or some other suitable wicking material 606 in order to accommodate placement of either side against the stitch line 636.

XI. Alternative Embodiment Dressing Assembly 702

Figure 38:
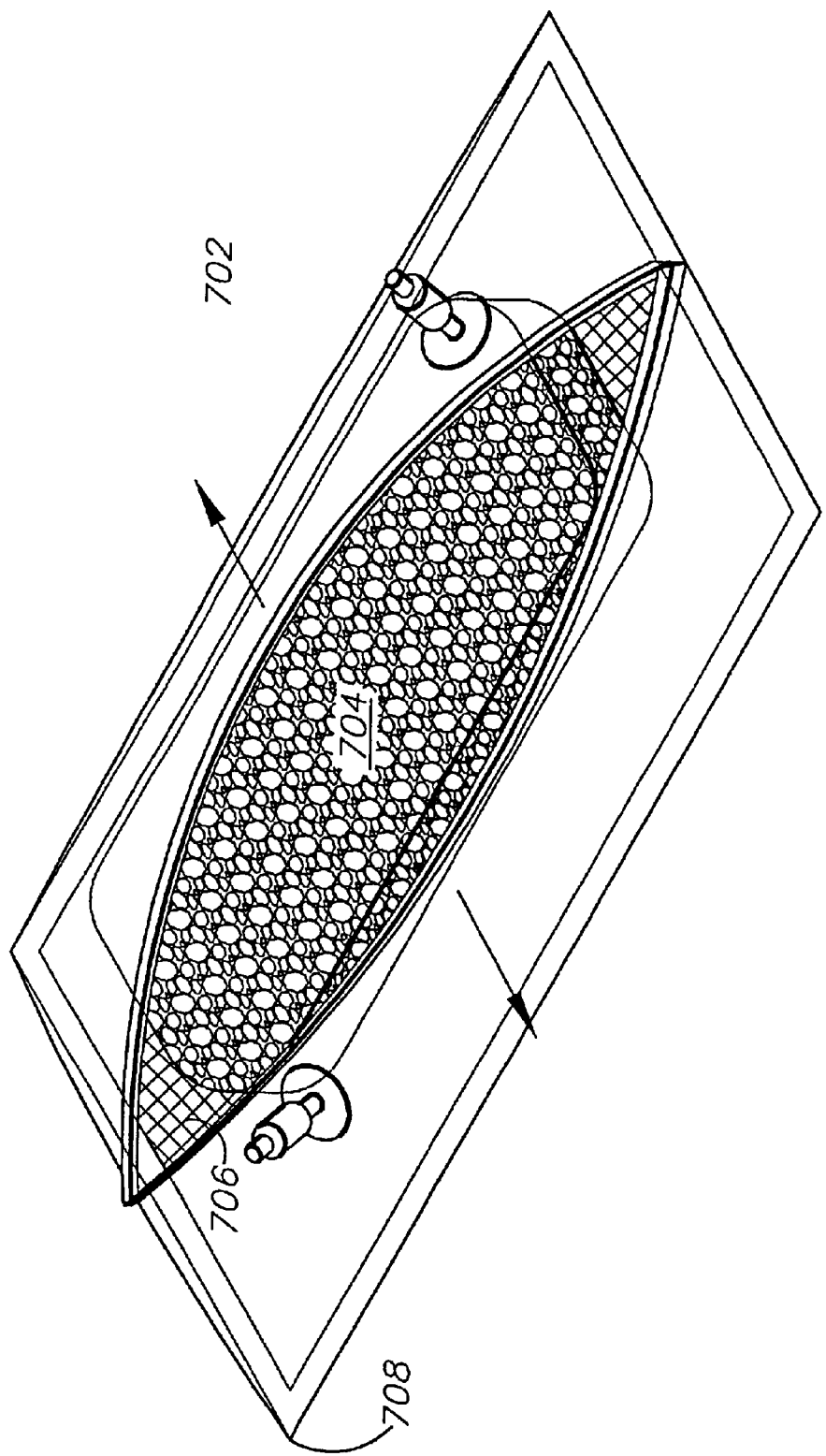
FIG. 38 is a perspective view of an alternative embodiment dressing with a separate liner and foam piece.
Figure 39:
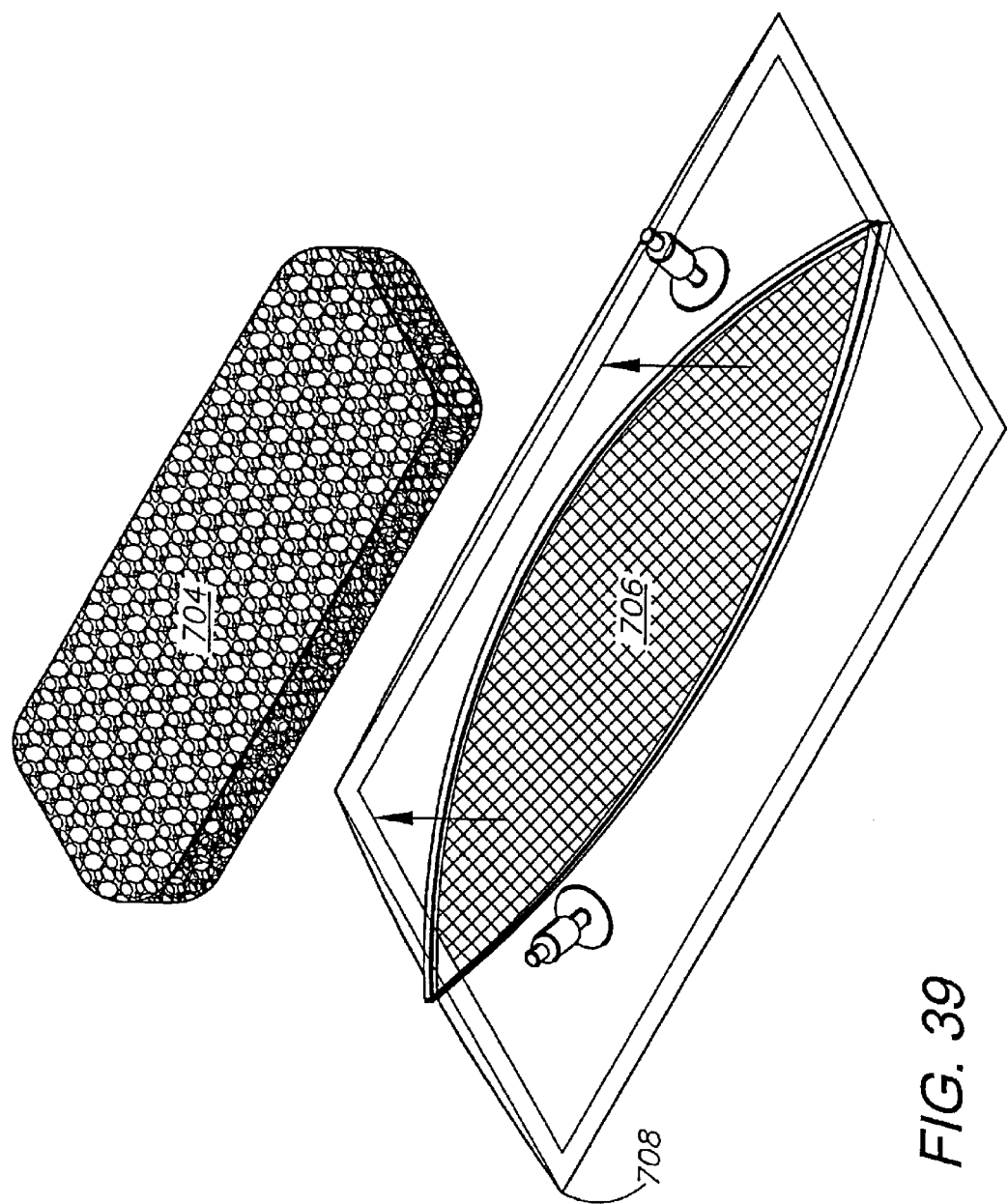
FIG. 39 is a perspective view of the dressing, shown with the foam piece for moved.
Figure 40:
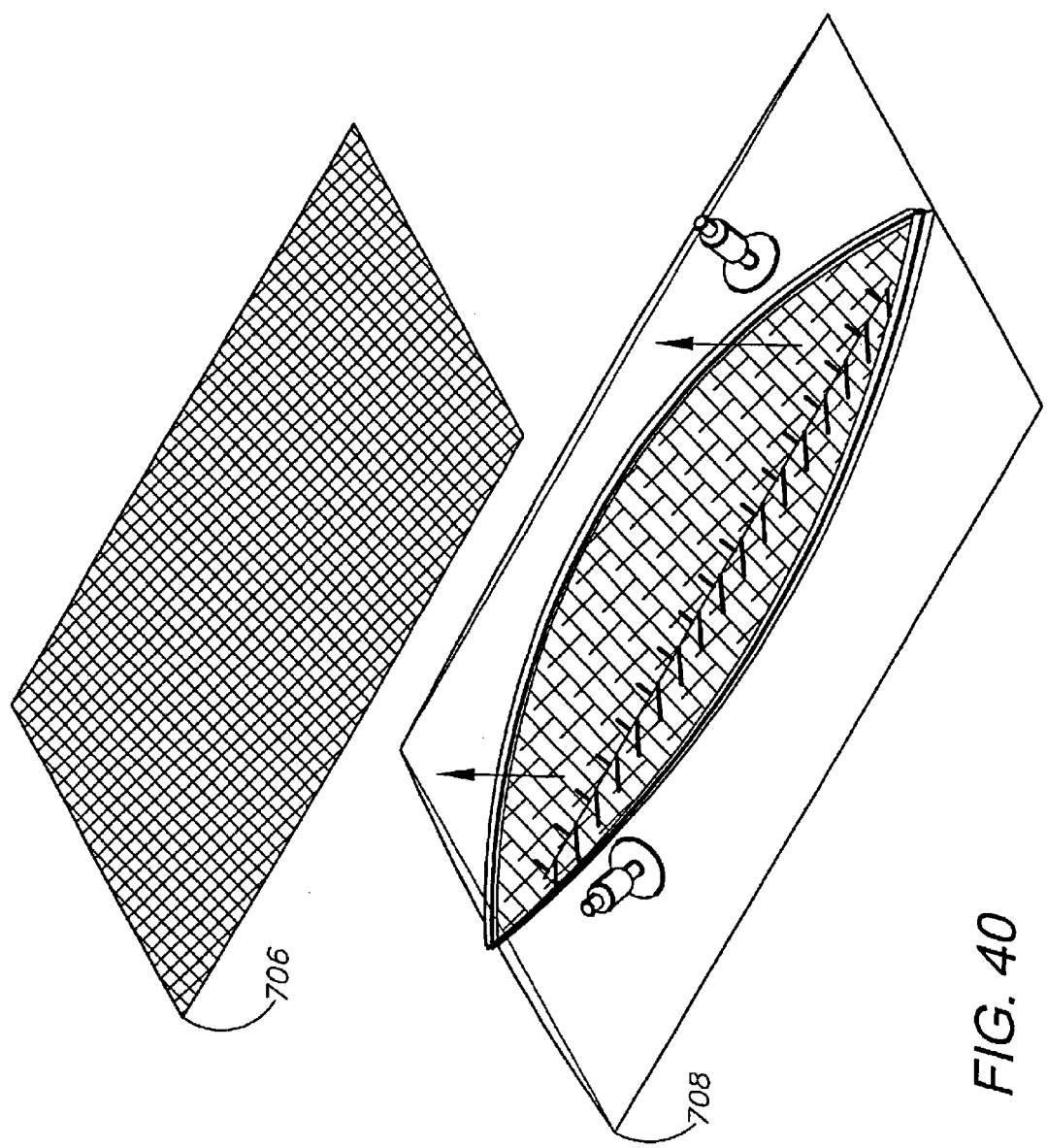
FIG. 40 is a perspective view of the dressing, shown with the liner removed.

FIGS. 38–40 show a dressing assembly 702 comprising an alternative embodiment of the present invention and including a foam piece 704 comprising any suitable hydrophobic or hydrophilic foam material. The foam piece 704 is selectively and removably located in a sheath 708, which can be similar to the sheath 608 described above. A liner 706 can comprise a piece of rayon or some other suitable material adapted to wick fluid from the stitch line 636 into the foam piece 704, and further adapted to isolate the patient from direct contact with the foam piece 704. The liner 706 can be sized to lay flat against the bottom panel of the sheath 708.

In operation, the dressing assembly 702 is adapted to utilize readily available components, such as the foam piece 704 and the liner 706, in a dressing adapted for wound inspection, wound treatment and component change procedures, all without having to remove the sheath or disturb its adhesive attachment to the patient. FIG. 39 shows removing the foam piece 704, which can be flipped over for reuse or replaced. FIG. 40 shows removing the liner 706, which can also be easily replaced. With the liner 706 removed, the stitch line 636 is exposed for stitch removal, inspection, treatment, irrigation and other procedures. The sheath 708 can then be reclosed and vacuum-assisted and/or other treatment can resume.

XII. Alternative Embodiment Dressing Assembly 802

Figure 41:
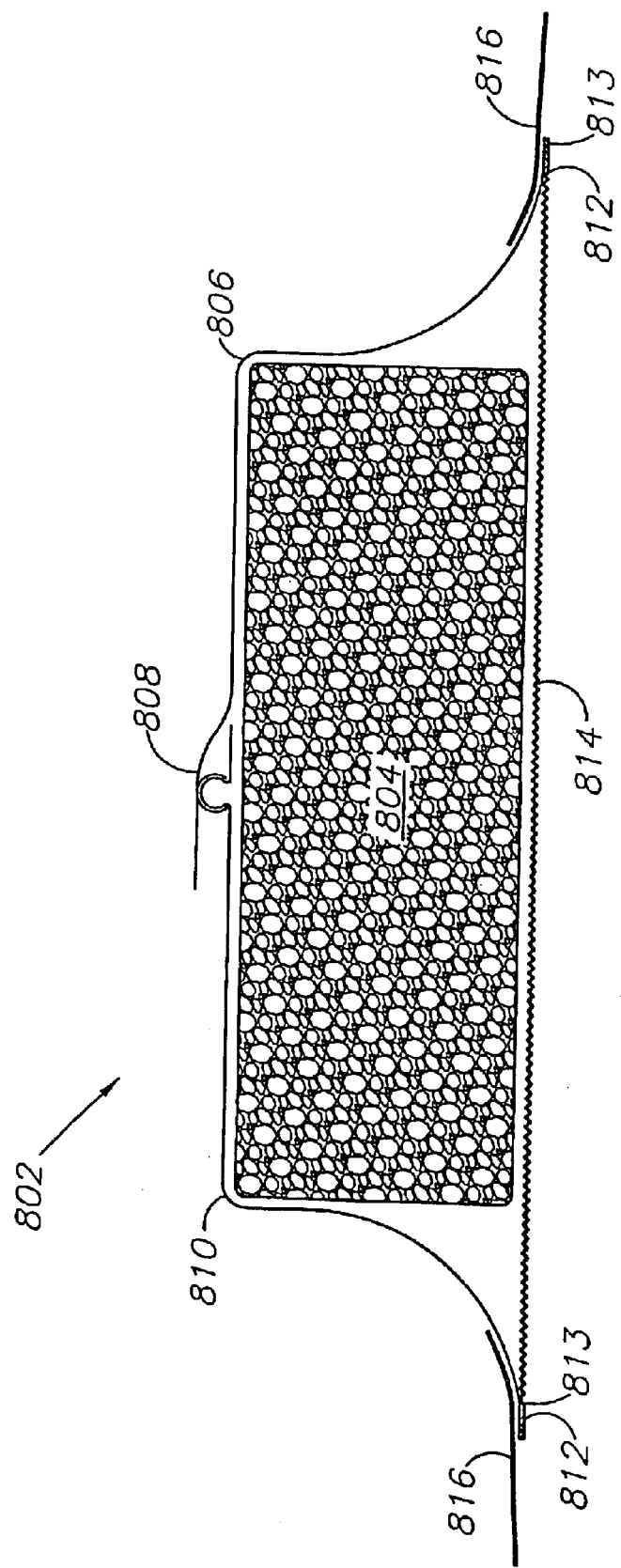
FIG. 41 is a cross-sectional view of an alternative embodiment dressing with a sheath bottom panel comprising a wicking material.

A dressing assembly 802 comprising an alternative embodiment of the present invention is shown in FIG. 41 and includes a foam piece 804 in a sheath 806 adapted for opening and closing through a reclosable seal strip 808. The sheath 806 includes an upper drape portion 810, which can comprise a suitable semi-permeable or impervious drape material. The sheath 806 includes a perimeter 812, which can be provided with an optional adhesive perimeter seal 813 adapted for providing a relatively fluid-tight seal around the sheath 806. The perimeter seal 813 can be relatively narrow in order to minimize patient discomfort, skin maceration, etc. A bottom panel 814 comprises a suitable wicking material, such as rayon, and extends to the sheath perimeter 812. The materials comprising the dressing 802 can be chosen for permeability or occlusiveness, biocompatibility, hydrophobic or hydrophilic reaction to liquids, bacteriastatic and antimicrobial properties, and other performance-related properties and criteria.

In operation, the dressing 802 is placed on the patient over a wound or stitch line. The perimeter adhesive 813 can provide temporary fixation and sealing. A strip of tape 816 can be placed over the sheath perimeter 812 for securing the sheath 806 in place. Fluid is transferred through the wicking material layer 814 to the foam piece 804 for evacuation through suitable fluid connectors, as described above, which can be attached to a vacuum source. Moreover, the dressing 802 is adapted for providing a positive pressure gradient, also as described above. The seal strip 808 permits access to the foam piece 804 for flipping over or changing, as indicated.

The foam piece 804, the drape upper portion 810 and the wicking material layer 814 can be assembled for independent movement whereby the only attachment among these components occurs around the perimeter 812 where the drape upper portion 810 is connected to the wicking material layer 814. Such independent freedom of movement permits the dressing assembly 802 to reconfigure itself and conform to the patient and various applied forces, such as pressure gradients. The individual components can thus expand and contract independently of each other without distorting the other components or interfering with the performance and comfort of the dressing assembly 802.

It is to be understood that while certain embodiments and/or aspects of the invention have been shown and described, the invention is not limited thereto and encompasses various other embodiments/aspects.

Having thus described the invention, what is claimed as new and desired to be secured by Letters Patent is:

1. A dressing assembly for a closed wound or incision, which comprises:

an external patient interface including a fluid transfer component, said fluid transfer component being adapted for transferring fluid from the closed wound or incision;

said fluid transfer component including a foam core and a wicking material piece fluidically communicating with said foam core, said wicking material piece being adapted for placement on intact skin adjacent to said closed wound or incision;

said external patient interface including an overdrape placed over said fluid transfer component in contact with a surrounding skin surface; and a pressure source connected to the fluid transfer component.

2. The dressing assembly according to claim 1, which includes:

said overdrape having an opening located over said fluid transfer component; and an access panel including said seal strip and mounted on said overdrape with said seal strip selectively providing access to said fluid transfer component through said overdrape opening.

3. The dressing assembly according to claim 1, which includes:

an internal fluid transfer component located in said wound or incision in fluidic communication with said fluid transfer component.

4. The dressing assembly according to claim 3 wherein said wound or incision includes an undermined area and said dressing assembly includes an innermost fluid transfer component located in said undermined area.

5. The dressing assembly according to claim 1 wherein said foam core comprises a hydrophobic material.

6. The dressing assembly according to claim 1, which includes:
a fluid port mounted on said overdrape and adapted for connection to said pressure source.

7. The dressing assembly according to claim 6 wherein said pressure source comprises a manually-operated vacuum-type device.

8. The dressing assembly according to claim 1, which includes:
a sheath including said overdrape and having an interior compartment receiving said foam core; and
said wicking material being located between said foam core and the patient, said wicking material being adapted to wick fluid from the patient and into the foam core.

9. The dressing assembly according to claim 8 wherein said overdrape comprises a top panel of said sheath and said wicking material comprises a bottom panel thereof.

10. The dressing assembly according to claim 9, which includes:
said sheath having a perimeter whereat said overdrape is connected to said bottom panel; and
an adhesive band around said perimeter adapted for releasably attaching said dressing assembly to the patient.

11. The dressing assembly according to claim 8, which includes:
said sheath having a bottom panel and an opening formed in said bottom panel and adapted for exposing said wicking material to the wound or incision.

12. The dressing assembly according to claim 11, which includes:
adhesive on said bottom panel adapted for releasably attaching said sheath to a patient;
a center backing strip selectively covering said adhesive on a center portion of said bottom panel; and
a pair of side backing strips for selectively covering said adhesive on side portions of said bottom panel.

13. The dressing assembly according to claim 8 wherein said sheath overdrape, said foam core and said wicking material comprise separate components adapted for independent movement with respect to each other.

14. The dressing assembly according to claim 8 wherein said wicking material comprises rayon.

15. The dressing assembly according to claim 1, which includes:
said fluid transfer component having a top, a bottom and sides;
said overdrape having an outer portion covering said fluid transfer component top and sides and having a skirt extending around said outer portion and including adhesive for releasable attachment to the patient; and
said overdrape being tucked under at least a portion of said fluid transfer component bottom.

16. The dressing assembly according to claim 15, which includes an elbow connector mounted on said overdrape and adapted for connection to said pressure source.

17. A method of dressing a closed wound or incision, which method comprises the steps of:
providing a fluid transfer component with a foam material core;
placing the fluid transfer component on the patient in fluidic connection with the closed wound or incision;
providing an overdrape and placing same over the fluid transfer component;
providing a wicking material and placing same substantially exclusively on intact skin adjacent to the closed wound or incision;
providing said overdrape with a seal strip having closed and open positions;
opening said seal strip; and
accessing said fluid transfer component through said open seal strip.

18. The method of claim 17, which includes the additional steps of:
providing an access panel including said seal strip;
providing an opening in said overdrape communicating with said fluid transfer component; and
placing said access panel on said overdrape with said seal strip located over said overdrape opening.

19. The method of claim 18, which includes the additional steps of:
providing an internal fluid transfer component within said wound or incision;
fluidically connecting said internal fluid transfer component to said external fluid transfer component;
attaching a fluid pressure source to said fluid transfer component; and
creating a pressure gradient across said external fluid transfer component.

20. A dressing assembly for a wound or incision, which comprises:
an external patient interface including an external fluid transfer component, said fluid transfer component being adapted for transferring fluid from the closed wound or incision;
said external patient interface including an overdrape placed over said fluid transfer component in contact with a surrounding skin surface; and
a reclosable seal strip connected to said overdrape and having a closed position sealing same and an open position providing access to said fluid transfer component therethrough;
an internal fluid transfer component located in said wound or incision in fluidic communication with said fluid transfer component; and
a pair of side drapes each located along a respective side of said wound or incision between said external fluid transfer component and the patient's skin.

21. A dressing assembly for a wound or incision, which comprises:
an external patient interface including an external fluid transfer component, said fluid transfer component being adapted for transferring fluid from the closed wound or incision;
said external patient interface including an overdrape placed over said fluid transfer component in contact with a surrounding skin surface; and
a reclosable seal strip connected to said overdrape and having a closed position sealing same and an open position providing access to said fluid transfer component therethrough;
said overdrape having an opening located over said fluid transfer component;
an access panel including said seal strip and mounted on said overdrape with said seal strip selectively providing access to said fluid transfer component through said overdrape opening;

said access panel having a perimeter portion with an adhesive coating adapted for attaching same to said overdrape; and said access panel having an adhesive-free central portion surrounded by said perimeter portion, said central portion including said seal strip.

22. A dressing assembly for a wound or incision, which comprises:

an external patient interface including an external fluid transfer component, said fluid transfer component being adapted for transferring fluid from the closed wound or incision;

said external patient interface including an overdrape placed over said fluid transfer component in contact with a surrounding skin surface; and a reclosable seal strip connected to said overdrape and having a closed position sealing same and an open position providing access to said fluid transfer component therethrough;

said overdrape having an opening located over said fluid transfer component;

an access panel including said seal strip and mounted on said overdrape with said seal strip selectively providing access to said fluid transfer component through said overdrape opening; and said seal strip includes a longitudinally-extending channel mounted on a first portion of said access panel and a longitudinally-extending rib mounted on a second portion of said access panel and selectively received in said channel with said seal strip in its closed configuration.

23. A dressing assembly for a wound or incision, which comprises:

an external patient interface including an external fluid transfer component, said fluid transfer component being adapted for transferring fluid from the closed wound or incision;

said external patient interface including an overdrape placed over said fluid transfer component in contact with a surrounding skin surface;

a reclosable seal strip connected to said overdrape and having a closed position sealing same and an open position providing access to said fluid transfer component therethrough;

a sheath including said overdrape and having an interior compartment receiving said foam core; and said wicking material being located between said foam core and the patient, said wicking material being adapted to wick fluid from the patient and into the foam core.

24. The dressing assembly according to claim 23 wherein said wicking material substantially covers said foam core.

25. The dressing assembly according to claim 23 wherein:

said foam core includes a top, a bottom and sides; and said wicking material covers said bottom and sides of said foam core and said core top is open.

26. A method of dressing a closed wound or incision, which method comprises the steps of:

providing a fluid transfer component with a foam material core;

placing the fluid transfer component on the patient in fluidic connection with the closed wound or incision;

providing an overdrape and placing same over the fluid transfer component;

providing a wicking material and placing same between the foam material core and the closed wound or incision;

providing said overdrape with a seal strip having closed and open positions;

opening said seal strip;

accessing said fluid transfer component through said open seal strip;

providing a sheath including a top panel comprising said overdrape;

providing said sheath with a bottom panel;

providing a fluid transfer component in said bottom panel;

placing said fluid transfer component in said sheath;

communicating fluid from said wound or incision through said fluid transfer to said fluid transfer component;

extracting said fluid transfer component from said sheath;

flipping over or replacing said fluid transfer component and reinserting same in said sheath; and closing said seal strip.

27. The method of claim 26, which includes the additional steps of:

providing a fluid port in said sheath;

connecting said fluid port to a fluid pressure source; and forming a pressure gradient across said fluid transfer component within said sheath.

* * * * *